(12) United States Patent
Lauffer et al.

(10) Patent No.: US 8,518,938 B2
(45) Date of Patent: *Aug. 27, 2013

(54) C-MET PROTEIN KINASE INHIBITORS

(75) Inventors: David J. Lauffer, Stow, MA (US); Pan Li, Lexington, MA (US); Kira McGinty, Schenectady, NY (US); Steven M. Ronkin, Watertown, MA (US); Qing Tang, Acton, MA (US); Anne-Laure Grillot, Somerville, MA (US); Nathan D. Waal, Cambridge, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/090,563

(22) Filed: Apr. 20, 2011
(Under 37 CFR 1.47)

(65) Prior Publication Data
US 2012/0165333 A1 Jun. 28, 2012

Related U.S. Application Data

(63) Continuation of application No. PCT/US2009/061253, filed on Oct. 20, 2009.

(60) Provisional application No. 61/107,013, filed on Oct. 21, 2008.

(51) Int. Cl.
*A61K 31/41* (2006.01)
*A61K 31/444* (2006.01)
*A61K 31/4545* (2006.01)
*A61K 31/5377* (2006.01)
*C07D 401/14* (2006.01)
*C07D 401/04* (2006.01)
*C07D 413/14* (2006.01)
*C07D 413/02* (2006.01)

(52) U.S. Cl.
USPC ........ 514/235.5; 514/340; 514/318; 544/124; 546/268.4; 546/194

(58) Field of Classification Search
USPC ...... 435/184; 514/215, 340, 381; 546/268.4; 548/250
See application file for complete search history.

(56) References Cited

U.S. PATENT DOCUMENTS 7,872,031 B2 * 1/2011 Lauffer et al. ............... 514/340
2011/0136789 A1 * 6/2011 Lauffer et al. ............... 514/215

FOREIGN PATENT DOCUMENTS

WO WO 2007/111904 A2 * 4/2007
WO 2007/111904 A2 10/2007
WO 2009/045992 A2 4/2009

* cited by examiner

Primary Examiner — Rebecca Anderson
Assistant Examiner — Michael Barker
(74) Attorney, Agent, or Firm — Daniel A. Pearson

(57) ABSTRACT

The present invention relates to compounds of formula I useful in the inhibition of c-Met protein kinase. The invention also provides pharmaceutically acceptable compositions comprising the compounds of the invention and methods of using the compositions in the treatment of proliferative disorders.

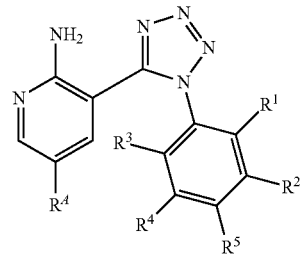

11 Claims, No Drawings

C-MET PROTEIN KINASE INHIBITORS

CROSS-REFERENCE TO RELATED APPLICATIONS

This application is a continuation of International Application No. PCT/US2009/061253, filed Oct. 20, 2009, which claims the benefit, under 35 U.S.C. §119, to United States Provisional Application No. 61/107,013, filed Oct. 21, 2008, the entire disclosures of which are incorporated herein by reference.

TECHNICAL FIELD OF THE INVENTION

The present invention relates to compounds useful as inhibitors of c-MET. The invention also provides pharmaceutically acceptable compositions comprising the compounds of the invention and methods of using the compositions in the treatment of various disorders.

BACKGROUND OF THE INVENTION

Hepatocyte growth factor (HGF), also known as scatter factor, is a multi-functional growth factor that enhances transformation and tumor development by inducing mitogenesis and cell motility. Further, HGF promotes metastasis by stimulating cell motility and invasion through various signaling pathways. In order to produce cellular effects, HGF must bind to its receptor, c-MET, a receptor tyrosine kinase. c-MET, a widely expressed heterodimeric protein comprising of a 50 kilodalton (kDa) α-subunit and a 145 kDa alpha-subunit (Maggiora et al., *J. Cell Physiol.*, 173:183-186, 1997), is overexpressed in a significant percentage of human cancers and is amplified during the transition between primary tumors and metastasis. The various cancers in which c-MET overexpression is implicated include, but are not limited to, gastric adenocarcinoma, renal cancer, small cell lung carcinoma, colorectal cancer, prostate cancer, brain cancer, liver cancer, pancreatic cancer, and breast cancer. c-MET is also implicated in atherosclerosis and lung fibrosis. Accordingly, there is a great need to develop compounds useful as inhibitors of c-MET protein kinase receptor.

SUMMARY OF THE INVENTION

It has been found that compounds of this invention, and pharmaceutically acceptable compositions thereof, are effective as inhibitors of c-MET. In particular, the compounds of the invention are superior to those compounds previously described as evidenced by their ability to selectively inhibit the activity of c-Met vs. other kinases. Accordingly, the invention features compounds having the formula:

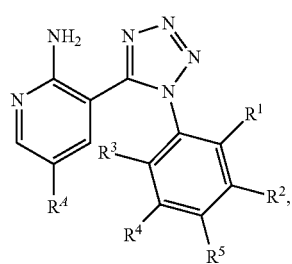

(I)

or a pharmaceutically acceptable salt thereof, wherein $R^1$, $R^2$, $R^3$, $R^4$, $R^5$ and $R^A$ are as defined below.

The invention also provides pharmaceutical compositions that include a compound of formula I and a pharmaceutically acceptable carrier, adjuvant, or vehicle. In addition, the invention provides methods of treating or lessening the severity of a proliferative disease, condition, or disorder in a patient that includes the step of administering to the patient a therapeutically effective dose of a compound of formula I, or a pharmaceutical composition thereof.

DETAILED DESCRIPTION OF THE INVENTION

Definitions and General Terminology

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry," Thomas Sorrell, University Science Books, Sausalito: 1999, and "March's Advanced Organic Chemistry," 5th Ed., Smith, M. B. and March, J., eds. John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted," whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

As described herein, when the term "optionally substituted" precedes a list, said term refers to all of the subsequent substitutable groups in that list. For example, if X is halogen; optionally substituted $C_{1-3}$ alkyl or phenyl; X may be either optionally substituted alkyl or optionally substituted phenyl. Likewise, if the term "optionally substituted" follows a list, said term also refers to all of the substitutable groups in the prior list unless otherwise indicated. For example: if X is halogen, $C_{1-3}$ alkyl, or phenyl, wherein X is optionally substituted by $J^X$, then both $C_{1-3}$ alkyl and phenyl may be optionally substituted by $J^X$. As is apparent to one having ordinary skill in the art, groups such as H, halogen, $NO_2$, CN, $NH_2$, OH, or $OCF_3$ would not be included because they are not substitutable groups. If a substituent radical or structure is not identified or defined as "optionally substituted," the substituent radical or structure is unsubstituted.

Combinations of substituents envisioned by this invention are preferably those that result in the formation of stable or chemically feasible compounds. The term "stable," as used herein, refers to compounds that are not substantially altered when subjected to conditions to allow for their production, detection, and, preferably, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group," as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments, aliphatic groups contain 1-4 carbon atoms. Suitable aliphatic groups include, but are not limited to, linear or branched, substituted or unsubstituted alkyl, alkenyl, or alkynyl groups. Further examples of aliphatic groups include methyl, ethyl, propyl, butyl, isopropyl, isobutyl, vinyl, and sec-butyl. The terms "alkyl" and the prefix "alk-," as used herein, are inclusive of both straight chain and branched saturated carbon chain. The term "alkylene," as used herein, represents a saturated divalent straight or branched chain hydrocarbon group and is exemplified by methylene, ethylene, isopropylene and the like. The term "alkylidene," as used herein, represents a divalent straight chain alkyl linking group. The term "alkenyl," as used herein, represents monovalent straight or branched chain hydrocarbon group containing one or more carbon-carbon double bonds. The term "alkynyl," as used herein, represents a monovalent straight or branched chain hydrocarbon group containing one or more carbon-carbon triple bonds.

The term "cycloaliphatic" (or "carbocycle") refers to a monocyclic $C_3C_8$ hydrocarbon or bicyclic $C_8$-$C_{12}$ hydrocarbon that is completely saturated or that contains one or more units of unsaturation, but which is not aromatic, that has a single point of attachment to the rest of the molecule, and wherein any individual ring in said bicyclic ring system has 3-7 members. Suitable cycloaliphatic groups include, but are not limited to, cycloalkyl, cycloalkenyl, and cycloalkynyl. Further examples of aliphatic groups include cyclopentyl, cyclopentenyl, cyclohexyl, cyclohexenyl, cycloheptyl, and cycloheptenyl.

The term "heterocycle," "heterocyclyl," "heterocycloaliphatic," or "heterocyclic" as used herein refers to a monocyclic, bicyclic, or tricyclic ring system in which at least one ring in the system contains one or more heteroatoms, which is the same or different, and that is completely saturated or that contains one or more units of unsaturation, but which is not aromatic, and that has a single point of attachment to the rest of the molecule. In some embodiments, the "heterocycle," "heterocyclyl," "heterocycloaliphatic," or "heterocyclic" group has three to fourteen ring members in which one or more ring members is a heteroatom independently selected from oxygen, sulfur, nitrogen, or phosphorus, and each ring in the system contains 3 to 8 ring members.

Examples of heterocyclic rings include, but are not limited to, the following monocycles: tetrahydrofuran-2-yl, tetrahydrofuran-3-yl, tetrahydrothiophen-2yl, tetrahydrothiophen-3-yl, 2-morpholino, 3-morpholino, 4-morpholino, 2-thiomorpholino, 3-thiomorpholino, 4-thiomorpholino, pyrrolidin-1-yl, pyrrolidin-2-yl, pyrrolidin-3-yl, tetrahydropiperazin-1-yl, tetrahydropiperazin-2-yl, tetrahydropiperazin-3-yl, piperidin-1-yl, piperidin-2-yl, piperidin-3-yl, piperidin-4-yl, pyrazolin-1-yl, pyrazolin-3-yl, pyrazolin-4-yl, pyrazolin-5-yl, thiazolidin-2-yl, thiazolidin-3-yl, thiazolidin-4-yl, thiazolidin-5-yl, imidazolidin-1-yl, imidazolidin-2-yl, imidazolidin-4-yl, imidazolidin-5yl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydroimidazol-2-one.

The term "heteroatom" means one or more of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or $NR^+$ (as in N-substituted pyrrolidinyl).

The term "unsaturated," as used herein, means that a moiety has one or more units of unsaturation.

The term "alkoxy," or "thioalkyl," as used herein, refers to an alkyl group, as previously defined, attached to the principal carbon chain through an oxygen ("alkoxy") or sulfur ("thioalkyl") atom.

The terms "haloalkyl," "haloalkenyl," and "haloalkoxy" mean alkyl, alkenyl, or alkoxy, as the case may be, substituted with one or more halogen atoms. The term "halogen" means F, Cl, Br, or I.

The term "aryl" used alone or as part of a larger moiety as in "aralkyl," "aralkoxy," or "aryloxyalkyl," refers to monocyclic, bicyclic, and tricyclic carbocyclic ring systems having a total of six to fourteen ring members, wherein at least one ring in the system is aromatic, wherein each ring in the system contains 3 to 7 ring members and that has a single point of attachment to the rest of the molecule. The term "aryl" may be used interchangeably with the term "aryl ring." Examples of aryl rings would include phenyl, naphthyl, and anthracene.

The term "heteroaryl," used alone or as part of a larger moiety as in "heteroaralkyl," or "heteroarylalkoxy," refers to monocyclic, bicyclic, and tricyclic ring systems having a total of five to fourteen ring members, wherein at least one ring in the system is aromatic, at least one ring in the system contains one or more heteroatoms, wherein each ring in the system contains 3 to 7 ring members and that has a single point of attachment to the rest of the molecule. The term "heteroaryl" may be used interchangeably with the term "heteroaryl ring" or the term "heteroaromatic." Further examples of heteroaryl rings include the following monocycles: furanyl (e.g., furan-2-yl or furan-3-yl); imidazolyl (e.g., N-imidazolyl, imidazol-2-yl, imidazol-4-yl, or imidazol-5-yl); isoxazolyl (e.g., isoxazol-3-yl, isoxazol-4-yl, isoxazol-5-yl); oxazolyl (e.g., oxazol-2-yl, oxazol-4-yl, or oxazol-5-yl); pyrrolyl (e.g., N-pyrrolyl, pyrrol-2-yl, or pyrrol-3-yl); pyridinyl (e.g., pyrid-2-yl, pyrid-3-yl, or pyrid-4-yl); pyrimidinyl (e.g., pyrimidin-2-yl, pyrimidin-4-yl, or pyrimidin-5-yl); pyridazinyl (e.g., pyridazin-3-yl, pyridazin-4-yl, pyridazin-5-yl, or pyridazin-6-yl); thiazolyl (e.g., thiazol-2-yl, thiazol-4-yl, or thiazol-5-yl); tetrazolyl (e.g., tetrazol-1-yl or tetrazol-5-yl); triazolyl (e.g., 2-triazolyl or 5-triazolyl), thienyl (e.g., thiophen-2-yl or thiophen-3-yl); pyrazolyl (e.g., pyrazol-2-yl, pyrazol-3-yl, or pyrazol-4-yl); isothiazolyl; 1,2,3-oxadiazolyl; 1,2,5-oxadiazolyl; 1,2,4-oxadiazolyl; 1,2,3-triazolyl; 1,2,3-thiadiazolyl; 1,3,4-thiadiazolyl; 1,2,5-thiadiazolyl; pyrazinyl; 1,3,5-triazinyl; and the following bicycles: benzimidazolyl; benzofuryl; benzothienyl; indolyl (e.g., 2-indolyl); purinyl; quinolinyl (e.g., 2-quinolinyl, 3-quinolinyl, or 4-quinolinyl); and isoquinolinyl (e.g., 1-isoquinolinyl, 3-isoquinolinyl, or 4-isoquinolinyl).

In some embodiments, an aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from those listed in the definition of $R^1$, $R^2$, $R^3$, $R^4$, $J^M$, $J^Q$, or $J^R$ below. Other suitable substituents include: halogen; —R°; —OR°; —SR°; 1,2-methylenedioxy; 1,2-ethylenedioxy; phenyl (Ph) optionally substituted with R°; —O(Ph) optionally substituted with R°; —$(CH_2)_{1-2}$(Ph), optionally substituted with R°; —CH=CH(Ph), optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —C(O)R°; —C(S)R°; —C(O)N(R°)$_2$; —C(S)N(R°)$_2$; —OC(O)N(R°)$_2$; —OC(O)R°; —C(O)N(OR°)R°; —C(NOR°)R°; —S(O)$_2$R°; —S(O)$_2$OR°; —S(O)$_2$ N(R°)$_2$; —S(O)R°; —NR°S(O)$_2$N(R°)$_2$; —NR°S(O)$_2$R°; —N(OR°)R°; —C(=NH)—N(R°)$_2$; —(CH$_2$)$_{0-2}$NHC(O)R°; -L-R°; -L-N(R°)$_2$; -L-SR°; -L-OR°; -L-(C$_{3-10}$ cycloaliphatic), -L-(C$_{6-10}$ aryl), -L-(5-10 membered heteroaryl), -L-(5-10 membered heterocyclyl), oxo, C$_{1-4}$ haloalkoxy, C$_{1-4}$ haloalkyl, -L-NO$_2$, -L-CN, -L-OH, -L-CF$_3$; or two substituents, together with the intervening atoms to which they are bound, form a 5-7 membered saturated, unsaturated, or partially saturated ring, wherein L is a C$_{1-6}$ alkylene group in which up to three methylene units are replaced by —NH—, —NR°—, —O—, —S—, —C(O)O—, —OC(O)—, —C(O)CO—, —C(O)—, —C(O)NH—, —C(O)NR°—, —C(=N—CN), —NHCO—, —NR°CO—, —NHC(O)O—, —NR°C(O)O—, —S(O)$_2$NH—, —S(O)$_2$NR°—, —NHS(O)$_2$—, —NR°S(O)$_2$—, —NHC(O)NH—, —NR°C(O)NH—, —NHC(O)NR°—, —NR°C(O)NR°, —OC(O)NH—, —OC(O)NR°—, —NHS(O)$_2$NH—, —NR°S(O)$_2$NH—, —NHS(O)$_2$NR°—, —NR°S(O)$_2$NR°—, —S(O)—, or —S(O)$_2$—, and wherein each independent occurrence of R° is selected from hydrogen, optionally substituted C$_{1-6}$ aliphatic, an unsubstituted 5-8 membered heteroaryl or heterocyclic ring, phenyl, —O(Ph), or —CH$_2$(Ph), or, two independent occurrences of R°, on the same substituent or different substituents, taken together with the atom(s) to which each R°group is bound, form a 5-8-membered heterocyclyl, aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group of R° are selected from NH$_2$, NH(C$_{1-4}$aliphatic), N(C$_{1-4}$ aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$aliphatic, wherein each of the foregoing C$_{1-4}$aliphatic groups of R° is unsubstituted.

In some embodiments, an aliphatic, cycloaliphatic, heteroaliphatic group, or a non-aromatic heterocyclic ring may contain one or more substituents. In some instances two substituents, on the same atom or on different atoms, together with the intervening atoms to which they are bound, form a 5-7 membered saturated, unsaturated, or partially saturated ring containing 0-3 heteroatoms selected from N, O, or S. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHS(O)$_2$ (alkyl), or =NR*, where each R* is independently selected from hydrogen or an optionally substituted C$_{1-6}$ aliphatic, or two R* on the same nitrogen are taken together with the nitrogen to form a 5-8 membered heterocyclyl or heteroaryl ring having 1-3 heteroatoms independently selected from nitrogen, oxygen, and sulfur. Optional substituents on the aliphatic group of R* are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo (C$_{1-4}$ aliphatic), wherein each of the foregoing C$_{1-4}$aliphatic groups of R* is unsubstituted.

In some embodiments, optional substituents on the nitrogen of a non-aromatic heterocyclic ring include —R$^+$, —N(R$^+$)$_2$, —C(O)R$^+$, —C(O)OR$^+$, —C(O)C(O)R$^+$, —C(O)CH$_2$C(O)R$^+$, —S(O)$_2$R$^+$, —S(O)$_2$N(R$^+$)$_2$, —C(=S)N(R$^+$)$_2$, —C(=NH)—N(R$^+$)$_2$, or —NR$^+$S(O)$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$ (Ph); optionally substituted —CH=CH(Ph); or an unsubstituted 5-6 membered heteroaryl or heterocyclic ring having one to four heteroatoms independently selected from oxygen, nitrogen, or sulfur, or two independent occurrences of R$^+$, on the same substituent or different substituents, taken together with the atom(s) to which each R$^+$ group is bound, form a phenyl, 5-8-membered heterocyclyl, 5-8-membered heteroaryl, or a 3-8 membered cycloalkyl ring, wherein said heteroaryl or heterocyclyl ring has 1-3 heteroatoms independently selected from nitrogen, oxygen, or sulfur. Optional substituents on the aliphatic group or the phenyl ring of R$^+$ are selected from —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —C(O)OH, —C(O)O(C$_{1-4}$ aliphatic), —O(halo(C$_{1-4}$ aliphatic)), or halo(C$_{1-4}$ aliphatic), wherein each of the foregoing C$_{1-4}$aliphatic groups of R$^+$ is unsubstituted.

As detailed above, in some embodiments, two independent occurrences of R° (or R$^+$, or any other variable similarly defined herein), may be taken together with the atom(s) to which each variable is bound to form a phenyl, 5-8-membered heterocyclyl, 5-8-membered heteroaryl, or a 3-8 membered cycloalkyl ring. Exemplary rings that are formed when two independent occurrences of R° (or R$^+$, or any other variable similarly defined herein) are taken together with the atom(s) to which each variable is bound include, but are not limited to the following: a) two independent occurrences of R° (or R$^+$, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R$^+$, or any other variable similarly defined herein) that are bound to different atoms and are taken together with both of those atoms to form a ring, for example where a phenyl group is substituted with two occurrences of OR°

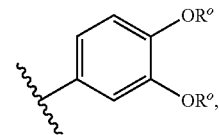

these two occurrences of R° are taken together with the oxygen atoms to which they are bound to form a fused 6-membered oxygen containing ring:

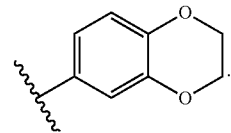 [SMILES: *c1ccc2c(c1)OCCO2]

It will be appreciated that a variety of other rings can be formed when two independent occurrences of R° (or R$^+$, or any other variable similarly defined herein) are taken together with the atom(s) to which each variable is bound and that the examples detailed above are not intended to be limiting.

In some embodiments, a methylene unit of the alkyl or aliphatic chain is optionally replaced with another atom or group. Examples of such atoms or groups would include, but are not limited to, —NR°—, —O—, —S—, —C(O)O—, —OC(O)—, —C(O)CO—, —C(O)—, —C(O)NR°—, —C(=N—CN), —NR°CO—, —NR°C(O)O—, —S(O)$_2$NR°—, —NR°S(O)$_2$—, —NR°C(O)NR°—, —OC(O)NR°—, —NR°S(O)$_2$NR°—, —S(O)—, or —S(O)$_2$—, wherein R° is defined herein. Unless otherwise specified, the optional replacements form a chemically stable compound. Optional atom or group replacements can occur both within the chain and at either end of the chain; i.e. both at the point of attachment and/or also at the terminal end. Two optional replacements can also be adjacent to each other within a chain so long as it results in a chemically stable compound. Unless otherwise specified, if the replacement occurs at the terminal end, the replacement atom is bound to an H on the terminal end. For example, if one methylene unit of —CH$_2$CH$_2$CH$_3$ was optionally replaced with —O—, the resulting compound could be —OCH$_2$CH$_3$, —CH$_2$OCH$_3$, or —CH$_2$CH$_2$OH.

As described herein, a bond drawn from a substituent to the center of one ring within a multiple-ring system (as shown below) represents substitution of the substituent at any substitutable position in any of the rings within the multiple ring system. For example, Figure a represents possible substitution in any of the positions shown in Figure b.

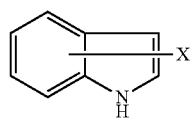

FIG. a

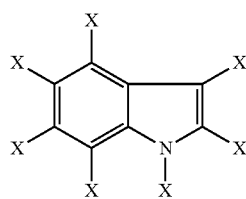

FIG. b

This also applies to multiple ring systems fused to optional ring systems (which would be represented by dotted lines). For example, in Figure c, X is an optional substituent both for ring A and ring B.

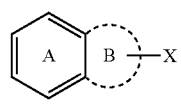

FIG. c

If, however, two rings in a multiple ring system each have different substituents drawn from the center of each ring, then, unless otherwise specified, each substituent only represents substitution on the ring to which it is attached. For example, in Figure d, Y is an optionally substituent for ring A only, and X is an optional substituent for ring B only.

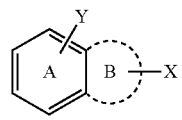

FIG. d

The term "protecting group," as used herein, represent those groups intended to protect a functional group, such as, for example, an alcohol, amine, carboxyl, carbonyl, etc., against undesirable reactions during synthetic procedures. Commonly used protecting groups are disclosed in Greene and Wuts, Protective Groups in Organic Synthesis, 3$^{rd}$ Edition (John Wiley & Sons, New York, 1999), which is incorporated herein by reference. Examples of nitrogen protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl and chiral auxiliaries such as protected or unprotected D, L or D, L-amino acids such as alanine, leucine, phenylalanine and the like; sulfonyl groups such as benzenesulfonyl, p-toluenesulfonyl and the like; carbamate groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl and the like, arylalkyl groups such as benzyl, triphenylmethyl, benzyloxymethyl and the like and silyl groups such as trimethylsilyl and the like. Preferred N-protecting groups are formyl, acetyl, benzoyl, pivaloyl, t-butylacetyl, alanyl, phenylsulfonyl, benzyl, t-butyloxycarbonyl (Boc) and benzyloxycarbonyl (Cbz).

The term "prodrug," as used herein, represents a compound that is transformed in vivo into a compound of formula I, or a compound listed in Table 1. Such a transformation can be affected, for example, by hydrolysis in blood or enzymatic transformation of the prodrug form to the parent form in blood or tissue. Prodrugs of the compounds of the invention may be, for example, esters. Esters that may be utilized as prodrugs in the present invention are phenyl esters, aliphatic (C$_1$-C$_{24}$) esters, acyloxymethyl esters, carbonates, carbamates, and amino acid esters. For example, a compound of the invention that contains an OH group may be acylated at this position in its prodrug form. Other prodrug forms include phosphates, such as, for example those phosphates resulting from the phosphorylation of an OH group on the parent compound. A thorough discussion of prodrugs is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and Judkins et al., Synthetic Communications 26(23):4351-4367, 1996, each of which is incorporated herein by reference.

Unless otherwise stated, structures depicted herein are also meant to include all isomeric (e.g., enantiomeric, diastereomeric, and geometric (or conformational)) forms of the structure; for example, the (R) and (S) configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays, or as c-MET inhibitors with improved therapeutic profile.

Description of Compounds of the Invention

In a first aspect, the invention features a compound having the formula:

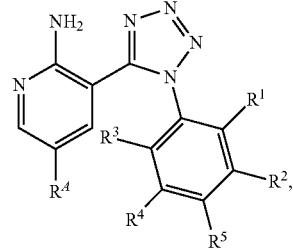

(I)

or a pharmaceutically acceptable salt thereof, wherein $R^A$ is a phenyl ring or 5 to 9 membered heteroaryl ring having up to 2 heteroatoms selected from N, O, or S, wherein said phenyl or heteroaryl ring is optionally substituted with up to 2 groups selected from halogen, $C_{1-5}$ aliphatic, —NR'C(O)R', —C(O)N(R')$_2$, —OR', —(CH$_2$)$_{0-2}$N(R')$_2$, tetrahydropyranyl, or piperidinyl;

R' is hydrogen or $C_{1-4}$ alkyl;

each of $R^1$, $R^2$, $R^3$, and $R^4$ is, individually, hydrogen, Cl, or F, wherein at least one of $R^1$, $R^2$, $R^3$, and $R^4$ is Cl or F;

$R^5$ is

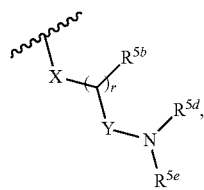

wherein

X is O or NR$^{5a}$

Y is $C_{1-4}$ aliphatic or $C_{3-6}$ cycloaliphatic, optionally substituted with R$^{5c}$, r is 0 or 1, each of R$^{5a}$, R$^{5b}$, R$^{5c}$, R$^{5d}$ and R$^{5e}$ is, independently, hydrogen or $C_{1-4}$ aliphatic, wherein R$^{5a}$ and R$^{5d}$ or R$^{5c}$ and R$^{5d}$ together optionally form a pyrrolidine or piperidine ring, R$^{5b}$ and R$^{5c}$ together optionally form a 5-6-membered carbocyclic ring, and R$^{5d}$ and R$^{5e}$ together optionally form a pyrrolidine, piperidine or morpholine ring.

In one embodiment of compounds of formula I, R$^A$ is an optionally substituted pyrazol-4-yl, thiophen-3-yl, thiophen-2-yl, benzo[b]thiophen-2-yl, phenyl, benzo[b]thiophen-3-yl, pyridine-4-yl, pyridine-3-yl, or pyrimidin-5-yl ring. In a further embodiment, R$^A$ is an optionally substituted pyrazol-4-yl, thiophen-3-yl, or thiophen-2-yl ring. Further still, R$^A$ is selected from:

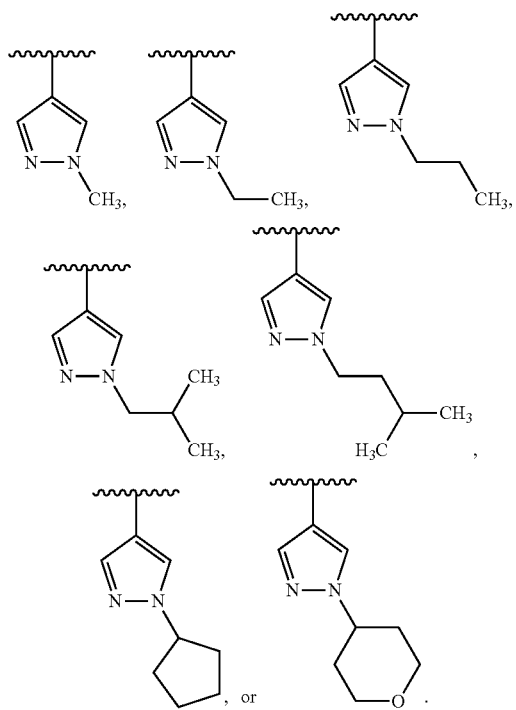

, or

In one embodiment of compounds of formula I, X is O and the number of atoms between X and N(R$^{5d}$)(R$^{5e}$) is 3, 4, or 5. In a further embodiment, R$^5$ is selected from

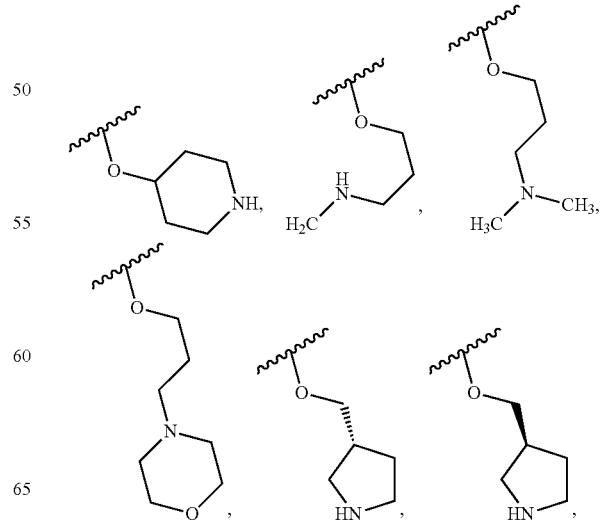

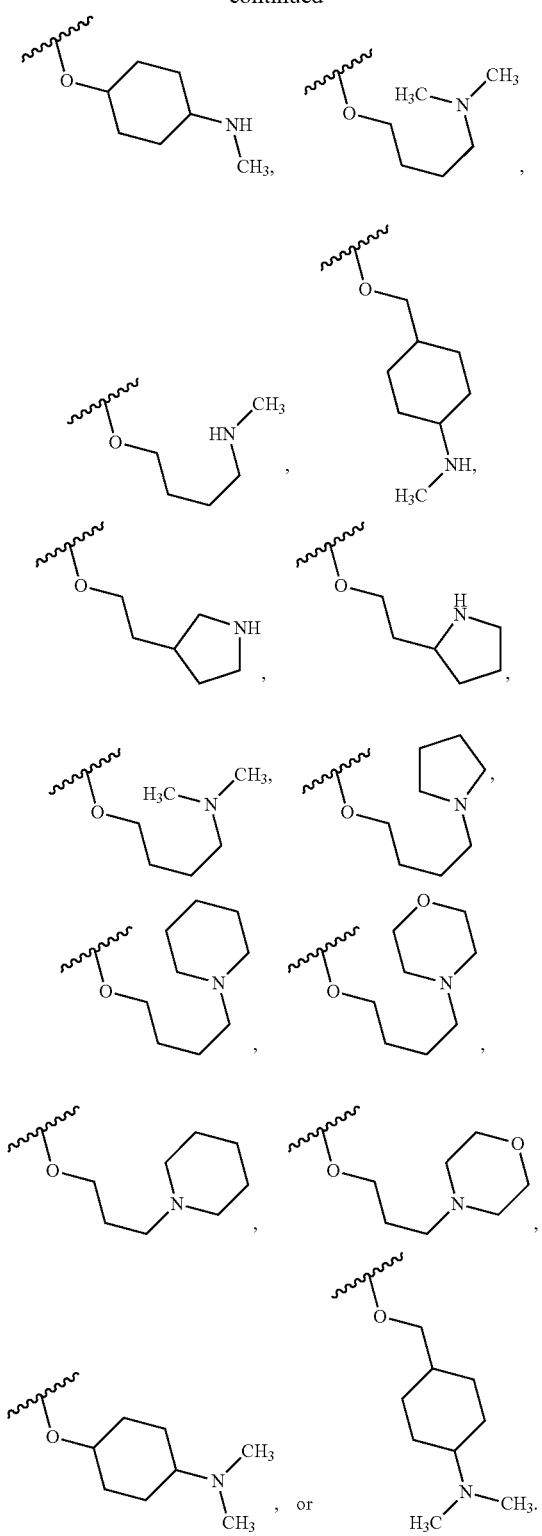
In one embodiment of compounds of formula I, one or two of $R^1$, $R^2$, $R^3$, and $R^4$ is fluorine and the remainder of $R^1$, $R^2$, $R^3$, and $R^4$ are hydrogen. In a further embodiment, each of $R^1$ and $R^2$ is fluorine and each of $R^3$ and $R^4$ is hydrogen.
In another aspect, the invention features a compound in Table 1.

TABLE 1-continued
Compounds of Formula I
5 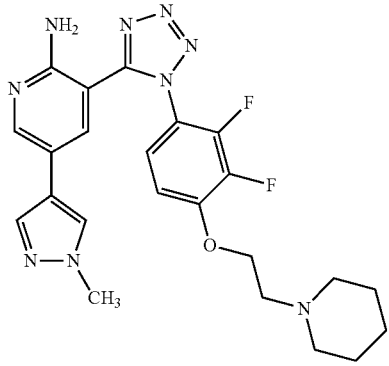 [SMILES: Cn1cc(-c2cnc(N)c(-c3nnnn3-c3ccc(OCCN4CCCCC4)c(F)c3F)c2)cn1]
6 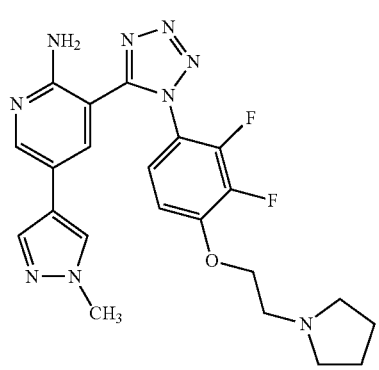 [SMILES: Cn1cc(-c2cnc(N)c(-c3nnnn3-c3ccc(OCCN4CCCC4)c(F)c3F)c2)cn1]
7 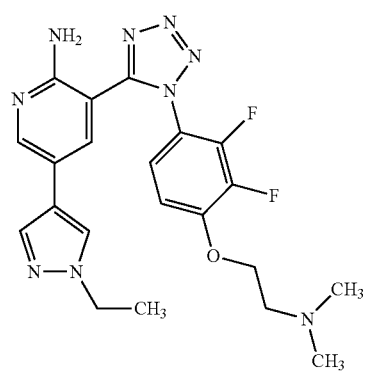 [SMILES: CCn1cc(-c2cnc(N)c(-c3nnnn3-c3ccc(OCCN(C)C)c(F)c3F)c2)cn1]
8 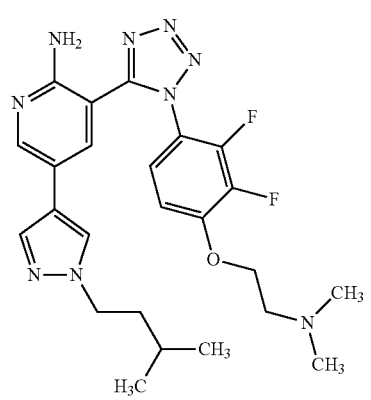 [SMILES: CC(C)CCn1cc(-c2cnc(N)c(-c3nnnn3-c3ccc(OCCN(C)C)c(F)c3F)c2)cn1]
TABLE 1-continued
Compounds of Formula I
9 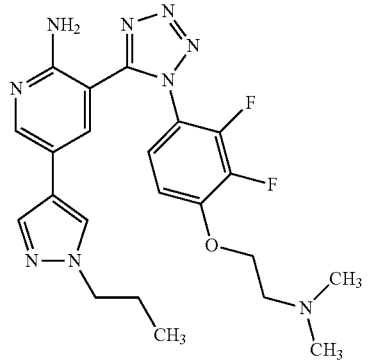 [SMILES: CCCn1cc(-c2cnc(N)c(-c3nnnn3-c3ccc(OCCN(C)C)c(F)c3F)c2)cn1]
10 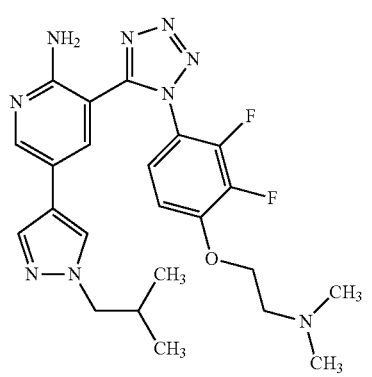 [SMILES: CC(C)Cn1cc(-c2cnc(N)c(-c3nnnn3-c3ccc(OCCN(C)C)c(F)c3F)c2)cn1]
11 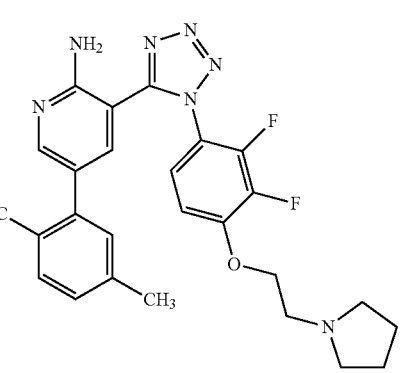
12 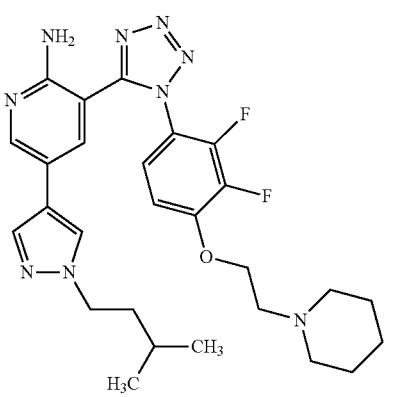 [SMILES: CC(C)CCn1cc(-c2cnc(N)c(-c3nnnn3-c3ccc(OCCN4CCCCC4)c(F)c3F)c2)cn1]

TABLE 1-continued
Compounds of Formula I
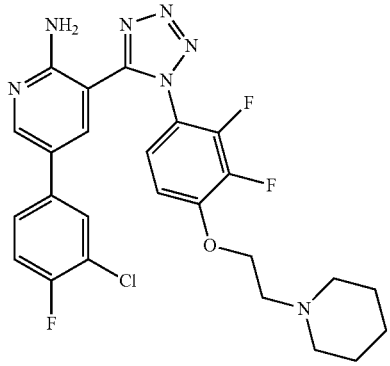 [SMILES: Nc1ncc(-c2ccc(F)c(Cl)c2)cc1-c1nnnn1-c1ccc(OCCN2CCCCC2)c(F)c1F]
13
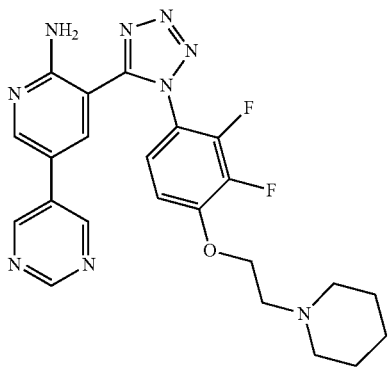 [SMILES: Nc1ncc(-c2cncnc2)cc1-c1nnnn1-c1ccc(OCCN2CCCCC2)c(F)c1F]
14
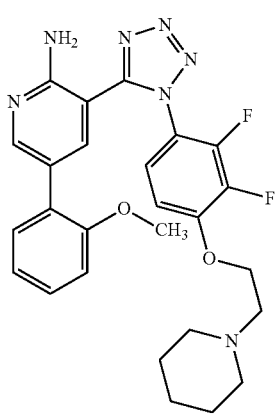 [SMILES: COc1ccccc1-c1cnc(N)c(-c2nnnn2-c2ccc(OCCN3CCCCC3)c(F)c2F)c1]
15
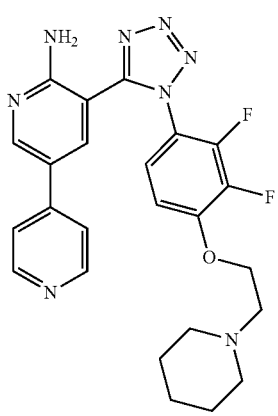 [SMILES: Nc1ncc(-c2ccncc2)cc1-c1nnnn1-c1ccc(OCCN2CCCCC2)c(F)c1F]
16
TABLE 1-continued
Compounds of Formula I
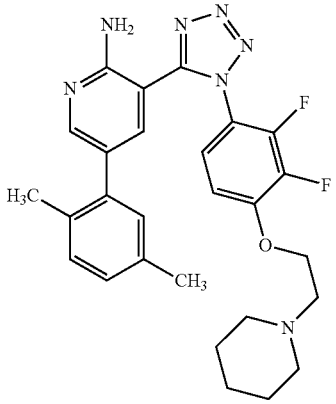 [SMILES: Cc1ccc(C)c(-c2cnc(N)c(-c3nnnn3-c3ccc(OCCN4CCCCC4)c(F)c3F)c2)c1]
17
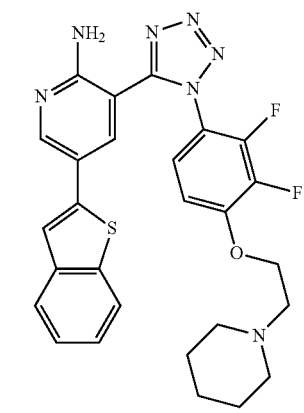 [SMILES: Nc1ncc(-c2cc3ccccc3s2)cc1-c1nnnn1-c1ccc(OCCN2CCCCC2)c(F)c1F]
18
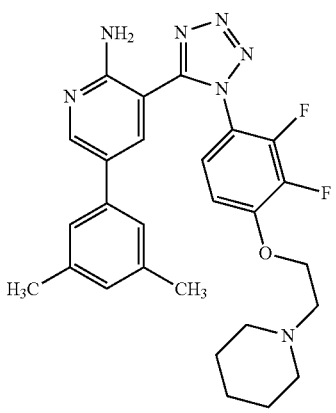 [SMILES: Cc1cc(C)cc(-c2cnc(N)c(-c3nnnn3-c3ccc(OCCN4CCCCC4)c(F)c3F)c2)c1]
19

TABLE 1-continued
Compounds of Formula I
20 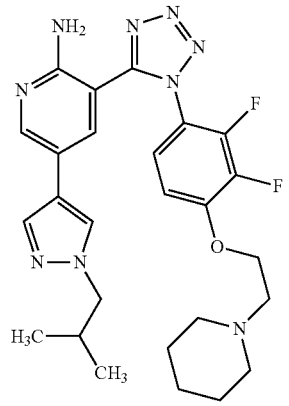 [SMILES: CC(C)Cn1cc(-c2cnc(N)c(-c3nnnn3-c3ccc(OCCN4CCCCC4)c(F)c3F)c2)cn1]
21 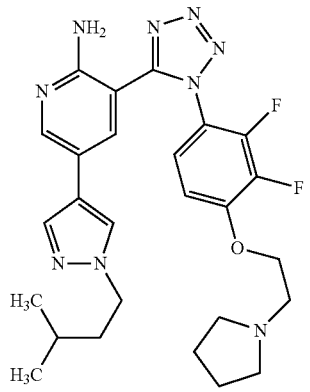 [SMILES: CC(C)CCn1cc(-c2cnc(N)c(-c3nnnn3-c3ccc(OCCN4CCCC4)c(F)c3F)c2)cn1]
22 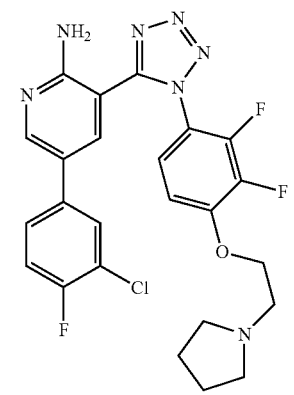 [SMILES: Nc1ncc(-c2ccc(F)c(Cl)c2)cc1-c1nnnn1-c1ccc(OCCN2CCCC2)c(F)c1F]
23 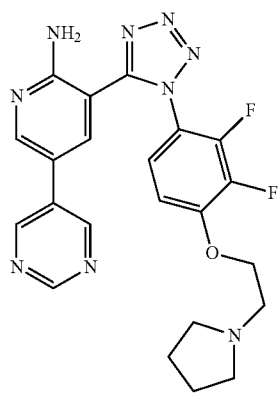 [SMILES: Nc1ncc(-c2cncnc2)cc1-c1nnnn1-c1ccc(OCCN2CCCC2)c(F)c1F]
TABLE 1-continued
Compounds of Formula I
24 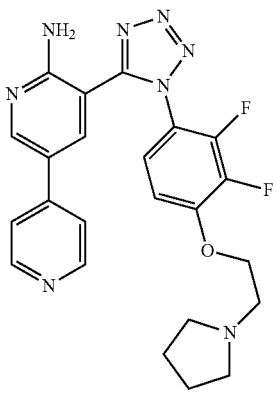
25 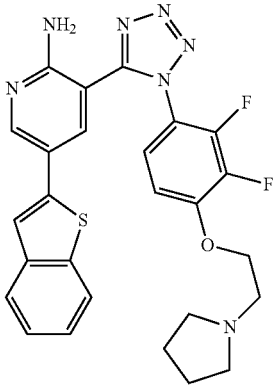 [SMILES: Nc1ncc(-c2cc3ccccc3s2)cc1-c1nnnn1-c1ccc(OCCN2CCCC2)c(F)c1F]
26 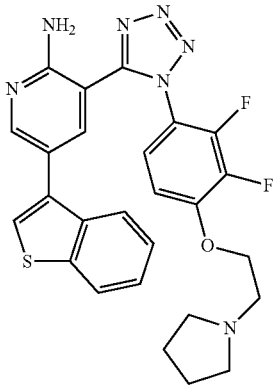 [SMILES: Nc1ncc(-c2csc3ccccc23)cc1-c1nnnn1-c1ccc(OCCN2CCCC2)c(F)c1F]
27 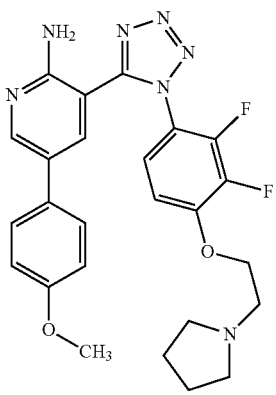 [SMILES: COc1ccc(-c2cnc(N)c(-c3nnnn3-c3ccc(OCCN4CCCC4)c(F)c3F)c2)cc1]

TABLE 1-continued
Compounds of Formula I
28 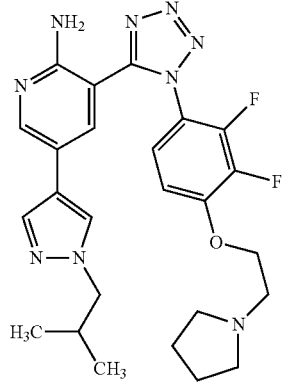 [SMILES: CC(C)Cn1cc(-c2cnc(N)c(-c3nnnn3-c3ccc(OCCN4CCCC4)c(F)c3F)c2)cn1]
29 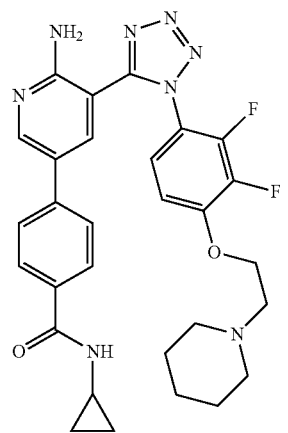 [SMILES: Nc1ncc(-c2ccc(C(=O)NC3CC3)cc2)cc1-c1nnnn1-c1ccc(OCCN2CCCCC2)c(F)c1F]
30 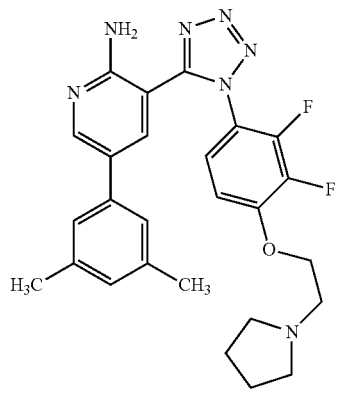 [SMILES: Cc1cc(C)cc(-c2cnc(N)c(-c3nnnn3-c3ccc(OCCN4CCCC4)c(F)c3F)c2)c1]
31 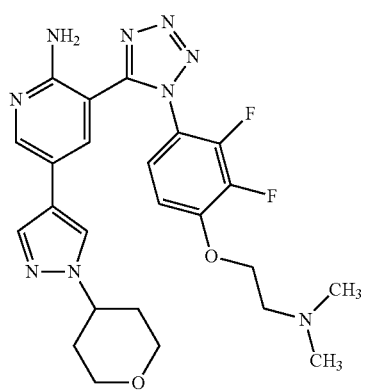 [SMILES: CN(C)CCOc1ccc(-n2nnnc2-c2cc(-c3cnn(C4CCOCC4)c3)cnc2N)c(F)c1F]
32 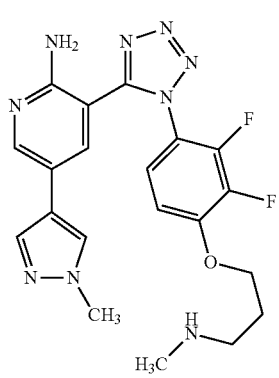 [SMILES: CNCCCOc1ccc(-n2nnnc2-c2cc(-c3cnn(C)c3)cnc2N)c(F)c1F]
33 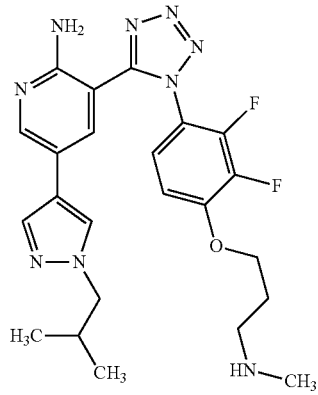 [SMILES: CNCCCOc1ccc(-n2nnnc2-c2cc(-c3cnn(CC(C)C)c3)cnc2N)c(F)c1F]
34 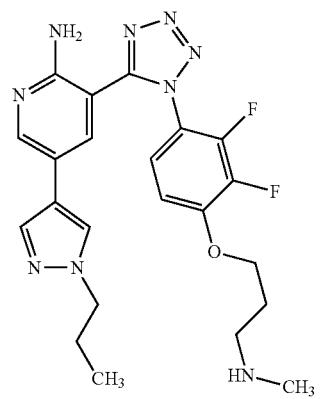 [SMILES: CCCn1cc(-c2cnc(N)c(-c3nnnn3-c3ccc(OCCCNC)c(F)c3F)c2)cn1]
35 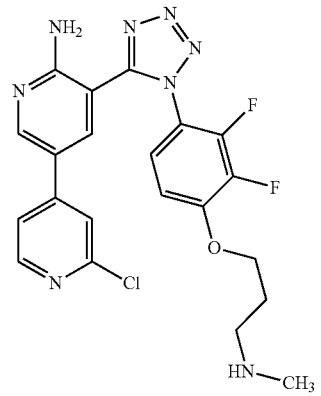 [SMILES: CNCCCOc1ccc(-n2nnnc2-c2cc(-c3ccnc(Cl)c3)cnc2N)c(F)c1F]

TABLE 1-continued
Compounds of Formula I
| | |
|---|---|
| 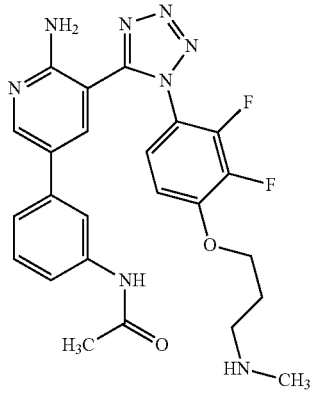 [SMILES: CNCCCOc1ccc(-n2nnnc2-c2cc(-c3cccc(NC(C)=O)c3)cnc2N)c(F)c1F] 36 | 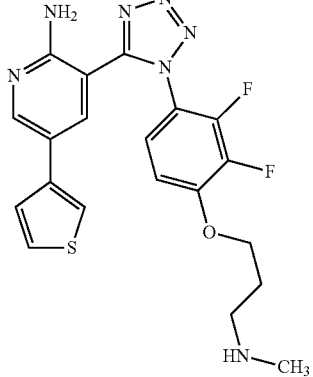 39 |
| 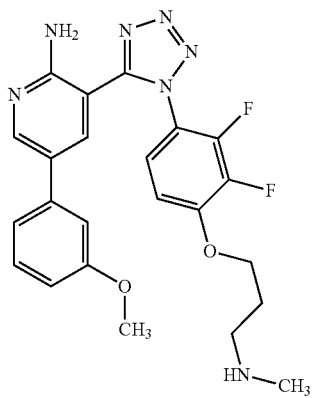 [SMILES: CNCCCOc1ccc(-n2nnnc2-c2cc(-c3cccc(OC)c3)cnc2N)c(F)c1F] 37 | 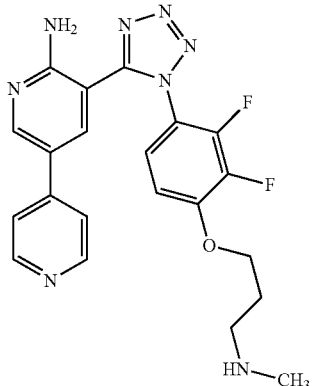 40 |
| | 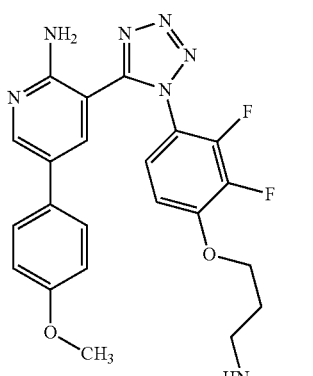 41 |
| 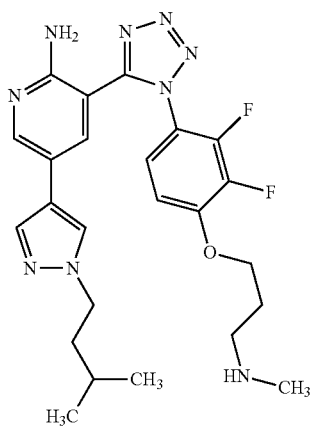 [SMILES: CNCCCOc1ccc(-n2nnnc2-c2cc(-c3cnn(CCC(C)C)c3)cnc2N)c(F)c1F] 38 | 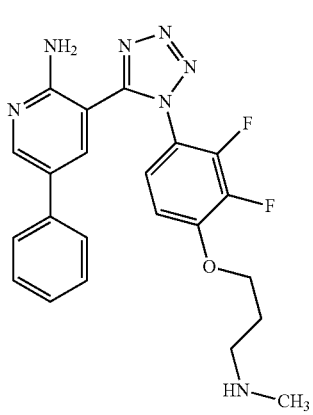 [SMILES: CNCCCOc1ccc(-n2nnnc2-c2cc(-c3ccccc3)cnc2N)c(F)c1F] 42 |

TABLE 1-continued
Compounds of Formula I
43
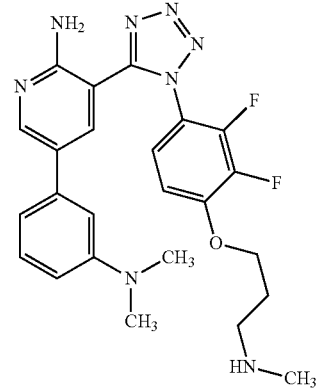 [SMILES: CNCCCOc1ccc(-n2nnnc2-c2cc(-c3cccc(N(C)C)c3)cnc2N)c(F)c1F]
44
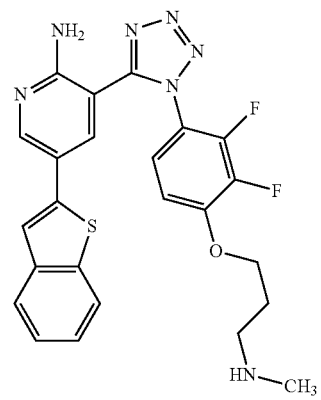 [SMILES: CNCCCOc1ccc(-n2nnnc2-c2cc(-c3cc4ccccc4s3)cnc2N)c(F)c1F]
45
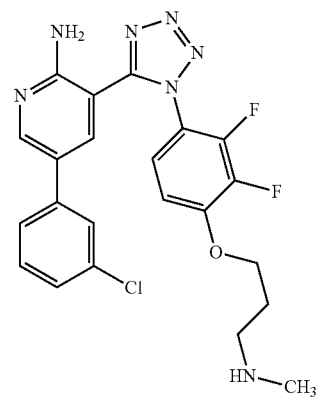
46
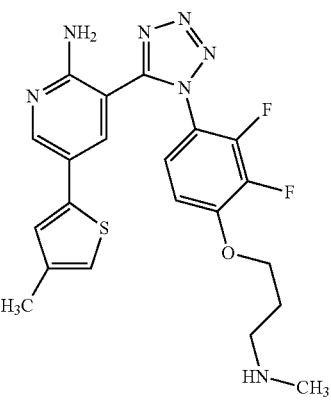
TABLE 1-continued
Compounds of Formula I
47
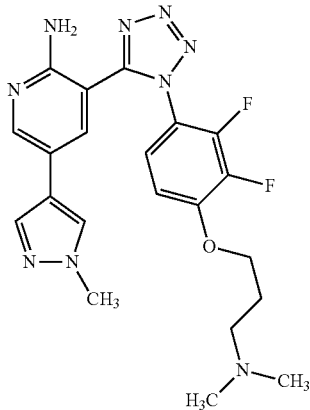 [SMILES: CN(C)CCCOc1ccc(-n2nnnc2-c2cc(-c3cnn(C)c3)cnc2N)c(F)c1F]
48
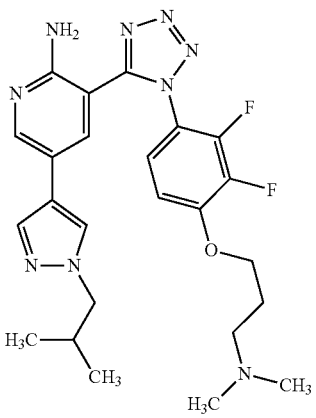 [SMILES: CC(C)Cn1cc(-c2cnc(N)c(-c3nnnn3-c3ccc(OCCCN(C)C)c(F)c3F)c2)cn1]
49

TABLE 1-continued
Compounds of Formula I
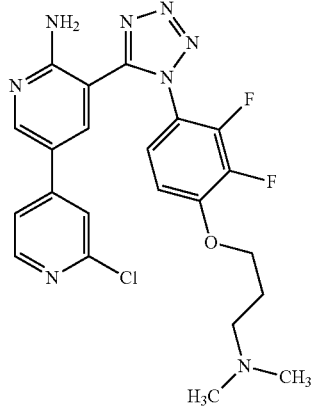 [SMILES: CN(C)CCCOc1ccc(-n2nnnc2-c2cc(-c3ccnc(Cl)c3)cnc2N)c(F)c1F] 50
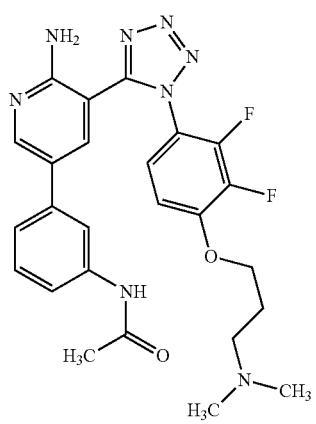 [SMILES: CC(=O)Nc1cccc(-c2cnc(N)c(-c3nnnn3-c3ccc(OCCCN(C)C)c(F)c3F)c2)c1] 51
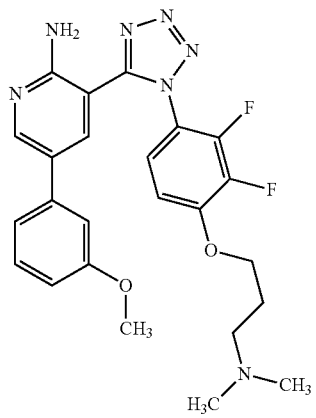 [SMILES: COc1cccc(-c2cnc(N)c(-c3nnnn3-c3ccc(OCCCN(C)C)c(F)c3F)c2)c1] 52
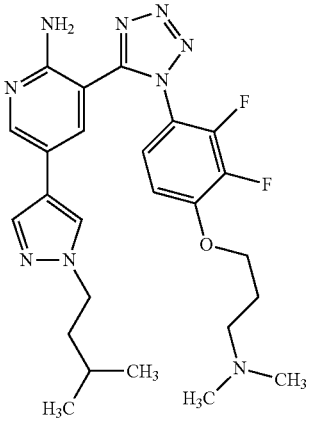 [SMILES: CC(C)CCn1cc(-c2cnc(N)c(-c3nnnn3-c3ccc(OCCCN(C)C)c(F)c3F)c2)cn1] 53
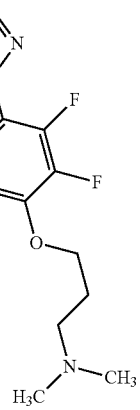
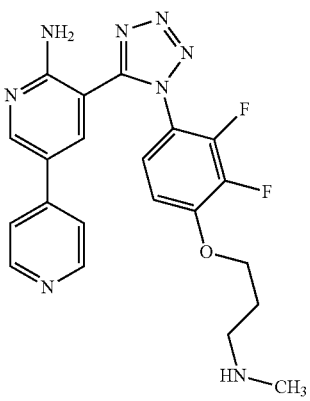 [SMILES: CNCCCOc1ccc(-n2nnnc2-c2cc(-c3ccncc3)cnc2N)c(F)c1F] 54
55

TABLE 1-continued
Compounds of Formula I
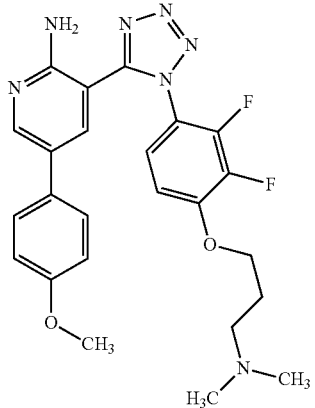 [SMILES: COc1ccc(-c2cnc(N)c(-c3nnnn3-c3ccc(OCCCN(C)C)c(F)c3F)c2)cc1]
56
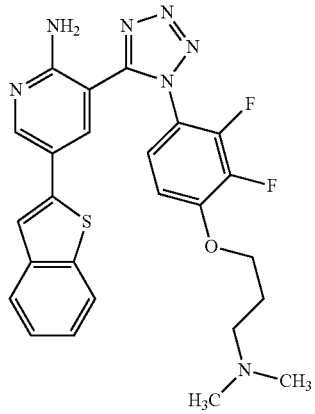
59
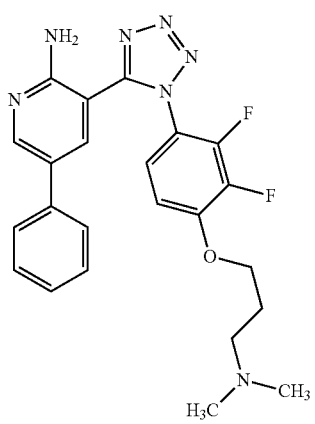 [SMILES: CN(C)CCCOc1ccc(-n2nnnc2-c2cc(-c3ccccc3)cnc2N)c(F)c1F]
57
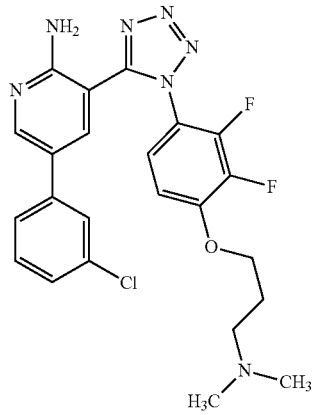
60
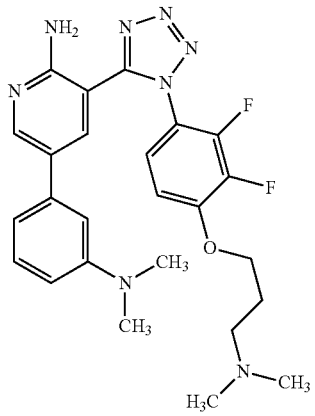 [SMILES: CN(C)CCCOc1ccc(-n2nnnc2-c2cc(-c3cccc(N(C)C)c3)cnc2N)c(F)c1F]
58
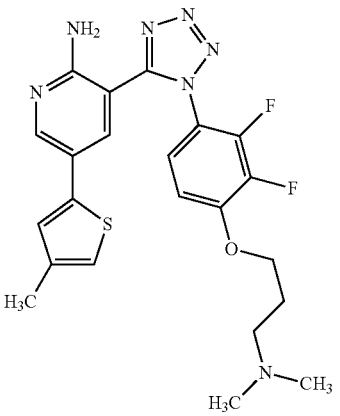
61

TABLE 1-continued
Compounds of Formula I
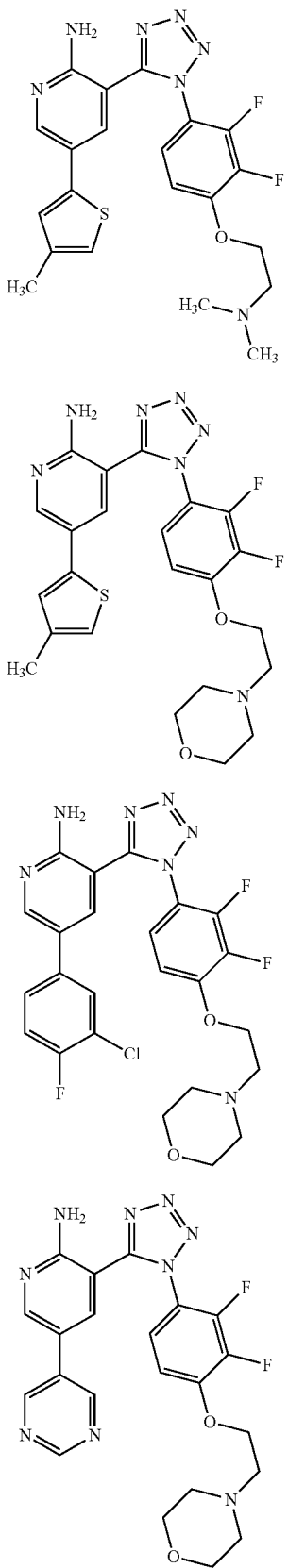
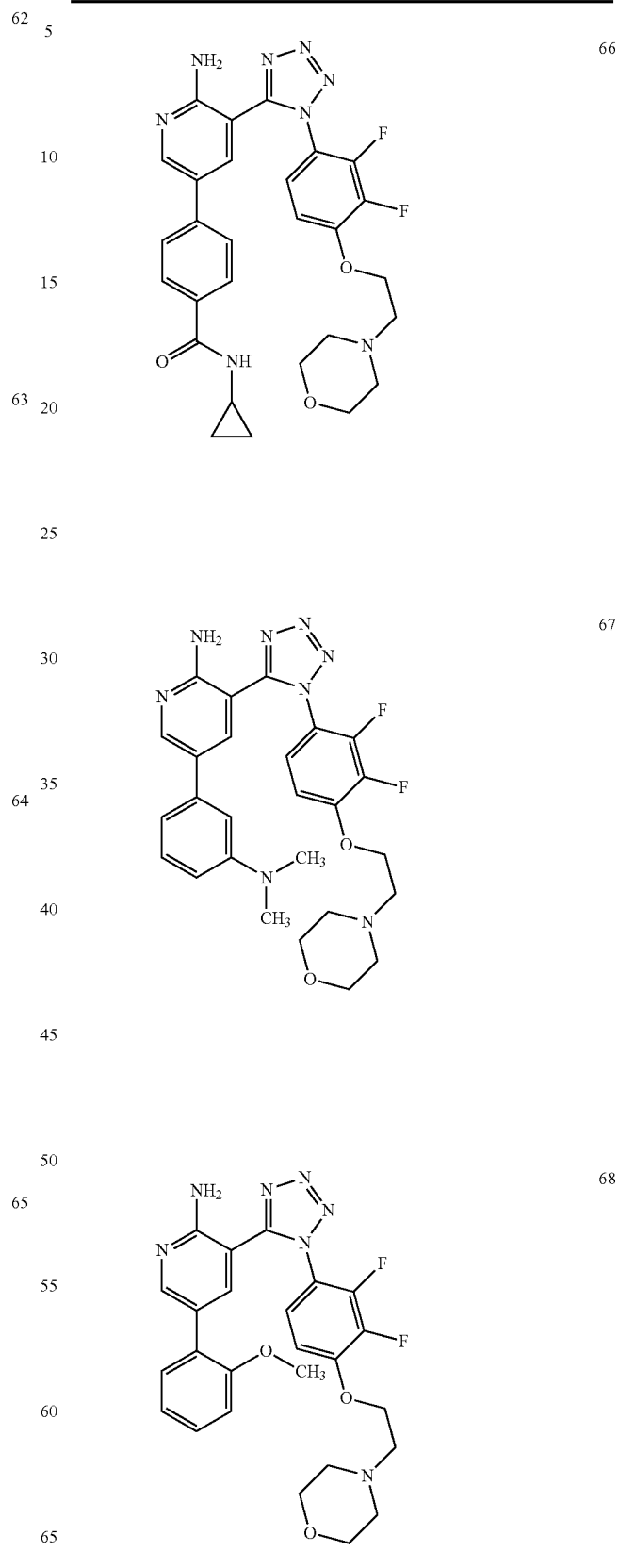

TABLE 1-continued
Compounds of Formula I
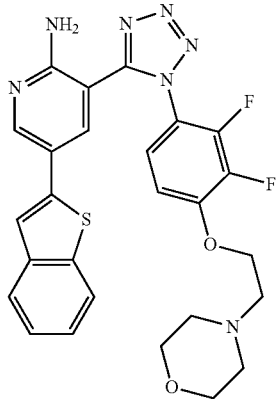 [SMILES: Nc1ncc(-c2cc3ccccc3s2)cc1-c1nnnn1-c1ccc(OCCN2CCOCC2)c(F)c1F]
69
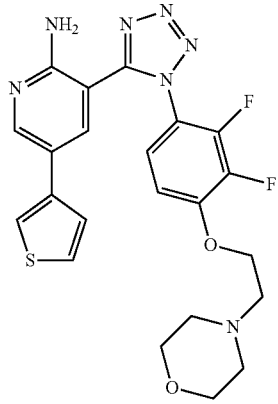
72
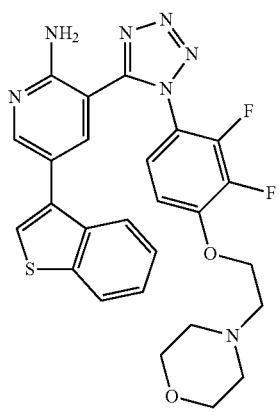 [SMILES: Nc1ncc(-c2csc3ccccc23)cc1-c1nnnn1-c1ccc(OCCN2CCOCC2)c(F)c1F]
70
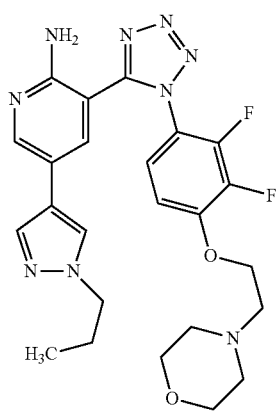
73
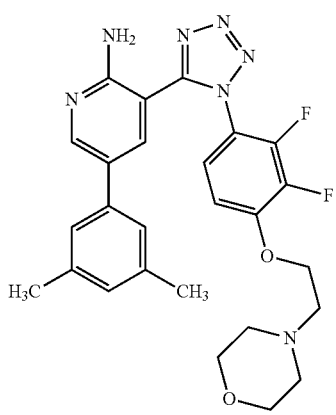 [SMILES: Cc1cc(C)cc(-c2cnc(N)c(-c3nnnn3-c3ccc(OCCN4CCOCC4)c(F)c3F)c2)c1]
71
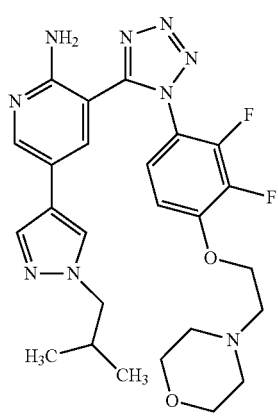
74

TABLE 1-continued
Compounds of Formula I
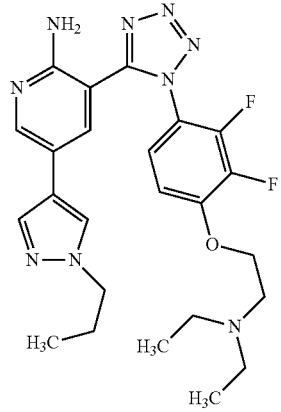 [SMILES: CCCn1cc(-c2cnc(N)c(-c3nnnn3-c3ccc(OCCN(CC)CC)c(F)c3F)c2)cn1]
75
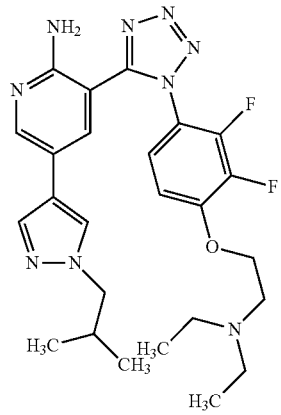 [SMILES: CCN(CC)CCOc1ccc(-n2nnnc2-c2cc(-c3cnn(CC(C)C)c3)cnc2N)c(F)c1F]
76
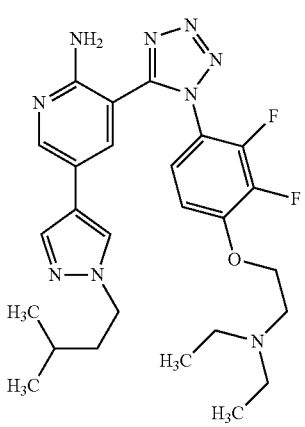 [SMILES: CCN(CC)CCOc1ccc(-n2nnnc2-c2cc(-c3cnn(CCC(C)C)c3)cnc2N)c(F)c1F]
77
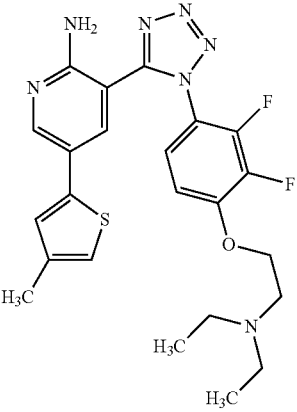 [SMILES: CCN(CC)CCOc1ccc(-n2nnnc2-c2cc(-c3cc(C)cs3)cnc2N)c(F)c1F]
78
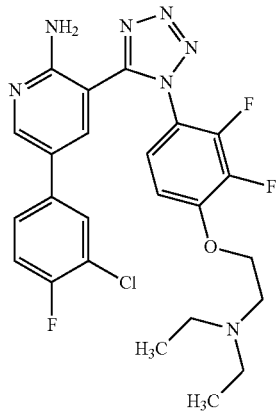 [SMILES: CCN(CC)CCOc1ccc(-n2nnnc2-c2cc(-c3ccc(F)c(Cl)c3)cnc2N)c(F)c1F]
79
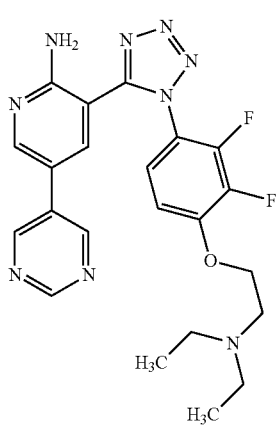 [SMILES: CCN(CC)CCOc1ccc(-n2nnnc2-c2cc(-c3cncnc3)cnc2N)c(F)c1F]
80

TABLE 1-continued
Compounds of Formula I
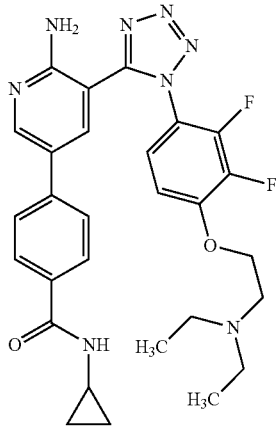 [SMILES: CCN(CC)CCOc1ccc(-n2nnnc2-c2cc(-c3ccc(C(=O)NC4CC4)cc3)cnc2N)c(F)c1F]
81
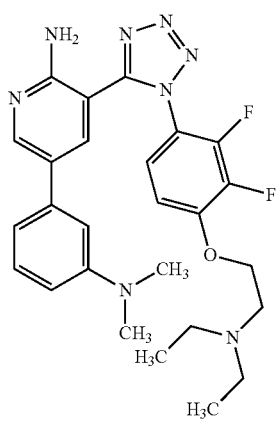 [SMILES: CCN(CC)CCOc1ccc(-n2nnnc2-c2cc(-c3cccc(N(C)C)c3)cnc2N)c(F)c1F]
82
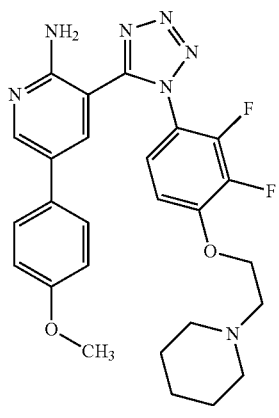 [SMILES: COc1ccc(-c2cnc(N)c(-c3nnnn3-c3ccc(OCCN4CCCCC4)c(F)c3F)c2)cc1]
83
TABLE 1-continued
Compounds of Formula I
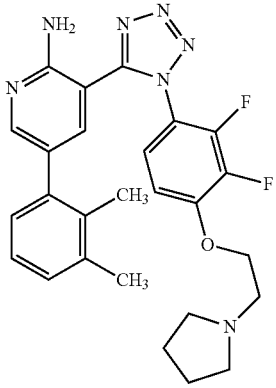 [SMILES: Cc1cccc(-c2cnc(N)c(-c3nnnn3-c3ccc(OCCN4CCCC4)c(F)c3F)c2)c1C]
84
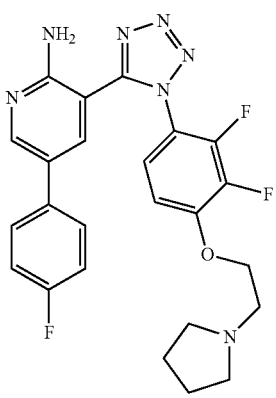
85
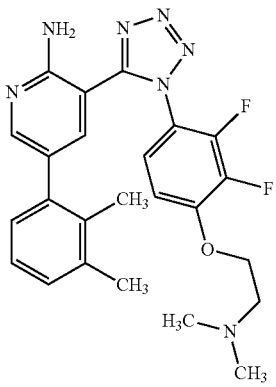 [SMILES: Cc1cccc(-c2cnc(N)c(-c3nnnn3-c3ccc(OCCN(C)C)c(F)c3F)c2)c1C]
86
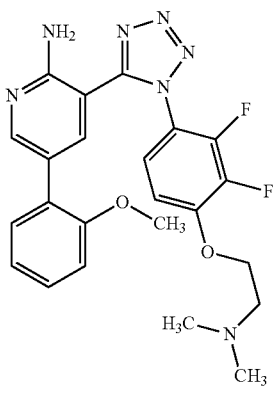 [SMILES: COc1ccccc1-c1cnc(N)c(-c2nnnn2-c2ccc(OCCN(C)C)c(F)c2F)c1]
87

TABLE 1-continued
Compounds of Formula I
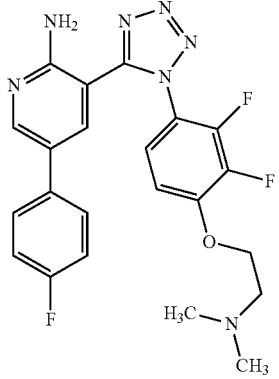 [SMILES: CN(C)CCOc1ccc(-n2nnnc2-c2cc(-c3ccc(F)cc3)cnc2N)c(F)c1F]
88
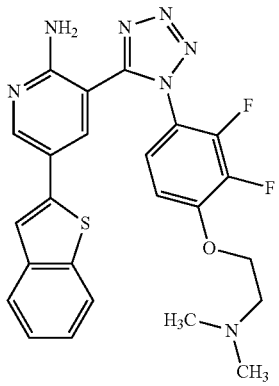 [SMILES: CN(C)CCOc1ccc(-n2nnnc2-c2cc(-c3cc4ccccc4s3)cnc2N)c(F)c1F]
89
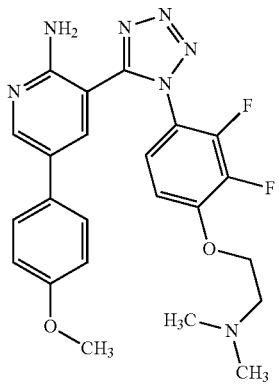 [SMILES: COc1ccc(-c2cnc(N)c(-c3nnnn3-c3ccc(OCCN(C)C)c(F)c3F)c2)cc1]
90
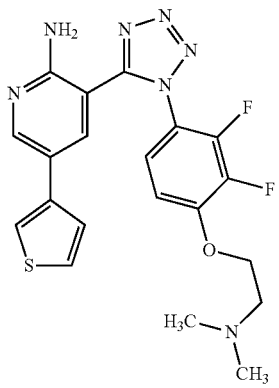 [SMILES: CN(C)CCOc1ccc(-n2nnnc2-c2cc(-c3ccsc3)cnc2N)c(F)c1F]
91
TABLE 1-continued
Compounds of Formula I
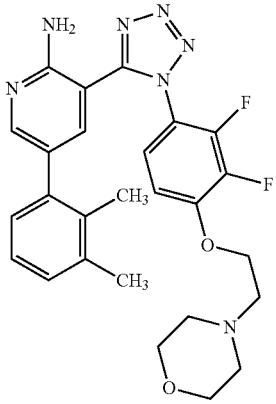 [SMILES: Cc1cccc(-c2cnc(N)c(-c3nnnn3-c3ccc(OCCN4CCOCC4)c(F)c3F)c2)c1C]
92
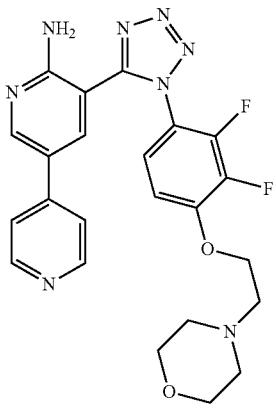
93
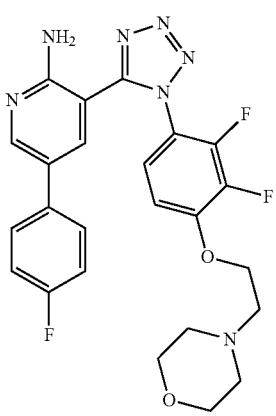 [SMILES: Nc1ncc(-c2ccc(F)cc2)cc1-c1nnnn1-c1ccc(OCCN2CCOCC2)c(F)c1F]
94

TABLE 1-continued
Compounds of Formula I
95 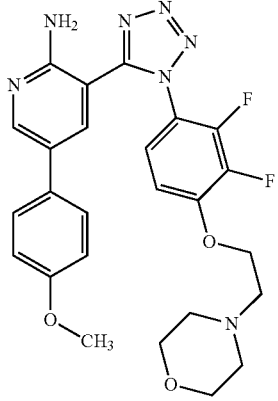 [SMILES: COc1ccc(-c2cnc(N)c(-c3nnnn3-c3ccc(OCCN4CCOCC4)c(F)c3F)c2)cc1]
96 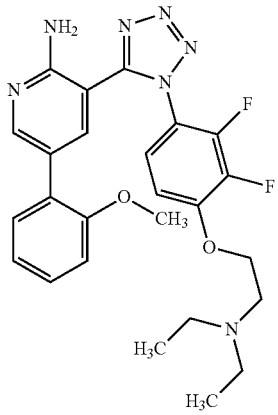 [SMILES: CCN(CC)CCOc1ccc(-n2nnnc2-c2cc(-c3ccccc3OC)cnc2N)c(F)c1F]
97 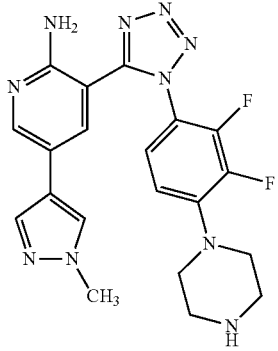 [SMILES: Cn1cc(-c2cnc(N)c(-c3nnnn3-c3ccc(N4CCNCC4)c(F)c3F)c2)cn1]
98 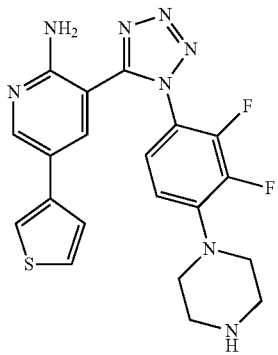 [SMILES: Nc1ncc(-c2ccsc2)cc1-c1nnnn1-c1ccc(N2CCNCC2)c(F)c1F]
TABLE 1-continued
Compounds of Formula I
99 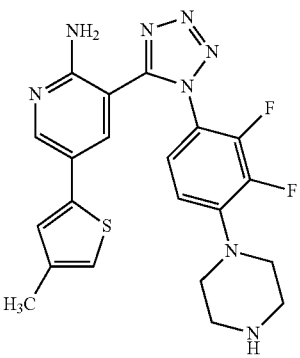 [SMILES: Cc1csc(-c2cnc(N)c(-c3nnnn3-c3ccc(N4CCNCC4)c(F)c3F)c2)c1]
100 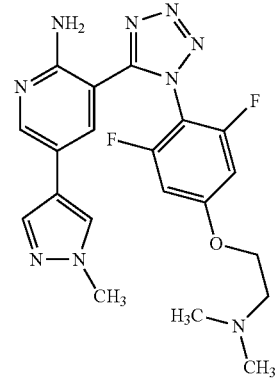 [SMILES: CN(C)CCOc1cc(F)c(-n2nnnc2-c2cc(-c3cnn(C)c3)cnc2N)c(F)c1]
101 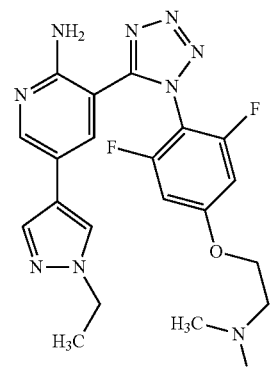
102 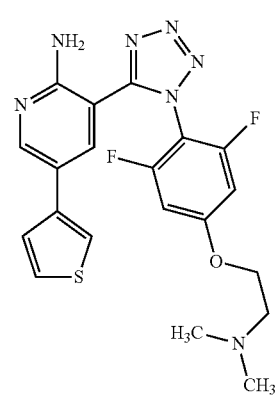 [SMILES: CN(C)CCOc1cc(F)c(-n2nnnc2-c2cc(-c3ccsc3)cnc2N)c(F)c1]

TABLE 1-continued
Compounds of Formula I
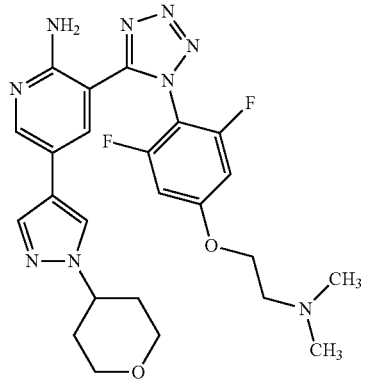 [SMILES: CN(C)CCOc1cc(F)c(-n2nnnc2-c2cc(-c3cnn(C4CCOCC4)c3)cnc2N)c(F)c1] 103
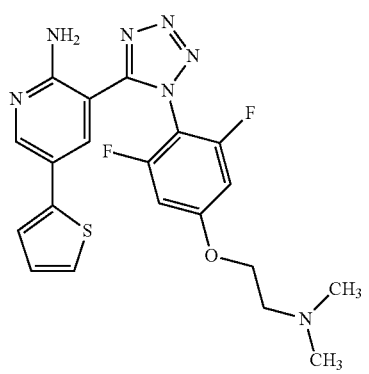 [SMILES: CN(C)CCOc1cc(F)c(-n2nnnc2-c2cc(-c3cccs3)cnc2N)c(F)c1] 104
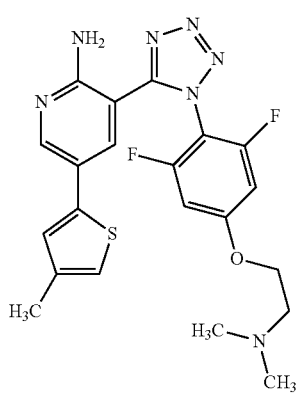 [SMILES: Cc1csc(-c2cnc(N)c(-c3nnnn3-c3c(F)cc(OCCN(C)C)cc3F)c2)c1] 105
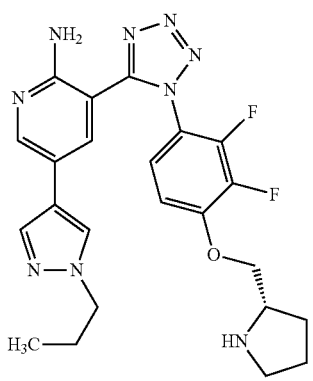 [SMILES: CCCn1cc(-c2cnc(N)c(-c3nnnn3-c3ccc(OC[C@@H]4CCCN4)c(F)c3F)c2)cn1] 106
TABLE 1-continued
Compounds of Formula I
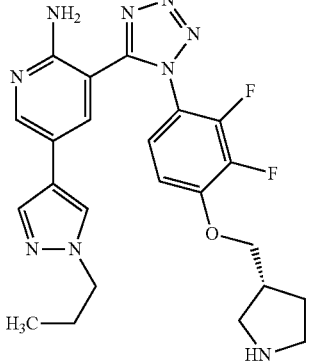 107
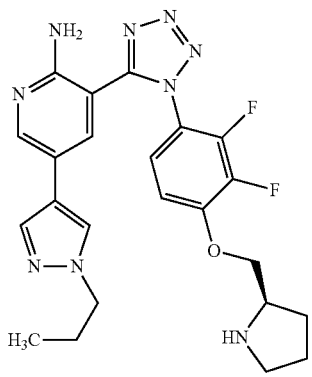 [SMILES: CCCn1cc(-c2cnc(N)c(-c3nnnn3-c3ccc(OC[C@H]4CCCN4)c(F)c3F)c2)cn1] 108
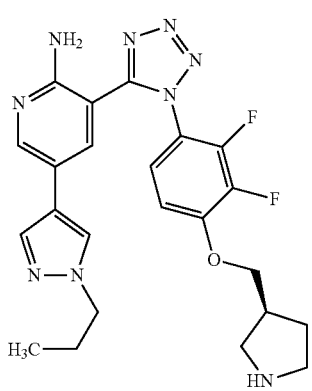 [SMILES: CCCn1cc(-c2cnc(N)c(-c3nnnn3-c3ccc(OC[C@H]4CCNC4)c(F)c3F)c2)cn1] 109
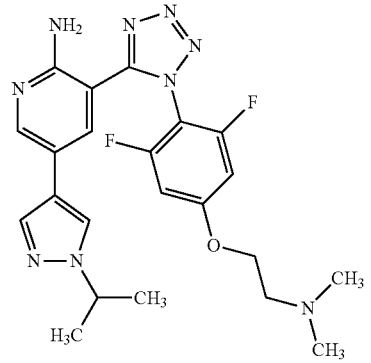 [SMILES: CC(C)n1cc(-c2cnc(N)c(-c3nnnn3-c3c(F)cc(OCCN(C)C)cc3F)c2)cn1] 110

TABLE 1-continued

Compounds of Formula I

TABLE 1-continued
Compounds of Formula I
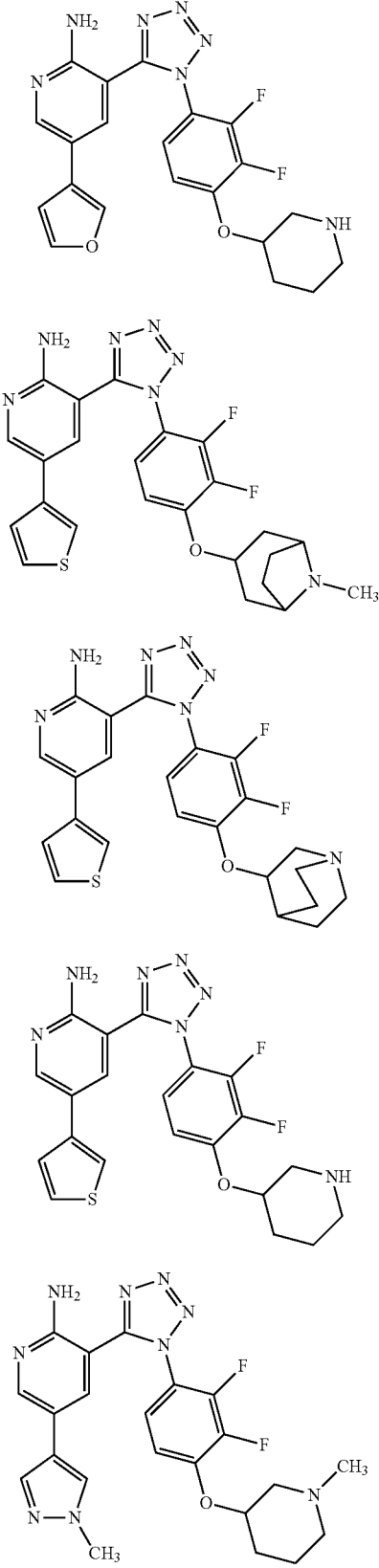
119
120
121
122
123
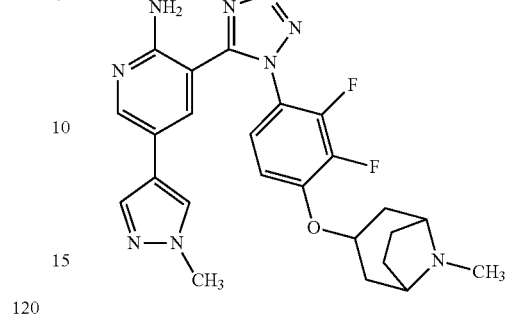
124
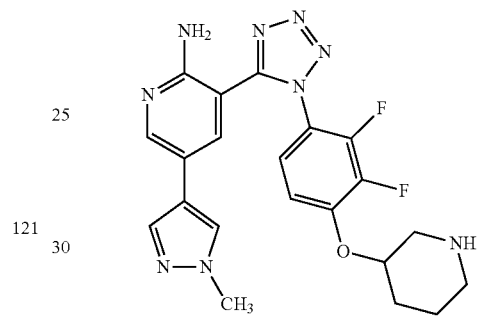
125
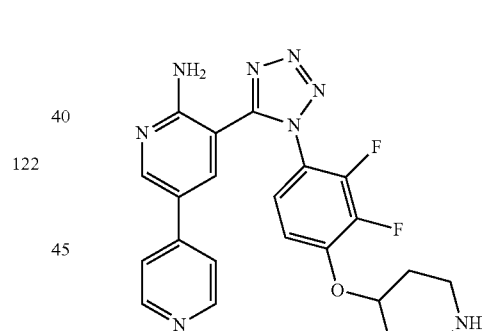
126
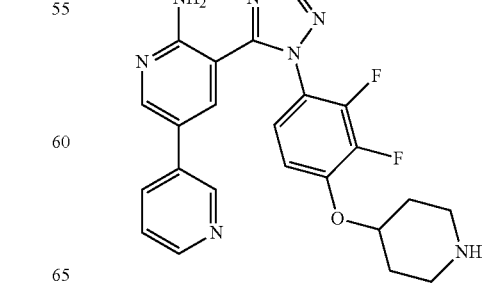
127

TABLE 1-continued
Compounds of Formula I
128 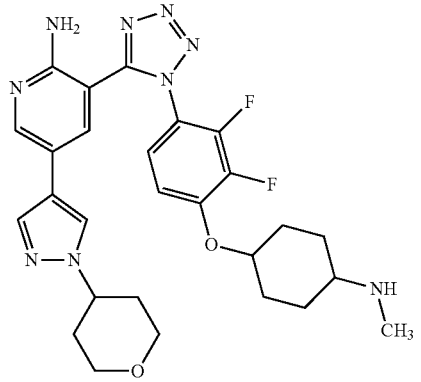 [SMILES: CNC1CCC(Oc2ccc(-n3nnnc3-c3cc(-c4cnn(C5CCOCC5)c4)cnc3N)c(F)c2F)CC1]
129 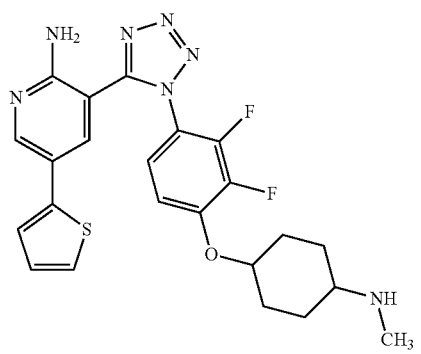 [SMILES: CNC1CCC(Oc2ccc(-n3nnnc3-c3cc(-c4cccs4)cnc3N)c(F)c2F)CC1]
130 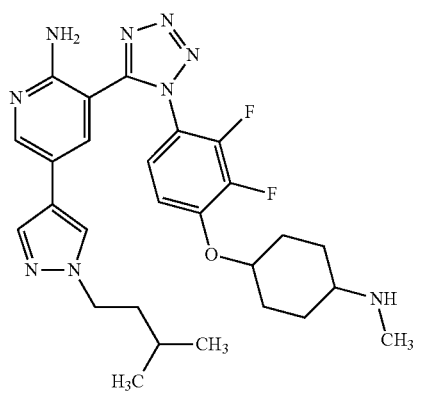 [SMILES: CNC1CCC(Oc2ccc(-n3nnnc3-c3cc(-c4cnn(CCC(C)C)c4)cnc3N)c(F)c2F)CC1]
131 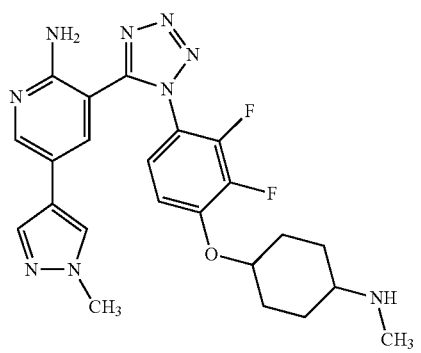 [SMILES: CNC1CCC(Oc2ccc(-n3nnnc3-c3cc(-c4cnn(C)c4)cnc3N)c(F)c2F)CC1]
TABLE 1-continued
Compounds of Formula I
132 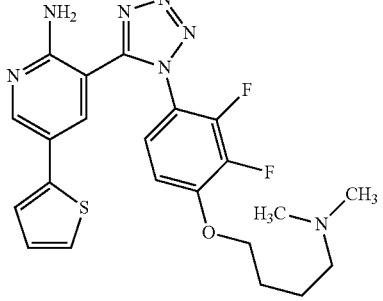
133 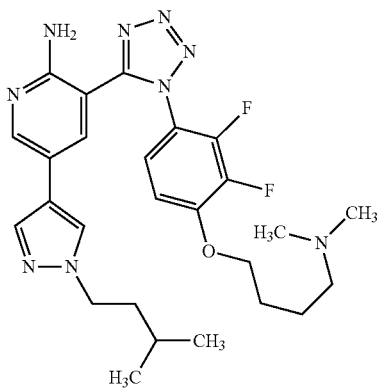 [SMILES: CC(C)CCn1cc(-c2cnc(N)c(-c3nnnn3-c3ccc(OCCCCN(C)C)c(F)c3F)c2)cn1]
134 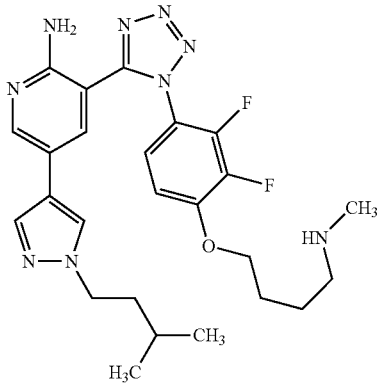 [SMILES: CNCCCCOc1ccc(-n2nnnc2-c2cc(-c3cnn(CCC(C)C)c3)cnc2N)c(F)c1F]
135 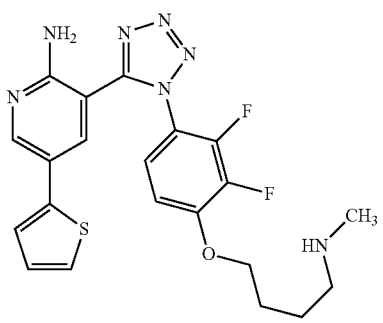 [SMILES: CNCCCCOc1ccc(-n2nnnc2-c2cc(-c3cccs3)cnc2N)c(F)c1F]

TABLE 1-continued
Compounds of Formula I
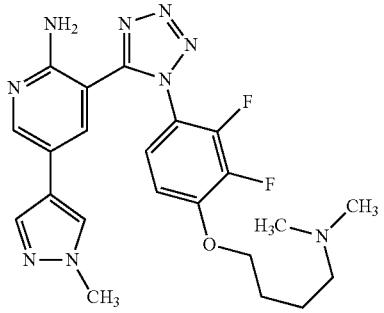 [SMILES: CN(C)CCCCOc1ccc(-n2nnnc2-c2cc(-c3cnn(C)c3)cnc2N)c(F)c1F]
136
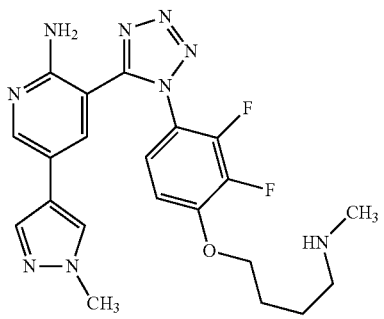 [SMILES: CNCCCCOc1ccc(-n2nnnc2-c2cc(-c3cnn(C)c3)cnc2N)c(F)c1F]
137
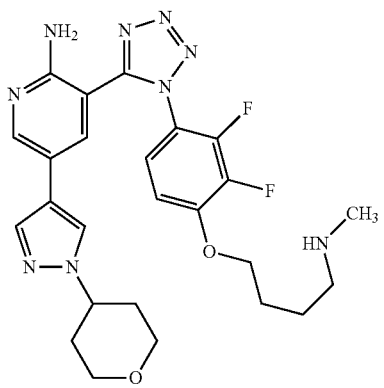 [SMILES: CNCCCCOc1ccc(-n2nnnc2-c2cc(-c3cnn(C4CCOCC4)c3)cnc2N)c(F)c1F]
138
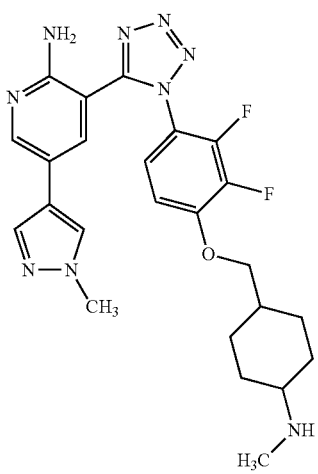 [SMILES: CNC1CCC(COc2ccc(-n3nnnc3-c3cc(-c4cnn(C)c4)cnc3N)c(F)c2F)CC1]
139
TABLE 1-continued
Compounds of Formula I
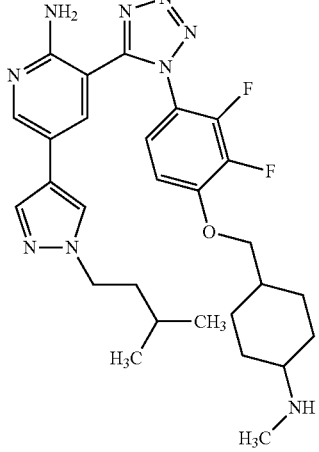
140
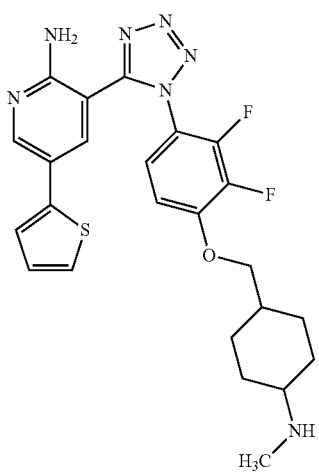 [SMILES: CNC1CCC(COc2ccc(-n3nnnc3-c3cc(-c4cccs4)cnc3N)c(F)c2F)CC1]
141
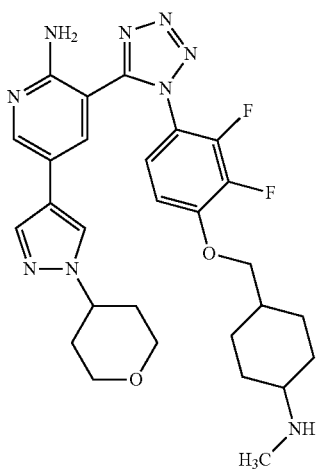 [SMILES: CNC1CCC(COc2ccc(-n3nnnc3-c3cc(-c4cnn(C5CCOCC5)c4)cnc3N)c(F)c2F)CC1]
142

TABLE 1-continued
Compounds of Formula I
143
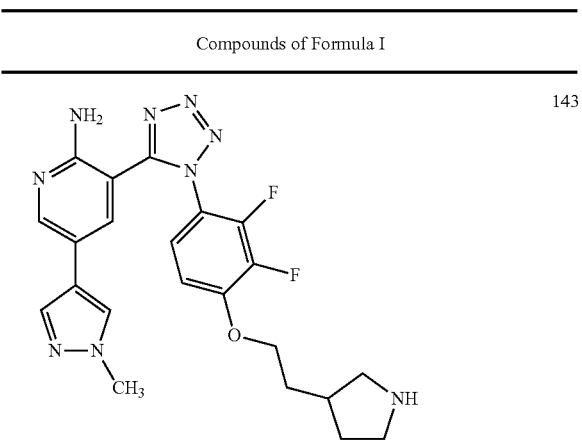
144
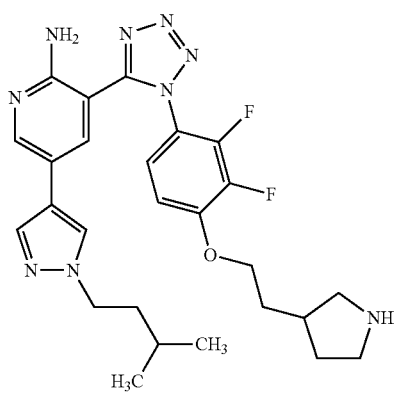 [SMILES: CC(C)CCn1cc(-c2cnc(N)c(-c3nnnn3-c3ccc(OCCC4CCNC4)c(F)c3F)c2)cn1]
145
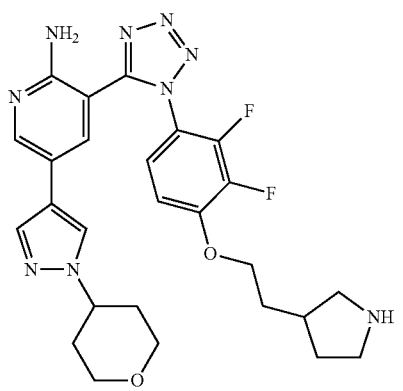 [SMILES: Nc1ncc(-c2cnn(C3CCOCC3)c2)cc1-c1nnnn1-c1ccc(OCCC2CCNC2)c(F)c1F]
146
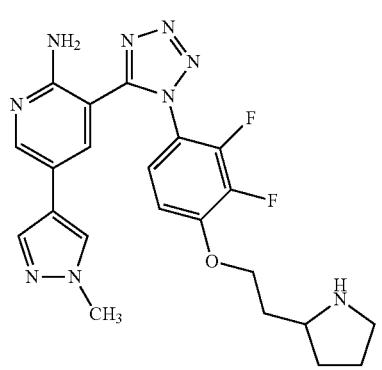 [SMILES: Cn1cc(-c2cnc(N)c(-c3nnnn3-c3ccc(OCCC4CCCN4)c(F)c3F)c2)cn1]
TABLE 1-continued
Compounds of Formula I
147
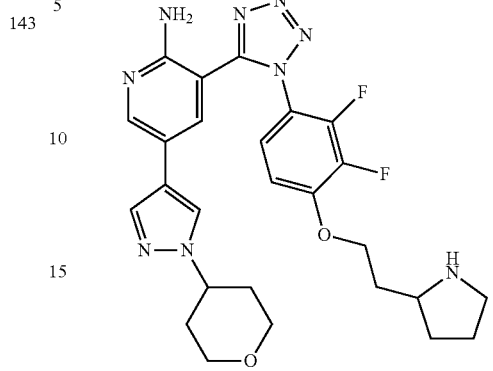
148
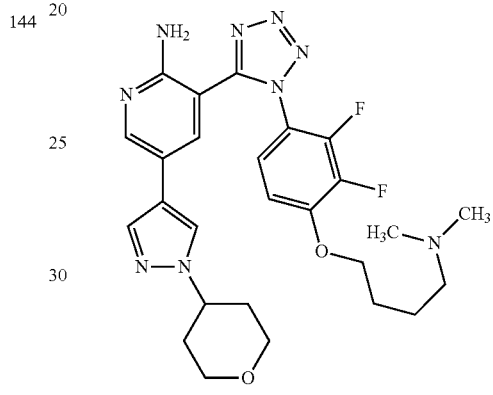
149
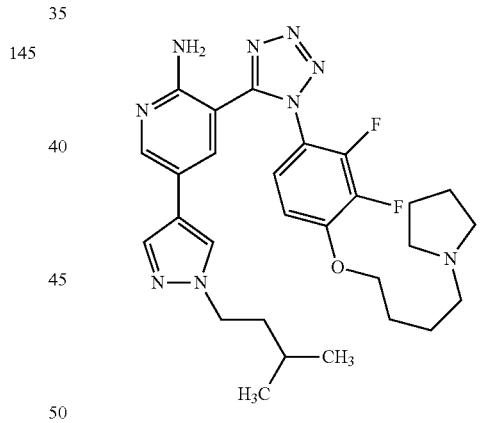
150
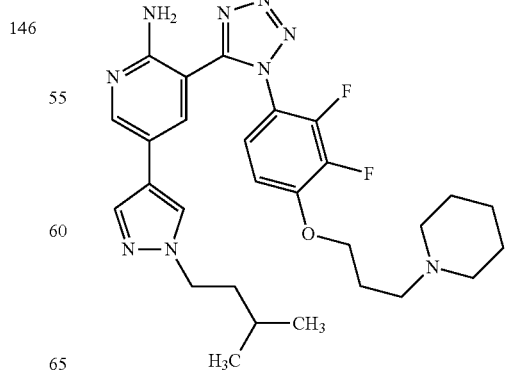

TABLE 1-continued
Compounds of Formula I
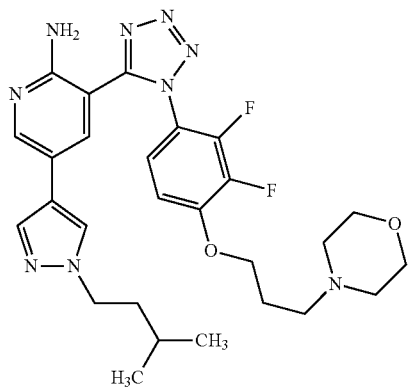 [SMILES: CC(C)CCn1cc(-c2cnc(N)c(-c3nnnn3-c3ccc(OCCCN4CCCCC4)c(F)c3F)c2)cn1]
151
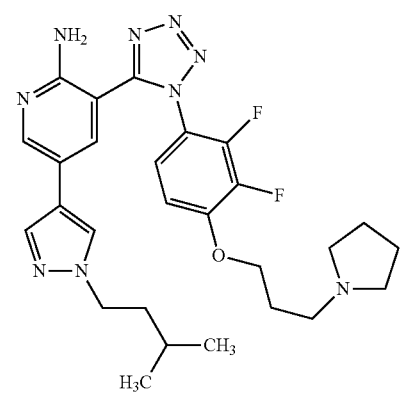 [SMILES: CC(C)CCn1cc(-c2cnc(N)c(-c3nnnn3-c3ccc(OCCCN4CCCC4)c(F)c3F)c2)cn1]
152
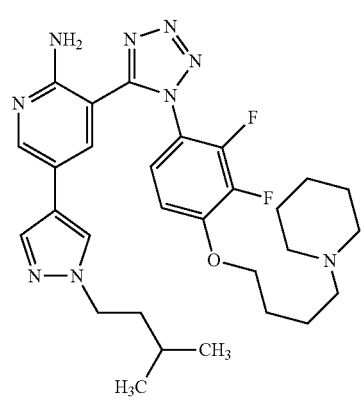
153
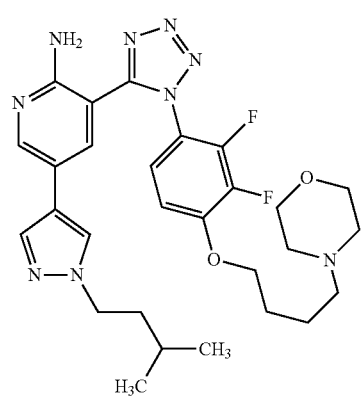 [SMILES: CC(C)CCn1cc(-c2cnc(N)c(-c3nnnn3-c3ccc(OCCCCN4CCOCC4)c(F)c3F)c2)cn1]
154
TABLE 1-continued
Compounds of Formula I
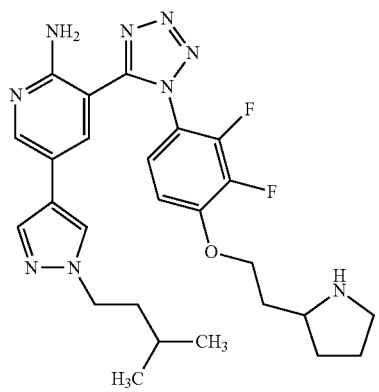 [SMILES: CC(C)CCn1cc(-c2cnc(N)c(-c3nnnn3-c3ccc(OCCC4CCCN4)c(F)c3F)c2)cn1]
155
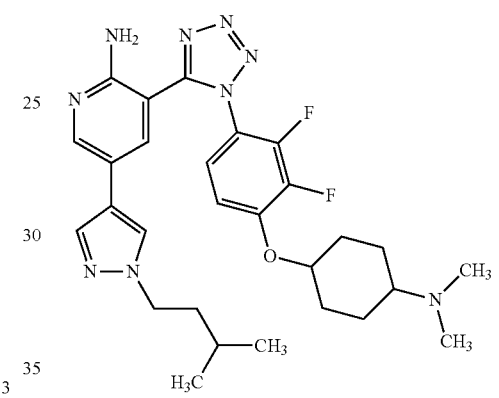
156
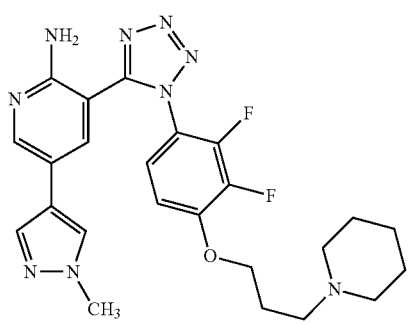 [SMILES: Cn1cc(-c2cnc(N)c(-c3nnnn3-c3ccc(OCCCN4CCCCC4)c(F)c3F)c2)cn1]
157
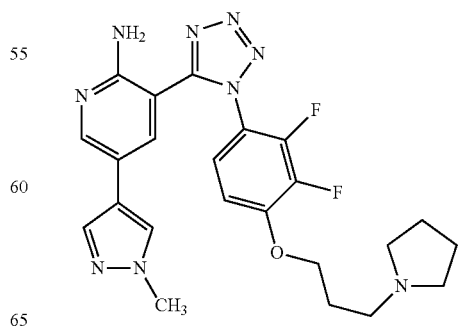
158

TABLE 1-continued
Compounds of Formula I
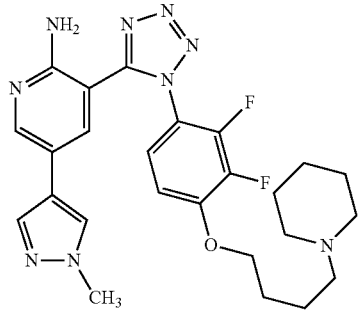 [SMILES: Cn1cc(-c2cnc(N)c(-c3nnnn3-c3ccc(OCCCCN4CCCCC4)c(F)c3F)c2)cn1]
159
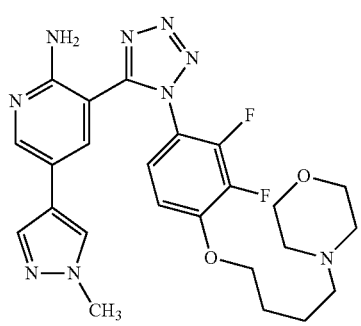 [SMILES: Cn1cc(-c2cnc(N)c(-c3nnnn3-c3ccc(OCCCCN4CCOCC4)c(F)c3F)c2)cn1]
160
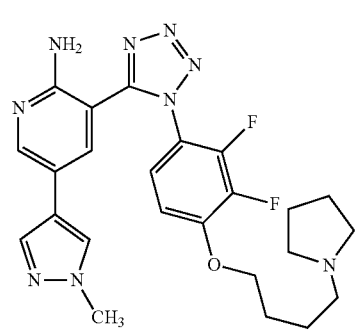 [SMILES: Cn1cc(-c2cnc(N)c(-c3nnnn3-c3ccc(OCCCCN4CCCC4)c(F)c3F)c2)cn1]
161
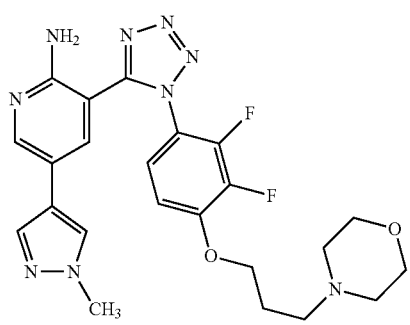 [SMILES: Cn1cc(-c2cnc(N)c(-c3nnnn3-c3ccc(OCCCN4CCOCC4)c(F)c3F)c2)cn1]
162
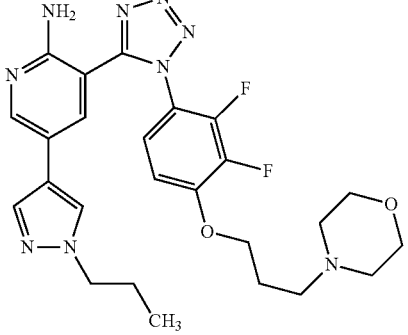
163
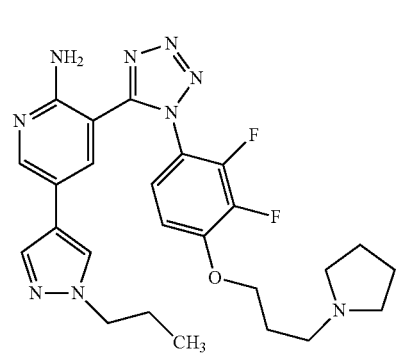 [SMILES: CCCn1cc(-c2cnc(N)c(-c3nnnn3-c3ccc(OCCCN4CCCC4)c(F)c3F)c2)cn1]
164
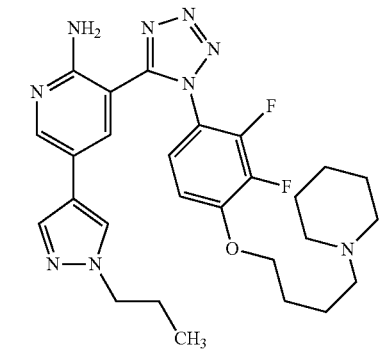 [SMILES: CCCn1cc(-c2cnc(N)c(-c3nnnn3-c3ccc(OCCCCN4CCCCC4)c(F)c3F)c2)cn1]
165
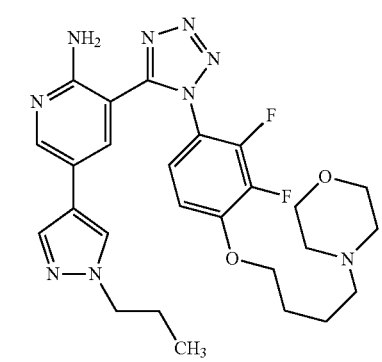 [SMILES: CCCn1cc(-c2cnc(N)c(-c3nnnn3-c3ccc(OCCCCN4CCOCC4)c(F)c3F)c2)cn1]
166

TABLE 1-continued
Compounds of Formula I
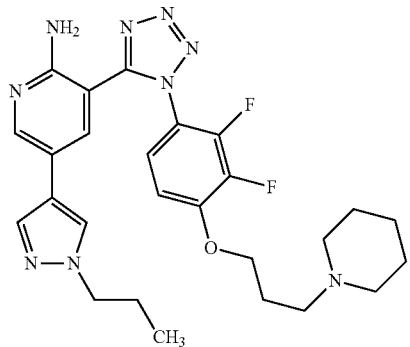
167
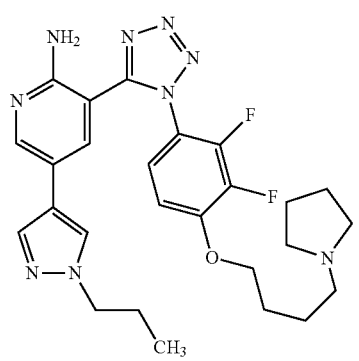 [SMILES: CCCn1cc(-c2cnc(N)c(-c3nnnn3-c3ccc(OCCCCN4CCCC4)c(F)c3F)c2)cn1]
168
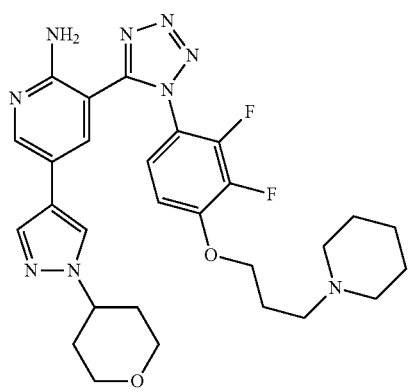 [SMILES: Nc1ncc(-c2cnn(C3CCOCC3)c2)cc1-c1nnnn1-c1ccc(OCCCN2CCCCC2)c(F)c1F]
169
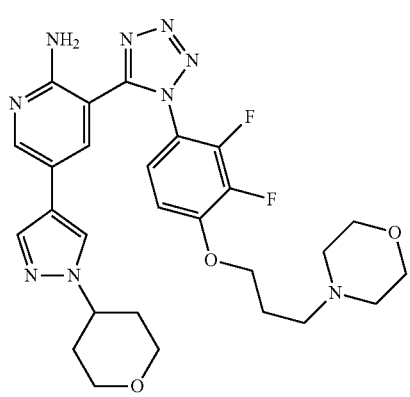 [SMILES: Nc1ncc(-c2cnn(C3CCOCC3)c2)cc1-c1nnnn1-c1ccc(OCCCN2CCOCC2)c(F)c1F]
170
TABLE 1-continued
Compounds of Formula I
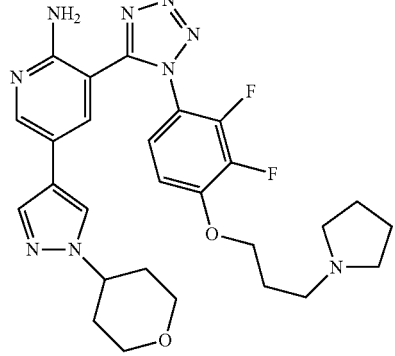
171
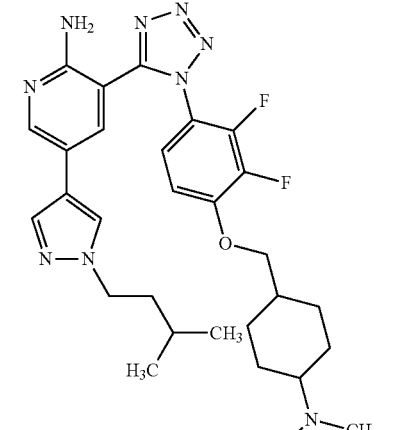
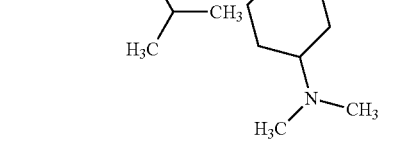
172
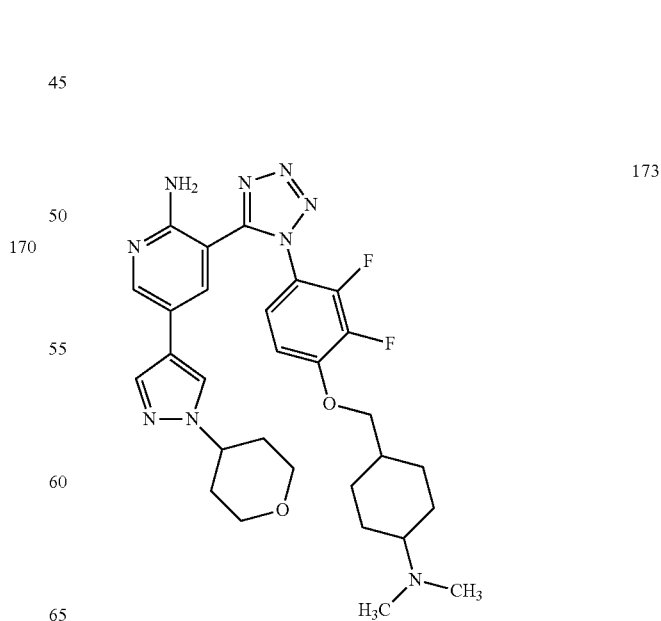
173

TABLE 1-continued

Compounds of Formula I

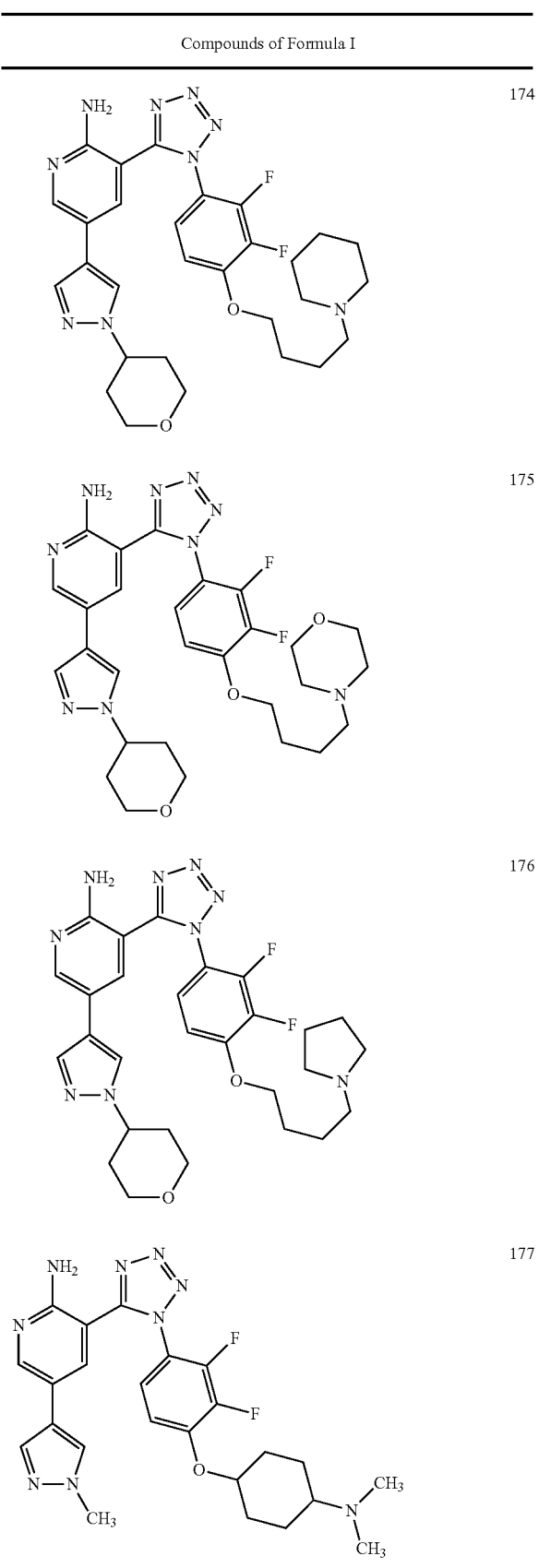

174

175

176

177

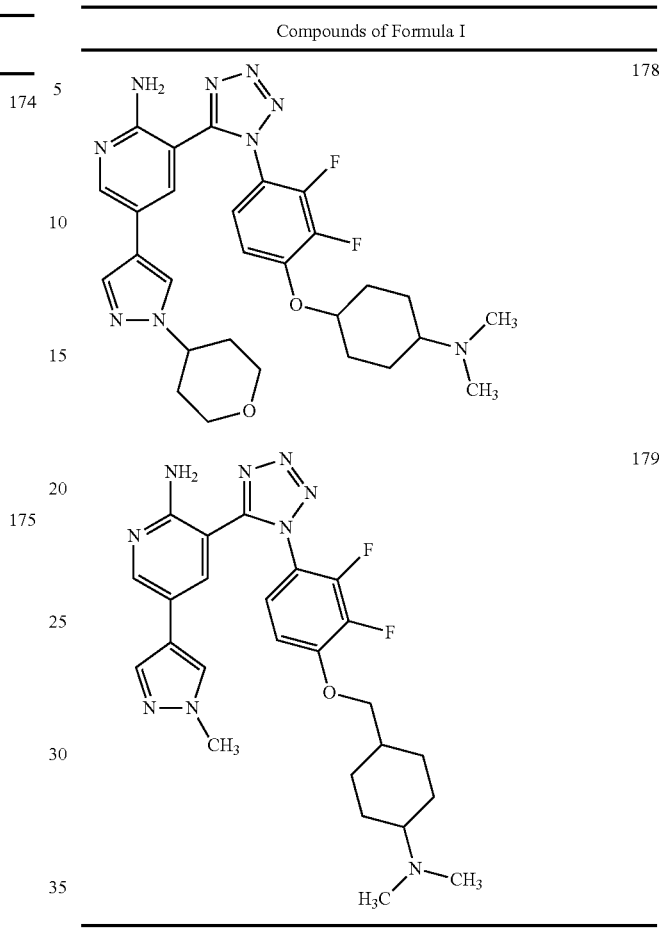

178

179

Compositions, Formulations, and Administration of Compounds of the Invention

In another aspect, the invention provides a pharmaceutical composition comprising a compound of any of the formulae or classes described herein. In a further embodiment, the invention provides a pharmaceutical composition comprising a compound of Table 1. In a further embodiment, a composition of the invention comprises an additional therapeutic agent.

According to another embodiment, the invention provides a composition comprising a compound of this invention or a pharmaceutically acceptable derivative thereof and a pharmaceutically acceptable carrier, adjuvant, or vehicle. In one embodiment, the amount of compound in a composition of this invention is such that is effective to measurably inhibit c-MET in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like.

Pharmaceutically acceptable salts are well known in the art. For example, S. M. Berge et al., describe pharmaceutically acceptable salts in detail in *J. Pharmaceutical Sciences*, 66:1-19, 1977, which is incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: *The Science and Practice of Pharmacy*, 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, dissolving or suspending the compound in an oil vehicle accomplishes delayed absorption of a parenterally administered compound form. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated." Examples of additional therapeutic agents are provided infra.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Uses of the Compounds and Compositions of the Invention

According to one embodiment, the invention relates to a method of inhibiting c-MET protein kinase activity in a biological sample comprising the step of contacting said biological sample with a compound of this invention, or a composition comprising said compound. The term "biological sample," as used herein, means a sample outside a living organism and includes, without limitation, cell cultures or extracts thereof; biopsied material obtained from a mammal or extracts thereof; and blood, saliva, urine, feces, semen, tears, or other body fluids or extracts thereof. Inhibition of kinase activity in a biological sample is useful for a variety of purposes known to one of skill in the art. Examples of such purposes include, but are not limited to, biological specimen storage and biological assays. In one embodiment, the method of inhibiting kinase activity in a biological sample is limited to non-therapeutic methods.

The term "c-MET" is synonymous with "c-Met," "cMet", "MET", "Met" or other designations known to one skilled in the art.

According to another embodiment, the invention relates to a method of inhibiting c-MET kinase activity in a patient comprising the step of administering to said patient a compound of the present invention, or a composition comprising said compound.

The term "c-MET-mediated disease" or "c-MET-mediated condition", as used herein, means any disease state or other deleterious condition in which c-MET is known to play a role. The terms "c-MET-mediated disease" or "c-MET-mediated condition" also mean those diseases or conditions that are alleviated by treatment with a c-MET inhibitor. Such conditions include, without limitation, renal, gastric, colon, brain, breast, prostate, and lung cancer, glioblastoma, atherosclerosis, lung fibrosis, conditions associated with organ transplantation, allergic disorders, and autoimmune disorders.

In one aspect, the present invention features a method treating a proliferative disorder in a patient comprising the step of administering to the patient a therapeutically effective dose of any of the compounds or compositions of the invention.

According to one embodiment, the proliferative disorder is cancer, such as, for example, renal, gastric, colon, brain, breast, liver, prostate, and lung cancer, or a glioblastoma.

In another embodiment, the present invention relates to a method of treating or lessening the severity of brain cancer in a patient in need thereof, comprising administering to said patient a compound of the present invention or composition thereof.

In another embodiment, the proliferative disorder is polycythemia vera, essential thrombocythemia, chronic idiopathic myelofibrosis, myeloid metaplasia with myelofibrosis, chronic myeloid leukemia (CML), chronic myelomonocytic leukemia, chronic eosinophilic leukemia, hypereosinophilic syndrome, systematic mast cell disease, atypical CML, or juvenile myelomonocytic leukemia.

In another embodiment, the proliferative disorder is atherosclerosis or lung fibrosis.

Another aspect of the present invention relates to a method of inhibiting tumor metastasis in a patient in need thereof, comprising administering to said patient a compound of the present invention or composition thereof.

Depending upon the particular condition, or disease, to be treated, additional therapeutic agents, which are normally administered to treat that condition, may also be present in the compositions of this invention. As used herein, additional therapeutic agents that are normally administered to treat a particular disease, or condition, are known as "appropriate for the disease, or condition, being treated".

In one embodiment, chemotherapeutic agents or other antiproliferative agents may be combined with the compounds of this invention to treat proliferative diseases and cancer. Examples of known chemotherapeutic agents include, but are not limited to, alkylating agents, such as, for example, cyclophosphamide, lomustine, busulfan procarbazine, ifosfamide, altretamine, melphalan, estramustine phosphate, hexamethylmelamine, mechlorethamine, thiotepa, streptozocin, chlorambucil, temozolomide, dacarbazine, semustine, or carmustine; platinum agents, such as, for example, cisplatin, carboplatinum, oxaliplatin, ZD-0473 (AnorMED), spiroplatinum, lobaplatin (Aeterna), carboxyphthalatoplatinum, satraplatin (Johnson Matthey), tetraplatin BBR-3464, (Hoffmann-La Roche), ormiplatin, SM-11355 (Sumitomo), iproplatin, or AP-5280 (Access); antimetabolites, such as, for example, azacytidine, tomudex, gemcitabine, trimetrexate, capecitabine, deoxycoformycin, 5-fluorouracil, fludarabine, floxuridine, pentostatin, 2-chlorodeoxyadenosine, raltitrexed, 6-mercaptopurine, hydroxyurea, 6-thioguanine, decitabine (SuperGen), cytarabin, clofarabine (Bioenvision), 2-fluorodeoxy cytidine, irofulven (MGI Pharma), methotrexate, DMDC (Hoffmann-La Roche), idatrexate, or ethynylcytidine (Taiho); topoisomerase inhibitors, such as, for example, amsacrine, rubitecan (SuperGen), epirubicin, exatecan mesylate (Daiichi), etoposide, quinamed (ChemGenex), teniposide, mitoxantrone, gimatecan (Sigma-Tau), irinotecan (CPT-11), diflomotecan (Beaufour-Ipsen), 7-ethyl-10-hydroxy-camptothecin, TAS-103 (Taiho), topotecan, elsamitrucin (Spectrum), dexrazoxanet (TopoTarget), J-107088 (Merck & Co), pixantrone (Novuspharma), BNP-1350 (BioNumerik), rebeccamycin analogue (Exelixis), CKD-602 (Chong Kun Dang), BBR-3576 (Novuspharma), or KW-2170 (Kyowa Hakko); antitumor antibiotics, such as, for example, dactinomycin (actinomycin D), amonafide, doxorubicin (adriamycin), azonafide, deoxyrubicin, anthrapyrazole, valrubicin, oxantrazole, daunorubicin (daunomycin), losoxantrone, epirubicin, bleomycin, sulfate (blenoxane), therarubicin, bleomycinic acid, idarubicin, bleomycin A, rubidazone, bleomycin B, plicamycinp, mitomycin C, porfiromycin, MEN-10755 (Menarini), cyanomorpholinodoxorubicin, GPX-100 (Gem Pharmaceuticals), or mitoxantrone (novantrone), antimitotic agents, such as, for example, paclitaxel, SB 408075 (GlaxoSmithKline), docetaxel, E7010 (Abbott), colchicines, PG-TXL (Cell Therapeutics), vinblastine, IDN 5109 (Bayer), vincristine A, 105972 (Abbott), vinorelbine, A 204197 (Abbott), vindesine, LU 223651 (BASF), dolastatin 10 (NCI), D 24851 (ASTAMedica), rhizoxin (Fujisawa), ER-86526 (Eisai), mivobulin (Warner-Lambert), combretastatin A4 (BMS), cemadotin (BASF), isohomohalichondrin-B (PharmaMar), RPR 109881A (Aventis), ZD 6126 (AstraZeneca), TXD 258 (Aventis), PEG-paclitaxel (Enzon,) epothilone B (Novartis), AZ10992 (Asahi), T 900607 (Tularik), IDN-5109 (Indena), T 138067 (Tularik), AVLB (Prescient NeuroPharma), cryptophycin 52 (Eli Lilly), aza-epothilone B (BMS), vinflunine (Fabre), BNP-7787 (BioNumerik), auristatin PE (Teikoku Hormone), CA-4 prodrug (OXiGENE), BMS 247550 (BMS), dolastatin-10 (NIH), BMS 184476 (BMS), CA-4 (OXiGENE), BMS 188797 (BMS), or taxoprexin (Protarga); aromatase inhibitors, such as, for example, aminoglutethimide, exemestane, letrozole, atamestane (BioMedicines), anastrazole, YM-511 (Yamanouchi), or formestane; thymidylate synthase inhibitors, such as, for example, pemetrexed (Eli Lilly), nolatrexed (Eximias), ZD-9331 (BTG), or CoFactor™ (BioKeys); DNA antagonists, such as, for example, trabectedin (PharmaMar), mafosfamide (Baxter International), glufosfamide (Baxter International), apaziquone (Spectrum Pharmaceuticals), albumin+$^{32}$P (Isotope Solutions), O6 benzyl guanine (Paligent), thymectacin (NewBiotics), or edotreotide (Novartis); farnesyltransferase inhibitors, such as, for example, arglabin (NuOncology Labs), tipifarnib (Johnson & Johnson), lonafarnib (Schering-Plough), perillyl alcohol (DOR BioPharma), or BAY-43-9006 (Bayer); Pump inhibitors, such as, for example, CBT-1 (CBA Pharma), zosuquidar trihydrochloride (Eli Lilly), tariquidar (Xenova), biricodar dicitrate (Vertex), or MS-209 (Schering AG); Histone acetyltransferase inhibitors, such as, for example, tacedinaline (Pfizer), pivaloyloxymethyl butyrate (Titan), SAHA (Aton Pharma), depsipeptide (Fujisawa), or MS-275 (Schering AG); Metalloproteinase inhibitors, such as, for example, Neovastat (Aeterna Laboratories), CMT-3 (CollaGenex), marimastat (British Biotech), or BMS-275291 (Celltech); ribonucleoside reductase inhibitors, such as, for example, gallium maltolate (Titan), tezacitabine (Aventis), triapine (Vion), or didox (Molecules for Health); TNF alpha agonists/antagonists, such as, for example, virulizin (Lorus Therapeutics), revimid (Celgene), CDC-394 (Celgene), entanercept (Immunex Corp.), infliximab (Centocor, Inc.), or adalimumab (Abbott Laboratories); endothelin A receptor antagonists, such as, for example, atrasentan (Abbott) YM-598 (Yamanouchi) or ZD-4054 (AstraZeneca); retinoic acid receptor agonists, such as, for example, fenretinide (Johnson & Johnson) alitretinoin (Ligand) or LGD-1550 (Ligand); immuno-modulators, such as, for example, interferon dexosome therapy (Anosys), oncophage (Antigenics), pentrix (Australian Cancer Technology), GMK (Progenics), ISF-154 (Tragen), adenocarcinoma vaccine (Biomira), cancer vaccine (Intercell), CTP-37 (AVI BioPharma), norelin (Biostar), IRX-2 (Immuno-Rx), BLP-25 (Biomira), PEP-005 (Peplin Biotech), MGV (Progenics), synchrovax vaccines (CTL Immuno), beta-alethine (Dovetail), melanoma vaccine (CTL Immuno), CLL therapy (Vasogen), or p21 RAS vaccine (GemVax); hormonal and antihormonal agents, such as, for example, estrogens, prednisone, conjugated estrogens, methylprednisolone, ethinyl estradiol, prednisolone, chlortrianisen, aminoglutethimide, idenestrol, leuprolide, hydroxyprogesterone caproate, goserelin, medroxyprogesterone, leuporelin, testosterone, bicalutamide, testosterone propionate, fluoxymesterone, flutamide, methyltestosterone, octreotide, diethylstilbestrol, nilutamide, megestrol, mitotane, tamoxifen, P-04 (Novogen), toremofine, 2-methoxyestradiol (EntreMed), dexamethasone, or arzoxifene (Eli Lilly); photodynamic agents, such as, for example, talaporfin (Light Sciences), Pd-bacteriopheophorbide (Yeda), Theralux (Theratechnologies), lutetium texaphyrin (Pharmacyclics), motexafin gadolinium (Pharmacyclics), or hypericin; and tyrosine kinase inhibitors, such as, for example, imatinib (Novartis), kahalide F (PharmaMar), leflunomide (Sugen/Pharmacia), CEP-701 (Cephalon), ZD1839 (AstraZeneca), CEP-751 (Cephalon), erlotinib (Oncogene Science), MLN518 (Millenium), canertinib (Pfizer), PKC412 (Novartis), squalamine (Genaera), phenoxodiol, SU5416 (Pharmacia), trastuzumab (Genentech), SU6668 (Pharmacia), C225 (ImClone), ZD4190 (AstraZeneca), rhu-Mab (Genentech), ZD6474 (AstraZeneca), MDX-H210 (Medarex), vatalanib (Novartis), 2C4 (Genentech), PKI166 (Novartis), MDX-447 (Medarex), GW2016 (GlaxoSmithKline), ABX-EGF (Abgenix), EKB-509 (Wyeth), IMC-1C11 (ImClone), or EKB-569 (Wyeth).

Those additional agents may be administered separately from the compound-containing composition, as part of a multiple dosage regimen. Alternatively, those agents may be part of a single dosage form, mixed together with the compound of this invention in a single composition. If administered as part of a multiple dosage regime, the two active agents may be submitted simultaneously, sequentially or within a period of time from one another normally within five hours from one another.

The amount of both, the compound and the additional therapeutic agent (in those compositions which comprise an additional therapeutic agent as described above)) that may be combined with the carrier materials to produce a single dosage form will vary depending upon the host treated and the particular mode of administration. Preferably, the compositions of this invention should be formulated so that a dosage of between 0.01-100 mg/kg body weight/day of a compound of formula I can be administered.

In those compositions that comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 mg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition. Implantable devices coated with a compound of this invention are another embodiment of the present invention.

In order that the invention described herein may be more fully understood, the following examples are set forth. It should be understood that these examples are for illustrative purposes only and are not to be construed as limiting this invention in any manner.

Preparation of Compounds of the Invention

The following definitions describe terms and abbreviations used herein:

Boc t-butoxylcarbonyl
brine water saturated with NaCl
BSA bovine serum albumin
DCM dichloromethane
DIAD diisopropylazodicarboxylate
DIEA diisopropylethylamine
DMF dimethylformamide
DMSO methylsulfoxide
ESMS electrospray mass spectrometry
Et$_2$O ethyl ether
EtOAc ethyl acetate
EtOH ethyl alcohol
HPLC high performance liquid chromatography
J In some structures, "J" is used to represent an iodine atom.
Me methyl
MeOH methanol
NBS N-bromosuccinimide
PdCl$_2$(dppf) 1,1'-bis(diphenylphosphino)ferrocene]dichloropalladium(II)
Ph phenyl
RT room temperature
tBu tertiary butyl
TCA trichloroacetic acid
THF tetrahydrofuran
TEA triethylamine
TFA trifluoacetic acid
TLC thin layer chromatography
TMS trimethylsilyl As used herein, other abbreviations, symbols and conventions are consistent with those used in the contemporary scientific literature. See, e.g., Janet S. Dodd, ed., *The ACS Style Guide: A Manual for Authors and Editors,* 2nd Ed., Washington, D.C.: American Chemical Society, 1997, herein incorporated in its entirety by reference.

As used herein, the term "Rt(min)" refers to the HPLC retention time, in minutes, associated with the compound. Unless otherwise indicated, the HPLC method utilized to obtain the reported retention time is as follows: column: Zorbax SB C18 column, 3.0×150 mm; gradient: 10-90% acetonitrile/water (0.1% TFA), 5 minutes; flow rate: 1.0 mL/minute; and detection: 254 & 214 nm.

Purifications by reversed-phase HPLC were conducted on a Waters 20×100 mm YMC-Pack Pro C18 column using a linear water/acetonitrile (0.1% TFA) gradient at a flow rate of 28 mL/minute. Beginning and final composition of the gradient varied for each compound between 10-40% and 50-90% acetonitrile, respectively.

Synthetic Procedures

In general, the compounds of this invention may be prepared by methods described herein or known to those skilled in the art for the preparation of analogous compounds. The following non-limiting schemes and examples are presented to further exemplify the invention. Physiochemical characterization of selected compounds of the invention is provided in Table 2.

EXAMPLE 1

Preparation of 5-bromo-3-(1-(2,3-difluoro-4-methoxyphenyl)-1H-tetrazol-5-yl)pyridin-2-amine (Compound 1005) and N-tert-butyl-3-(1-(4-bromo-2,3-difluorophenyl)-1H-tetrazol-5-yl)pyridin-2-amine (Compound 1009)

Scheme 1

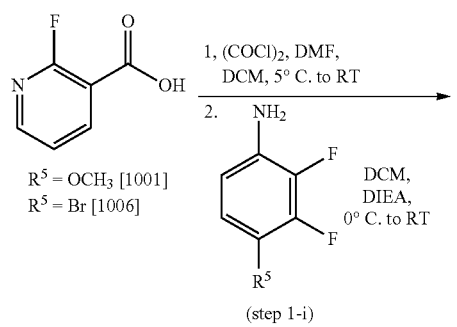

(step 1-i)

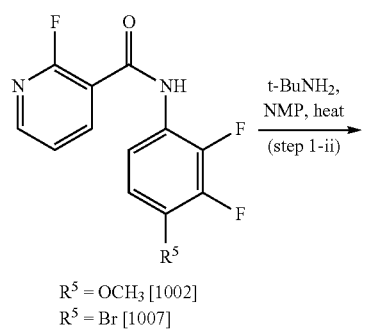

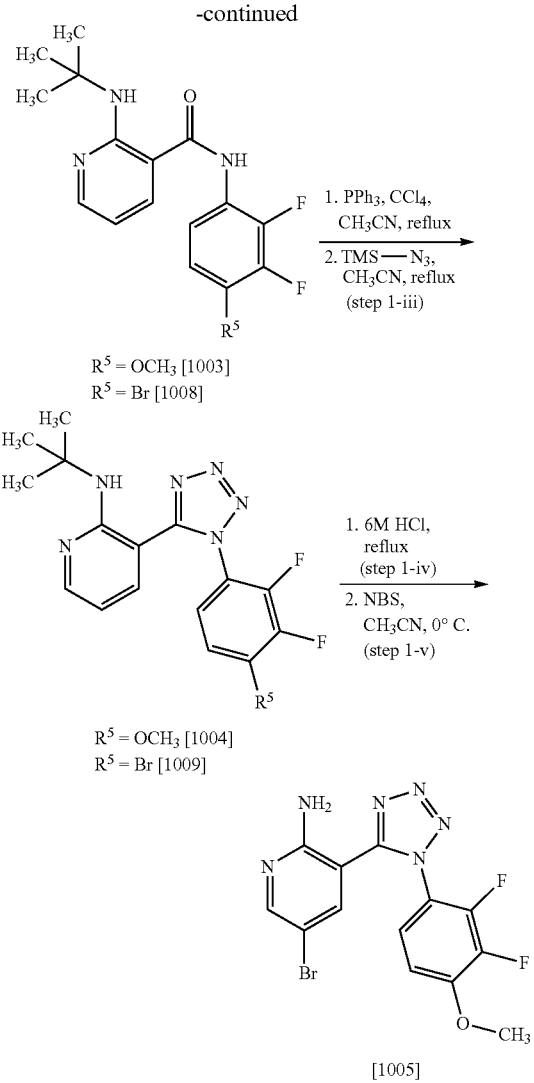

As shown in step 1-*i* of Scheme 1,2-fluoronicotinic acid (8.5 g, 59.0 mmol) was suspended in 100 mL of anhydrous dichloromethane and 0.274 mL of anhydrous DMF. The mixture was cooled to 5° C. with an ice bath. Oxalyl chloride (5.41 mL, 62.0 mmol) was added dropwise to the cooled mixture. After addition, the mixture was warmed to room temperature and stirred for 15 hours, at which time all solids had gone into solution. The mixture was cooled to 0° C. and 2,3-difluoro-4-methoxyaniline (Compound 1001, 10.0 g, 62.84 mmol) in 30 mL of DCM was added dropwise. Followed by the dropwise addition of DIEA (20.6 mL, 118.1 mmol). The mixture was warmed to room temperature and stirred for 16 hours, after which time the reaction was quenched with 60 mL of 2M HCl. The organics were washed twice with 50 mL of saturated sodium bicarbonate, once with 50 mL of water, and once with 50 mL of brine. The organics were then dried over anhydrous sodium sulfate, filtered, and evaporated under reduced pressure. The residue was slurried in 350 mL of hexanes, stirred for 30 minutes, collected by vacuum filtration, washed well with hexanes, and dried under vacuum to afford 2-fluoro-N-(2,3-difluoro-4-methoxyphenyl)pyridine-3-carboxamide (Compound 1002, 14.3 g, 86% yield): $^1$H NMR (300 MHz, CDCl$_3$) δ 8.68-8.62 (m, 2H), 8.40 (dt, J=4.7, 1.6 Hz, 1H), 8.06-7.99 (m, 1H), 7.44 (td, J=5.0, 2.5 Hz, 1H), 6.82-6.75 (m, 1H) and 3.91 (d, J=5.4 Hz, 3H).

As shown in step 1-*ii* of Scheme 1, Compound 1002 (9.8 g, 34.4 mmol) was dissolved in dry N-methylpyrrolidinone (75 mL) and tert-butylamine (25 mL, 237 mmol) and the mixture heated to 100° C. for 15 hours. The reaction was cooled to room temperature and poured into saturated NaHCO₃ with vigorous stirring. The resulting precipitate was collected by vacuum filtration, washed well with water, and dried in a vacuum oven for 16 hours. The solid was taken up in EtOAc and the organics washed with water and brine. After drying over sodium sulfate, filtration, and concentration under reduced pressure, the organics were treated with hexanes and the resulting precipitate collected by filtration to provide 2-(tert-butylamino)-N-(2,3-difluoro-4-methoxyphenyl)pyridine-3-carboxamide (Compound 1003, 9.2 g, 79.8% yield): $^1$H NMR (300 MHz, CDCl₃) 8.26 (dd, J=1.8, 4.7 Hz, 1H), 8.01 (s, 1H), 7.83-7.77 (m, 1H), 7.68-7.64 (m, 2H), 6.80-6.73 (m, 1H), 6.51 (dd, J=4.7, 7.7 Hz, 1H), 3.91 (s, 3H) and 1.49 (s, 9H).

As shown in step 1-*iii* of Scheme 1, Compound 1003 (9.2 g, 27.4 mmol) was taken up in 100 mL of anhydrous acetonitrile. Triphenylphosphine (8.26 mL, 35.7 mmol) was added and the mixture stirred at room temperature for 5 minutes, followed by the addition of carbon tetrachloride (3.18 mL, 32.9 mmol). The mixture was refluxed for 3 hours, cooled to room temperature, and TMS-azide (5.41 mL, 41.14 mmol) was added. The reaction was heated to reflux for 18 hours, cooled to room temperature, diluted with EtOAc, washed with saturated sodium bicarbonate, and dried over sodium sulfate. The organics were filtered, concentrated under reduced pressure, and purified by silica gel chromatography (10-30% EtOAc/hexanes) to yield N-tert-butyl-3-(1-(2,3-difluoro-4-methoxyphenyl)-1H-tetrazol-5-yl)pyridin-2-amine (Compound 1004, 7.80 g, 78.9% yield): ESMS (M+1)=361.

As shown in step 1-*iv* of Scheme 1, Compound 1004 (5.0 g, 13.9 mmol) was taken up in 15 mL of methanol and 30 mL of 6M HCl. After refluxing for 10 hrs, the mixture was cooled to 0° C. and the pH adjusted to 8 with 6M sodium hydroxide. The resulting white precipitate was collected by vacuum filtration, washed well with water, and dried at 55° C. under vacuum for 16 hours to afford 3-(1-(2,3-difluoro-4-methoxyphenyl)-1H-tetrazol-5-yl)pyridin-2-amine (4.2 g): ESMS (M+1)=305.

As shown in step 1-*v* of Scheme 1,3-(1-(2,3-difluoro-4-methoxyphenyl)-1H-tetrazol-5-yl)pyridin-2-amine (4.2 g) was suspended in 50 mL of anhydrous acetonitrile and cooled to 0° C. NBS (2.60 g, 14.62 mmol) was added portionwise to the mixture and stirred for 1 hour. A concentrated solution of sodium sulfite was added to the mixture followed by the addition of concentrated sodium bicarbonate. After stirring at room temperature for 1 hour the reaction was filtered, washed well with water, and dried for 16 hours at 55° C. under vacuum to give 5-bromo-3-(1-(2,3-difluoro-4-methoxyphenyl)-1H-tetrazol-5-yl)pyridin-2-amine (Compound 1005, 4.50 g, 85.1% yield): ESMS (M+1)=383; $^1$H NMR (300 MHz, DMSO-d₆) δ 8.20 (d, J=2.5 Hz, 1H), 7.64-7.56 (m, 2H), 7.36-7.28 (m, 1H), 6.73 (s, 2H), and 3.97 (s, 3H).

The same sequence of reactions used to convert Compound 1001 to Compound 1004 was used to convert Compound 1006 to Compound 1009. Characterization data are as follows: Compound 1007: ESMS (M+1)=329.16/331.12; Compound 1008: ESMS (M+1)=382.36/384.34; and Compound 1009: $^1$H NMR (300 MHz, DMSO-d₆) δ 8.21 (dd, J=1.9, 4.8 Hz, 1H), 7.90-7.84 (m, 1H), 7.54-7.48 (m, 1H), 7.44 (dd, J=1.9, 7.7 Hz, 1H), 6.71 (s, 1H), 6.58 (dd, J=4.8, 7.7 Hz, 1H), and 1.31 (s, 9H).

The following anilines can be similarly used as starting materials in the synthesis of other intermediate 5-bromo-3-(substituted-phenyl)-1H-tetrazol-5-yl)pyridin-2-amines that are useful for preparing compounds of the invention:

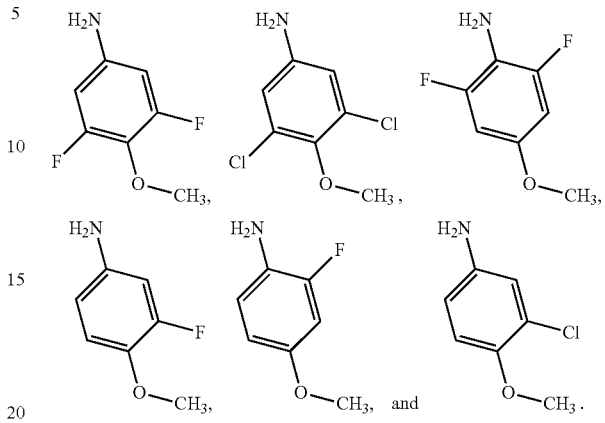

EXAMPLE 2

Preparation of 1-(tetrahydro-2H-pyran-4-yl)-4-(4,4,5,5-tetramethyl-1,3,2-dioxaborolan-2-yl)-1H-pyrazole (Compound 1012)

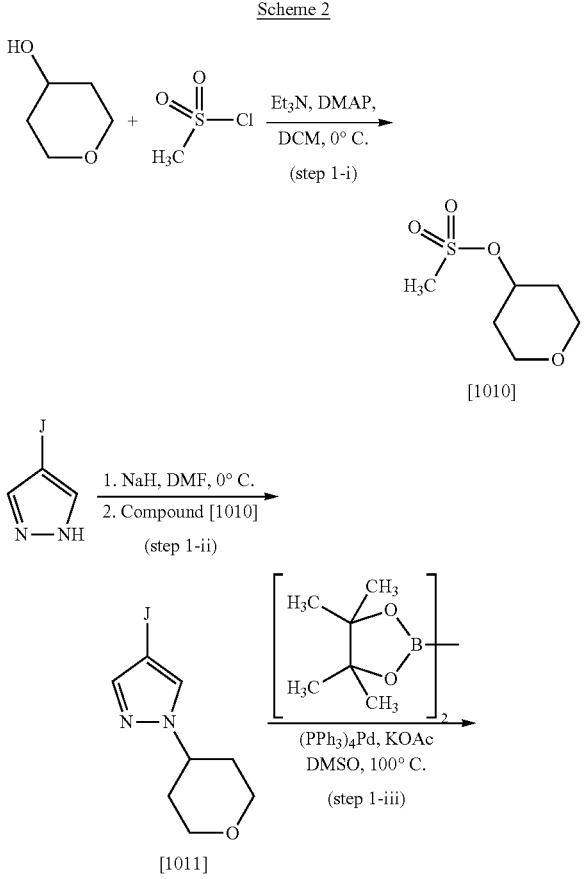

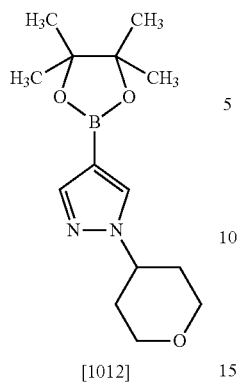

[1012]

As shown in step 2-*i* of Scheme 2, methanesulfonyl chloride (12 mL, 0.155 mol) was added dropwise to a mixture of tetrahydro-2H-pyran-4-ol (15.83 g, 0.155 mol), triethylamine (21.6 mL, 0.155 mol), and dimethylaminopyridine (1.89 g, 0.015 mol) in 200 mL of DCM at 0° C. The reaction was warmed to room temperature and stirred for 16 hours. The organics were washed with water, washed with brine, dried over magnesium sulfate, filtered, and the volatiles removed under reduced pressure to provide tetrahydro-2H-pyran-4-yl methanesulfonate (Compound 1010, 22.6 g, 80.9% yield) as a yellow solid: $^1$H NMR (300 MHz, CDCl$_3$) δ 4.90 (qn, J=4.2 Hz, 1H), 3.95 (dt, J=12.0, 4.2 Hz, 2H), 3.59-3.51 (m, 2H), 3.04 (s, 3H), 2.08-2.01 (m, 2H), 1.94-1.82 (m, 2H).

As shown in step 2-*ii* of Scheme 2, sodium hydride (6.101 mL of 60% NaH/mineral oil, 137.3 mmol) was added slowly to a solution of 4-iodopyrazole (24.21 g, 124.8 mmol) in 200 mL of anhydrous DMF at 0° C. The solution was stirred for 1 hour at 0° C. and tetrahydro-2H-pyran-4-yl methanesulfonate (Compound 1010, 22.5 g, 124.8 mmol) in 100 mL of anhydrous DMF was added dropwise. The reaction mixture was heated at 100° C. for 18 hours, at which time an additional 8.0 g of (Compound 1010) in 25 mL of anhydrous DMF was added dropwise. The reaction mixture was heated at 100° C. for an additional 24 hours. The mixture was cooled to room temperature and 100 mL of water was added. The mixture was extracted with EtOAc (3×100 mL) and the combined organics were washed with water, washed with brine, dried over sodium sulfate, filtered, and concentrated under reduced pressure to afford a semi-solid. Recrystallization from DCM yielded 1-(tetrahydro-2H-pyran-4-yl)-4-iodo-1H-pyrazole (Compound 1011, 11.96 g). A second crop of crystals was obtained upon trituration of the mother liquor with hexanes (5.26 g, 49.6% total yield): ESMS (M+H)=279.0.

As shown in step 2-*iii* of Scheme 2, a mixture of 1-(tetrahydro-2H-pyran-4-yl)-4-iodo-1H-pyrazole (Compound 1011, 1.0 g, 3.60 mmol), potassium acetate (776 mg, 7.91 mmol), and bis(pinacol)diboron (1.37 g, 5.39 mmol) in DMSO was flushed with nitrogen for 30 minutes. Tetrakis (triphenylphosphine)palladium (0) (623.3 mg, 0.539 mmol) was added and the reaction heated at 95° C. for 16 hours. After cooling to room temperature, the mixture was diluted with EtOAc and filtered through a plug of Florisil®, which was subsequently washed with EtOAc/hexanes. The filtrate was concentrated under reduced pressure and the residue purified by silica gel chromatography (0-50% EtOAc/hexanes) to provide 1-(tetrahydro-2H-pyran-4-yl)-4-(4,4,5,5-tetramethyl-1,3,2-dioxaborolan-2-yl)-1H-pyrazole as a while solid (Compound 1012, 385 mg, 38.5% yield): $^1$H NMR (300 MHz, CDCl$_3$) δ 7.80 (s, 1H), 7.75 (s, 1H), 4.36 (m, 1H), 4.08 (d, 2H), 3.57 (t, 2H), 2.08 (m, 4H), 1.32 (s, 12H).

EXAMPLE 3

Preparation of tert-butyl 4-(4-(4,4,5,5-tetramethyl-1,3,2-dioxaborolan-2-yl)-1H-pyrazol-1-yl)piperidine-1-carboxylate (Compound 1015)

Scheme 3

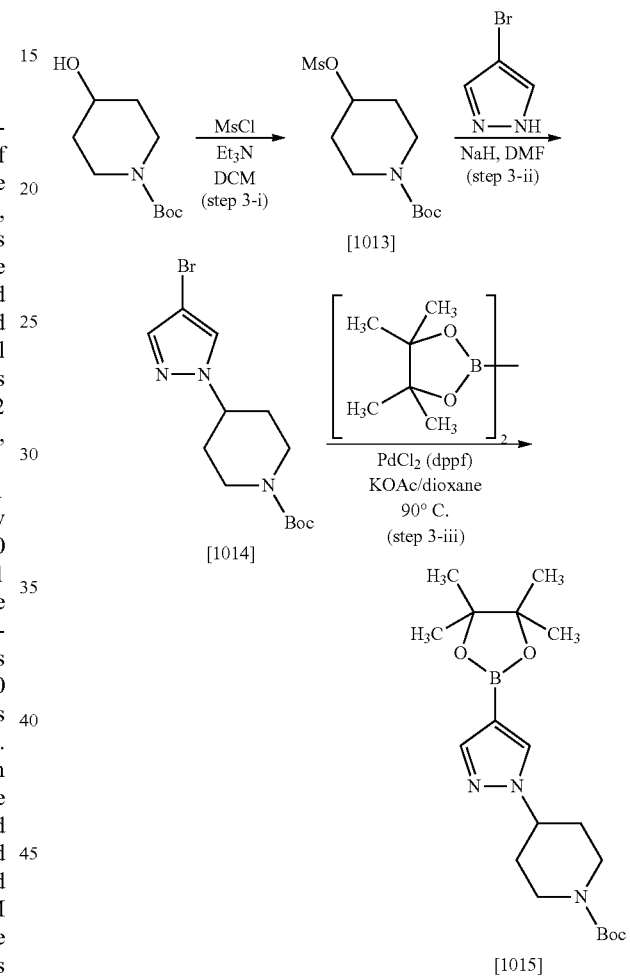

As shown in step 3-*i* of Scheme 3, N-Boc-4-hydroxypiperidine (30 g, 149.1 mmol, 1 eq.), triethylamine (22.87 mL, 164 mmol, 1.1 eq.) and N,N-dimethylpyridin-4-amine (DMAP) (1.83 g, 14.98 mmol, 0.1 eq.) were dissolved in anhydrous methylene chloride (500 mL) and cooled to 0° C. in an ice bath. Methanesulfonyl chloride (12.12 mL, 156.6 mmol, 1.05 eq.) was added dropwise. Upon completion of the addition, the reaction was warmed to room temperature and stirred for 16 hours. The reaction was washed with water (3×100 mL) and saturated sodium bicarbonate (3×100 mL). The combined aqueous washes were back-extracted with methylene chloride. The combined organics were dried over Na$_2$SO$_4$, and concentrated to give 40.83 g (146.2 mmol) of 1-(tert-butoxycarbonyl)piperidin-4-yl methanesulfonate (Compound 1013, 98% yield), an off white solid that was used without further purification.

As shown in step 3-*ii* of Scheme 3, to a solution of 4-bromopyrazole (4.68 g, 31.83 mmol) in DMF (300 mL) at 0° C. was added sodium hydride (60% on mineral oil, 1.27 g, 31.83 mmol). The solution was stirred at 0° C. for one hour, at which point a solution of Compound 1013 (9.78 g, 31.83 mmol) in DMF (50 mL) was added dropwise. The reaction mixture was stirred at room temperature for 1 hour and then refluxed for 16 hours. Disappearance of both starting materials was observed by TLC (1:1 EtOAc/hexanes). The reaction was cooled to room temperature, quenched by the addition of brine (300 mL), and extracted with ethyl acetate (3×200 mL). The combined organics were washed with 1% aqueous LiCl (3×200 mL), dried over sodium sulfate, and concentrated under reduced pressure. The resulting crude bromide was purified by silica gel chromatography (0-25% EtOAc/hexanes) to give Compound 1014.

As shown in step 3-*iii* of Scheme 3, tert-butyl 4-(4-bromo-1H-pyrazol-1-yl)piperidine-1-carboxylate (Compound 1014, 10.52 g, 31.86 mmol), 4,4,5,5-tetramethyl-2-(4,4,5,5-tetramethyl-1,3,2-dioxaborolan-2-yl)-1,3,2-dioxaborolane (9.71 g, 38.23 mmol), and potassium acetate (9.38 g, 95.58 mmol) were taken up in 105 mL of 1,4-dioxane. The mixture was flushed with nitrogen for 20 minutes and PdCl$_2$(dppf) (1.3 g, 1.59 mmol) was added. The reaction was heated at 90° C. for 11 hours. The reaction was cooled to room temperature and filtered through a plug of Florisil®, which was subsequently rinsed with ethyl acetate. The filtrate was concentrated under reduced pressure to afford a dark brown oil that was dissolved in hexanes and eluted through a second plug of Florisil® with 1:2 EtOAc/hexanes. The filtrate was concentrated under reduced pressure to give a tan oil, which was triturated with hexanes and stirred at 0° C. until a white precipitate formed. The precipitate was collected by vacuum filtration, washed with hexanes, and dried to afford 6.79 g of tert-butyl 4-(4-(4,4,5,5-tetramethyl-1,3,2-dioxaborolan-2-yl)-1H-pyrazol-1-yl)piperidine-1-carboxylate (Compound 1015).

In a manner similar to the conversion of Compound 1011 to Compound 1012 and Compound 1014 to Compound 1015, other aryl or heteroaryl halides can be converted to the boronate intermediates used in the preparation of the compounds of the invention.

EXAMPLE 4

Preparation of 3-(1-(4-(4-(methylamino)butoxy)-2,3-difluorophenyl)-1H-tetrazol-5-yl)-5-(1-methyl-1H-pyrazol-4-yl)pyridin-2-amine (Compound 137)

Scheme 4

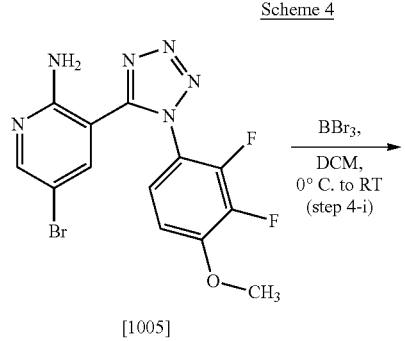

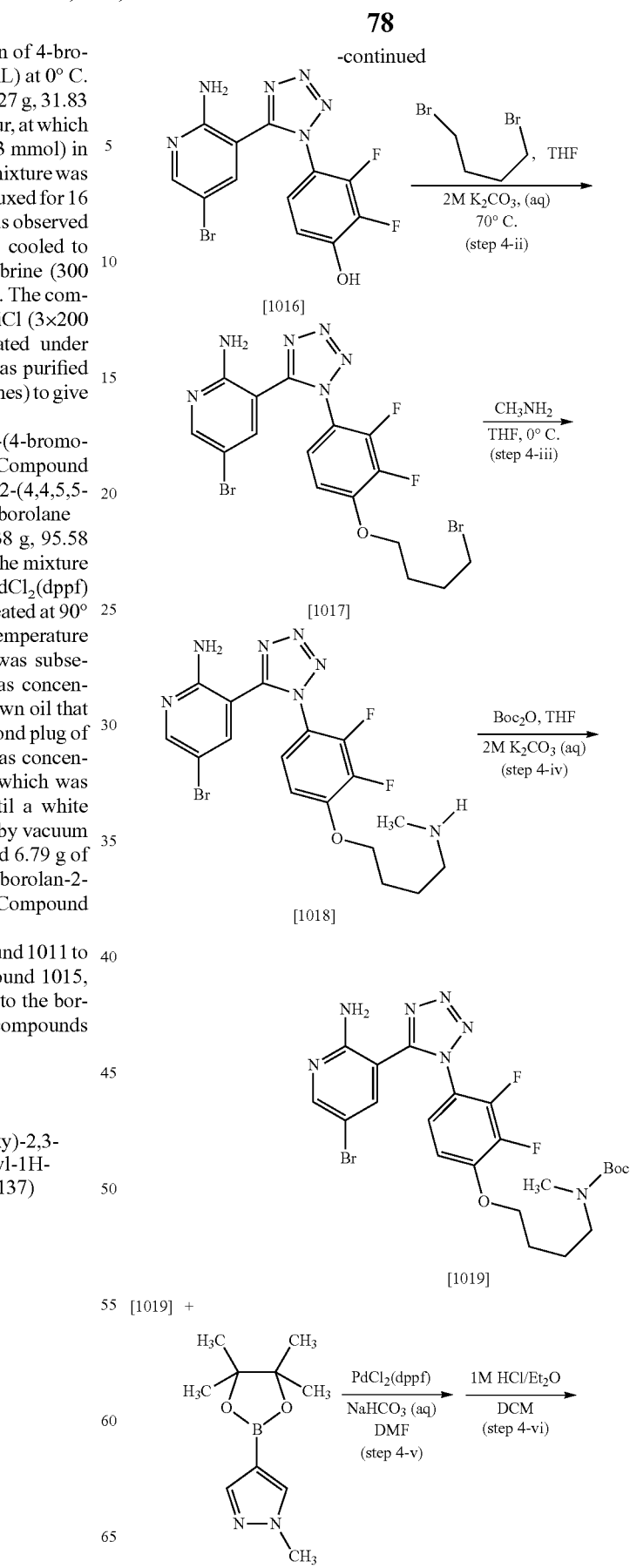

-continued

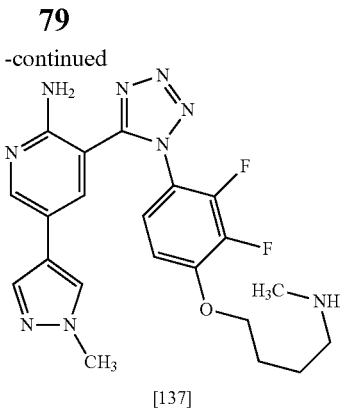

[137]

As shown in step **4-*i*** of Scheme 4,5-bromo-3-(1-(2,3-difluoro-4-methoxyphenyl)-1H-tetrazol-5-yl)pyridin-2-amine (Compound 1005, 20.0 g, 7.663 mmol) in 150 mL of DCM was cooled 0° C. Boron tribromide (20.0 mL of a 1M solution in DCM, 20 mmol) was added dropwise. After the addition was complete, the reaction mixture was warmed to room temperature and stirred for 48 hours. The reaction was carefully quenched with crushed ice and extracted with EtOAc (3×200 mL). The combined organics were washed with water, washed with brine, and dried over sodium sulfate. After filtration, the volatiles were removed under reduced pressure to yield a brown solid, which was triturated with pentane to yield 4-(5-(2-amino-5-bromopyridin-3-yl)-1H-tetrazol-1-yl)-2,3-difluorophenol (Compound 1016) as a pale brown solid.

As shown in step **4-*ii*** of Scheme 4, to a solution of 4-(5-(2-amino-5-bromopyridin-3-yl)-1H-tetrazol-1-yl)-2,3-difluorophenol (Compound 1016, 3.0 g, 8.13 mmol) in 30 mL of THF was added 14.13 mL of 2M $K_2CO_3$ (aq), followed by the addition of 1,4-dibromobutane (2.44 mL, 20.325 mmol) (28.26 mmol). The reaction mixture was heated to 70° C. and stirred at this temperature for 16 hours. The mixture was cooled, concentrated under reduced pressure, taken up in EtOAc (100 mL), washed with water (3×30 mL) and washed with brine (30 mL). After drying over sodium sulfate, the organics were filtered and the volatiles removed under reduced pressure to provide an off-white solid. Purification of the solid by silica gel chromatography (10% EtOAc/hexanes) provided 3-(1-(4-(4-bromobutoxy)-2,3-difluorophenyl)-1H-tetrazol-5-yl)-5-bromopyridin-2-amine (Compound 1017, 3.0 g, 73% yield).

As shown in step **4-*iii*** of Scheme 4,3-(1-(4-(4-bromobutoxy)-2,3-difluorophenyl)-1H-tetrazol-5-yl)-5-bromopyridin-2-amine (Compound 1017, 3.0 g, 4.08 mmol) was dissolved in 30 mL of THF and cooled to 0° C. Methylamine (generated by heating 50 mL of 40% methylamine in water) was bubbled into the reaction mixture and stirring continued for 4 hours. After starting material had been consumed by TLC analysis, the reaction mixture was concentrated under reduced pressure and the residue taken up in 100 mL of EtOAc. The organics were washed with water (3×30 mL) and brine (30 mL). After drying over sodium sulfate, the organics were filtered and the volatiles removed under reduced pressure to provide 3-(1-(4-(4-(methylamino)butoxy)-2,3-difluorophenyl)-1H-tetrazol-5-yl)-5-bromopyridin-2-amine (Compound 1018, 1.60 g, 88% yield) as a white solid.

As shown in step **4-*iv*** of Scheme 4,3-(1-(4-(4-(methylamino)butoxy)-2,3-difluorophenyl)-1H-tetrazol-5-yl)-5-bromopyridin-2-amine (Compound 1018, 1.80 g, 4.088 mmol) was dissolved in 20 mL of THF and a 2M aqueous solution of $K_2CO_3$ (6 mL) was added, followed by the addition of di-tert-butyldicarbonate (1.0 mL, 4.35 mmol). The reaction mixture was stirred at room temperature for 16 hours. After extraction with EtOAc (2×100 mL), the combined organics were washed with water (2×50 mL), washed with brine (50 mL), and dried over sodium sulfate. After filtration, the volatiles were removed under reduced pressure to provide tert-butyl 4-(4-(5-(2-amino-5-bromopyridin-3-yl)-1H-tetrazol-1-yl)-2,3-difluorophenoxy)butylmethylcarbamate (Compound 1019, 1.80 g, 82% yield) as a white solid.

As shown in step **4-*v*** of Scheme 4, tert-butyl 4-(4-(5-(2-amino-5-bromopyridin-3-yl)-1H-tetrazol-1-yl)-2,3-difluorophenoxy)butylmethylcarbamate (Compound 1019, 554 mg, 1.00 mmol) and 1-methyl-4-(4,4,5,5-tetramethyl-1,3,2-dioxaborolan-2-yl)-1H-pyrazole (250 mg, 1.20 mmol) were dissolved in 8.0 mL of DMF and 4.0 mL of saturated $NaHCO_3$ (aq) were added. The mixture was flushed with argon gas for 1 hour and $PdCl_2(dppf)$ (43.2 mg, 53.0 mmol) was added. The reaction mixture was flushed with argon for an additional 30 minutes followed by heating to 100° C. for 1 hour. After cooling, the mixture was diluted with EtOAc (80 mL), washed with water (3×40 mL), washed with brine (40 mL), and dried over sodium sulfate. After filtration, the organics were concentrated under reduced pressure and the residue purified by silica gel chromatography (40% EtOAc/hexanes) to provide tert-butyl 4-(4-(5-(2-amino-5-(1-methyl-1H-pyrazol-4-yl)pyridin-3-yl)-1H-tetrazol-1-yl)-2,3-difluorophenoxy)butylmethylcarbamate (278 mg, 50% yield), which was used as is in subsequent reactions.

As shown in step **4-*vi*** of Scheme 4, tert-butyl 4-(4-(5-(2-amino-5-(1-methyl-1H-pyrazol-4-yl)pyridin-3-yl)-1H-tetrazol-1-yl)-2,3-difluorophenoxy)butylmethylcarbamate (147 mg, 265 mmol) was taken up in 4 mL of DCM and treated with 1M HCl in ethyl ether (1.0 mL). The reaction mixture was warmed to room temperature and stirred for 16 hours. The volatiles were removed under reduced pressure and the resulting white solid was triturated with ethyl ether to provide 3-(1-(4-(4-(methylamino)butoxy)-2,3-difluorophenyl)-1H-tetrazol-5-yl)-5-(1-methyl-1H-pyrazol-4-yl)pyridin-2-amine hydrochloride (Compound 137, 109 mg, 84% yield).

Using the appropriate dibromoalkane, amine, and boronate, the following compounds were prepared by a procedure similar to that as described above in Example 4: Compounds 134-135 and 137-138.

EXAMPLE 5

Preparation of 3-(1-(4-(4-morpholinobutoxy)-2,3-difluorophenyl)-1H-tetrazol-5-yl)-5-(1-isopentyl-1H-pyrazol-4-yl)pyridin-2-amine (Compound 150)

Scheme 5

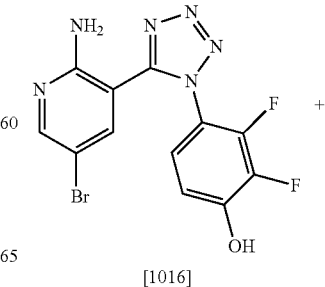

[1016]

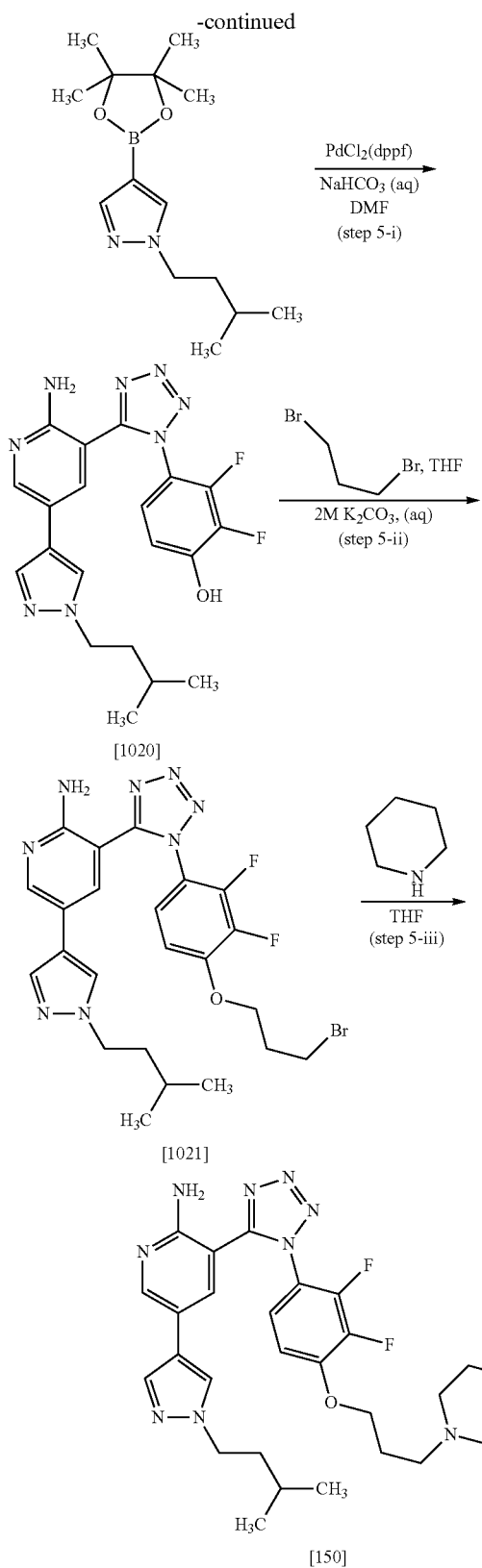

[1020]

[1021]

[150]

As shown in step **5-*i*** of Scheme 5, to a solution of 4-(5-(2-amino-5-bromopyridin-3-yl)-1H-tetrazol-1-yl)-2,3-difluorophenol (Compound 1016, 2.0 g, 5.42 mmol) and 1-isopentyl-4-(4,4,5,5-tetramethyl-1,3,2-dioxaborolan-2-yl)-1H-pyrazole (1.57 g, 5.96 mmol) in 26 mL of DMF was added 13 mL of saturated NaHCO$_3$ (aq). The mixture was flushed with argon gas for 45 minutes and PdCl$_2$(dppf) (442 mg, 6.54 mmol) was added. The reaction mixture was flushed with argon for an additional 30 minutes and then heated at 100° C. for 1 hour. After cooling, the reaction mixture was diluted with EtOAc (100 mL), washed with water (50 mL), washed with brine (50 mL) dried over sodium sulfate, filtered, and concentrated under reduced pressure. The residue was purified by silica gel chromatography (80% EtOAc/hexanes) to provide 4-(5-(2-amino-5-(1-isopentyl-1H-pyrazol-4-yl)pyridin-3-yl)-1H-tetrazol-1-yl)-2,3-difluorophenol (Compound 1020, 2.0 g, 58% yield).

As shown in step **5-*ii*** of Scheme 5,4-(5-(2-amino-5-(1-isopentyl-1H-pyrazol-4-yl)pyridin-3-yl)-1H-tetrazol-1-yl)-2,3-difluorophenol (Compound 1020, 690 mg, 1.62 mmol) was taken up in 15 mL of THF, cooled to 0° C. and 2.0 mL of 2M K$_2$CO$_3$ (aq) were added, followed by the addition of 1,3-dibromopropane (0.40 mL, 4.043 mmol). The reaction mixture was heated at 80° C. for 16 hours. The mixture was cooled to room temperature, treated with cold water, and extracted with CHCl$_3$ (2×50 mL). The combined organics were washed with brine, dried over sodium sulfate, filtered, and the volatiles removed under reduced pressure. The residue was purified by silica gel chromatography (60-80% EtOAc/hexanes) to provide 3-(1-(4-(3-bromobutoxy)-2,3-difluorophenyl)-1H-tetrazol-5-yl)-5-(1-isopentyl-1H-pyrazol-4-yl)pyridin-2-amine (Compound 1021, 680 mg, 53% yield).

As shown in step **5-*iii*** of Scheme 5,3-(1-(4-(3-bromobutoxy)-2,3-difluorophenyl)-1H-tetrazol-5-yl)-5-(1-isopentyl-1H-pyrazol-4-yl)pyridin-2-amine (Compound 1021, 111 mg, 0.203 mmol) was dissolved in 5 mL of THF and cooled to 0° C. The mixture was treated with piperidine (0.06 mL, 0.61 mmol), warmed to 70° C., and stirred for 16 hours. The reaction was cooled to room temperature, treated with cold water, and extracted with CHCl$_3$ (50 mL). The organics were washed with water, washed with brine, dried over sodium sulfate, filtered, and the volatiles removed under reduced pressure. The residue was purified by silica gel chromatography (5% MeOH/CHCl$_3$) to provide 3-(1-(4-(3-(piperidin-1-yl)propoxy)-2,3-difluorophenyl)-1H-tetrazol-5-yl)-5-(1-isopentyl-1H-pyrazol-4-yl)pyridin-2-amine (Compound 150, 70 mg, 78% yield).

Using the appropriate boronate, dibromoalkane, and amine, the following compounds were prepared by a procedure similar to that as described above in Example 5: Compounds 132-133, 136, 148-149, 151-154, 157-171, and 174-176.

EXAMPLE 6

Preparation of 3-(1-(4-(2-(Dimethylamino)ethoxy)-2,3-difluorophenyl)-1H-tetrazol-5-yl)-5-(1-methyl-1H-pyrazol-4-yl)pyridin-2-amine (Compound 2)

Scheme 6

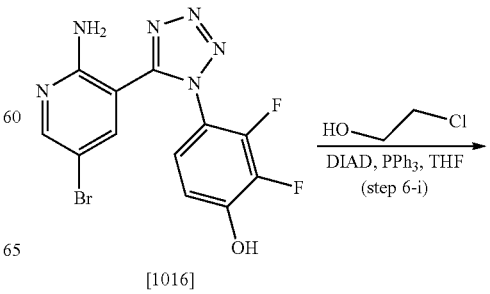

[1016]

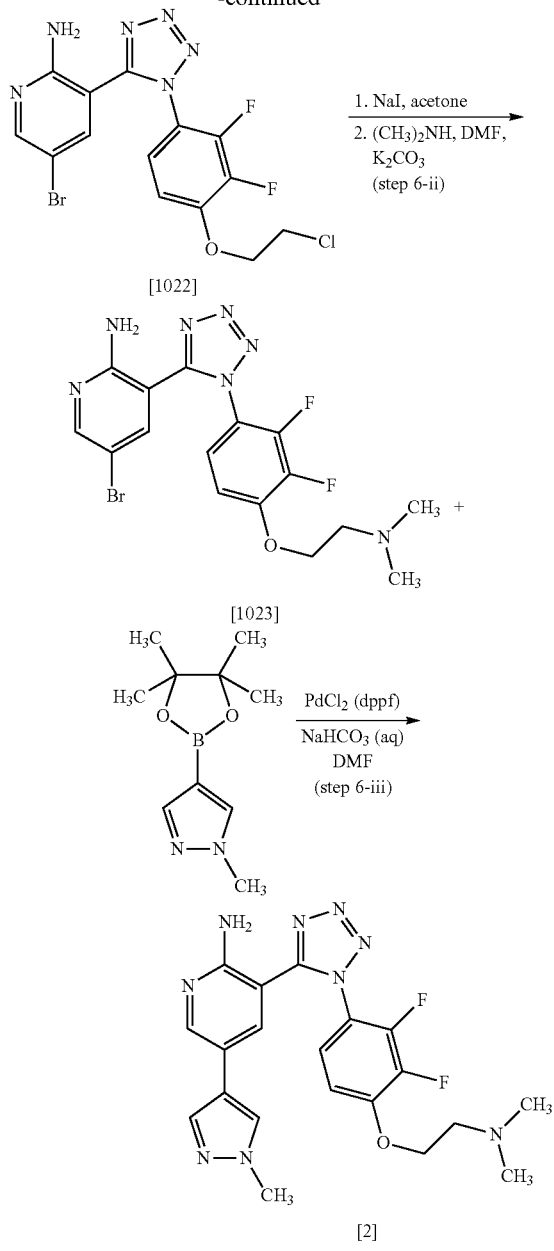

mmol) in 13.5 mL of acetone was added sodium iodide (812.7 mg, 5.42 mmol) and the reaction mixture was heated at reflux for 16 hours. Additional sodium iodide (406 mg, 2.71 mmol) was added and the reaction was sealed and heated at 100° C. under microwave irradiation for 20 minutes to complete conversion of the chloride to the intermediate iodide. After cooling, the mixture was filtered and concentrated under reduced pressure. The residue was dissolved in DMF (10 mL) and $K_2CO_3$ (562 mg, 4.07 mmol) and dimethylamine (2.03 mL of a 2M solution in THF, 4.07 mmol) were added. The reaction mixture was sealed and stirred for 16 hours at room temperature. The mixture was diluted with EtOAc and the organics washed with water (3×), washed with brine, dried over sodium sulfate, filtered, and the volatiles removed under reduced pressure to provide 3-(1-(4-(2-(dimethylamino)ethoxy)-2,3-difluorophenyl)-1H-tetrazol-5-yl)-5-bromopyridin-2-amine (Compound 1023, 1.09 g, 87% yield).

As shown in step 6-*iii* of Scheme 6, a mixture of 3-(1-(4-(2-(dimethylamino)ethoxy)-2,3-difluorophenyl)-1H-tetrazol-5-yl)-5-bromopyridin-2-amine (Compound 1023, 50 mg, 0.114 mmol), 1-methyl-4-(4,4,5,5-tetramethyl-1,3,2-dioxaborolan-2-yl)-1H-pyrazole (30.7 mg, 0.148 mmol), and 1.2M $NaHCO_3$ (aq) (284 μL, 0.341 mmol) in 3 mL of DMF was flushed with nitrogen gas for 1 hour. $PdCl_2$(dppf) (5.0 mg, 0.007 mmol) was added and the mixture was heated in a sealed tube under microwave irradiation at 120° C. for 11 minutes. After cooling, the reaction mixture was poured into saturated sodium bicarbonate (aq), which was subsequently extracted with EtOAc. The combined organics were washed with brine, dried over sodium sulfate, filtered, and concentrated under reduced pressure. The residue was purified by silica gel chromatography (0-50% 1:9 7M $NH_3$ in methanol/DCM). The resulting purified product was dissolved in methanol, treated with 2M HCl/ethyl ether, and stirred for 20 minutes. After concentration under reduced pressure, the residue was dissolved in acetonitrile/water and lyophilized to provide 3-(1-(4-(2-(dimethylamino)ethoxy)-2,3-difluorophenyl)-1H-tetrazol-5-yl)-5-(1-methyl-1H-pyrazol-4-yl)pyridin-2-amine (Compound 2, 8.3 mg, 14% yield).

Using the appropriate phenol, amine, and boronate, the following compounds were prepared by a procedure similar to that as described above in Example 6: Compounds 1, 4-96, 100-105, and 110-111.

EXAMPLE 7

Preparation of 3-(1-(4-(4-(methylamino)cyclohexyloxy)-2,3-difluorophenyl)-1H-tetrazol-5-yl)-5-(1-methyl-1H-pyrazol-4-yl)pyridin-2-amine (Compound 131) and 3-(1-(4-(4-(dimethylamino)cyclohexyloxy)-2,3-difluorophenyl)-1H-tetrazol-5-yl)-5-(1-methyl-1H-pyrazol-4-yl)pyridin-2-amine (Compound 177)

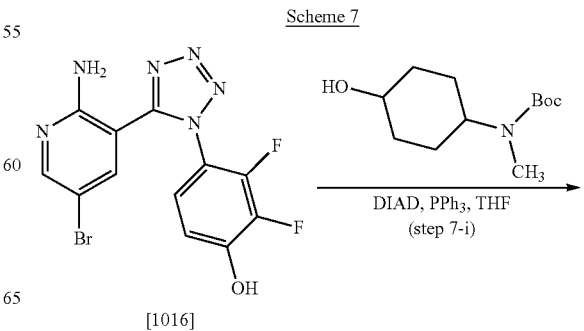

As shown in step 6-*i* of Scheme 6, to a solution of 4-(5-(2-amino-5-bromopyridin-3-yl)-1H-tetrazol-1-yl)-2,3-difluorophenol (Compound 1016, 1.0 g, 2.71 mmol), 2-chloroethanol (218 μL, 3.25 mmol), and triphenylphosphine (853 mg, 3.25 mmol) in 4 mL of THF at 0° C. was added diisopropylazodicarboxylate (630 μL, 3.25 mmol). The mixture was heated under microwave irradiation at 80° C. for 10 minutes. After cooling, the mixture was diluted with EtOAc, washed with saturated ammonium chloride, washed with brine, dried over sodium sulfate, filtered, and concentrated under reduced pressure. The residue was purified by silica gel chromatography (0-40% EtOAc/hexanes) to provide 3-(1-(4-(2-chloroethoxy)-2,3-difluorophenyl)-1H-tetrazol-5-yl)-5-bromopyridin-2-amine (Compound 1022, 1.169 g, 100% yield).

As shown in step 6-*ii* of Scheme 6, to a solution of 3-(1-(4-(2-chloroethoxy)-2,3-difluorophenyl)-1H-tetrazol-5-yl)-5-bromopyridin-2-amine (Compound 1022, 1.169 g, 2.71

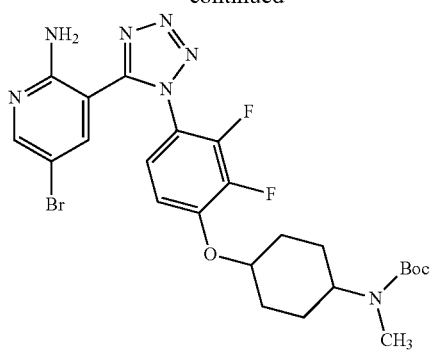

[1024]

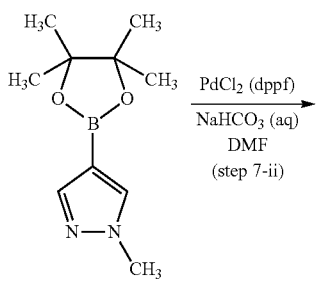

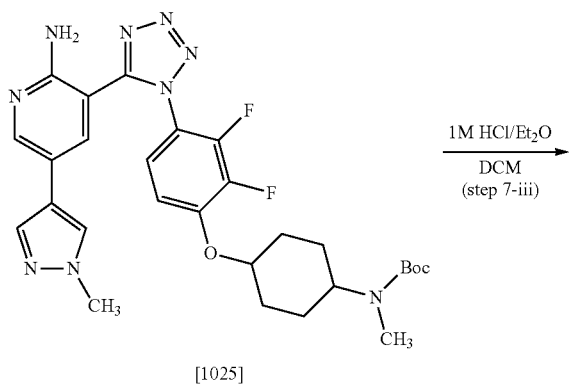

[1025]

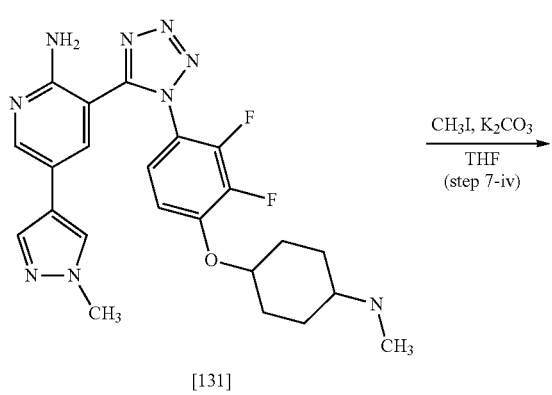

[131]

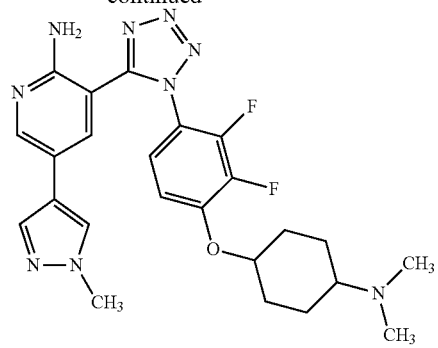

[177]

As shown in step 7-i of Scheme 7, to a solution of 4-(5-(2-amino-5-bromopyridin-3-yl)-1H-tetrazol-1-yl)-2,3-difluorophenol (Compound 1016, 2.06 g, 5.59 mmol), tert-butyl 4-hydroxycyclohexylmethylcarbamate (1.60 g, 7.0 mmol), and triphenylphosphine (548 mg, 13.97 mmol) in 80 mL of THF at 0° C. was slowly added diisopropylazodicarboxylate (5.53 mL, 27.9 mmol). After addition was complete, the reaction mixture was warmed to room temperature and stirring was continued for an additional 1 hour at RT. The reaction was quenched with 50 mL of saturated NH$_4$Cl (aq) and extracted with EtOAc (2×50 mL). The combined organics were washed with water (50 mL), washed with brine (50 mL), dried over sodium sulfate, filtered, and concentrated under reduced pressure. The residue was purified by silica gel chromatography (20% EtOAc/hexanes) to provide tert-butyl 4-(4-(5-(2-amino-5-bromopyridin-3-yl)-1H-tetrazol-1-yl)-2,3-difluorophenoxy)cyclohexylmethylcarbamate (Compound 1024, 1.0 g, 31% yield).

As shown in step 7-ii of Scheme 7, a mixture of tert-butyl 4-(4-(5-(2-amino-5-bromopyridin-3-yl)-1H-tetrazol-1-yl)-2,3-difluorophenoxy)cyclohexylmethylcarbamate (Compound 1024, 250 mg, 0.43 mmol), 1-methyl-4-(4,4,5,5-tetramethyl-1,3,2-dioxaborolan-2-yl)-1H-pyrazole (90 mg, 0.43 mmol), 2 mL of saturated NaHCO$_3$, and 4 mL of DMF were flushed with argon gas for 1 hour. PdCl$_2$(dppf) (17 mg, 0.021 mmol) was added and the reaction mixture flushed with argon gas for an additional 30 minutes, followed by heating at 100° C. for 1 hour. After cooling, the mixture was diluted with 40 mL of EtOAc, washed with water (3×20 mL), washed with brine (20 mL), dried over sodium sulfate, filtered, and concentrated under reduced pressure. The residue was purified by silica gel chromatography (40% EtOAc/hexanes to produce tert-butyl 4-(4-(5-(2-amino-5-(1-methyl-1H-pyrazol-4-yl)pyridin-3-yl)-1H-tetrazol-1-yl)-2,3-difluorophenoxy)cyclohexylmethylcarbamate (Compound 1025, 100 mg, 40% yield).

As shown in step 7-iii of Scheme 7, tert-butyl 4-(4-(5-(2-amino-5-(1-methyl-1H-pyrazol-4-yl)pyridin-3-yl)-1H-tetrazol-1-yl)-2,3-difluorophenoxy)-cyclohexylmethylcarbamate (Compound 1025, 146 mg, 0.264 mmol) was taken up in 3 mL of DCM and treated with 1M HCl in ethyl ether (1.0 mL). The reaction mixture was warmed to room temperature and stirred for 16 hours. The volatiles were removed under reduced pressure and the resulting white solid was triturated with ethyl ether to provide 3-(1-(4-(4-(methylamino)cyclohexyloxy)-2,3-difluorophenyl)-1H-tetrazol-5-yl)-5-(1-methyl-1H-pyrazol-4-yl)pyridin-2-amine dihydrochloride (Compound 131, 63 mg, 66% yield).

As shown in step 7-iv of Scheme 7, 3-(1-(4-(4-(methylamino)cyclohexyloxy)-2,3-difluorophenyl)-1H-tetrazol-5- yl)-5-(1-methyl-1H-pyrazol-4-yl)pyridin-2-amine dihydrochloride (Compound 131, 60 mg, 0.108 mmol) was dissolved in 30 mL of THF. After the addition of $K_2CO_3$ (15 mg, 0.108 mmol), methyl iodide (8.5 µL, 0.108 mmol) was added. The reaction mixture was stirred for 30 minutes at room temperature, diluted with water (30 mL), and extracted with EtOAc (2×20 mL). The combined organics were washed with water (2×30 mL), washed with brine (20 mL), dried over sodium sulfate, filtered, and concentrated under reduced pressure. The residue was purified by silica gel chromatography (1% methanol/$CHCl_3$ containing 6 drops of conc. $NH_4OH$ for every 100 mL of eluant) to provide 3-(1-(4-(4-(dimethylamino)cyclohexyloxy)-2,3-difluorophenyl)-1H-tetrazol-5-yl)-5-(1-methyl-1H-pyrazol-4-yl)pyridin-2-amine (Compound 177, 37.5 mg, 70% yield).

In an alternative procedure, secondary amines such as Compound 131 can be treated with paraformaldehyde/NaBH(OAc)$_3$ to produce the corresponding N-methylated tertiary amines.

Using the appropriate hydroxyl compound and boronate, the following compounds were prepared by a procedure similar to that as described above in Example 7: Compounds 3, 106-109, 112-130, 139-147, 155-156, 172-173, and 178-179.

EXAMPLE 8

Preparation of 3-(1-(2,3-difluoro-4-(piperazin-1-yl)phenyl)-1H-tetrazol-5-yl)-5-(1-methyl-1H-pyrazol-4-yl)pyridin-2-amine (Compound 97)

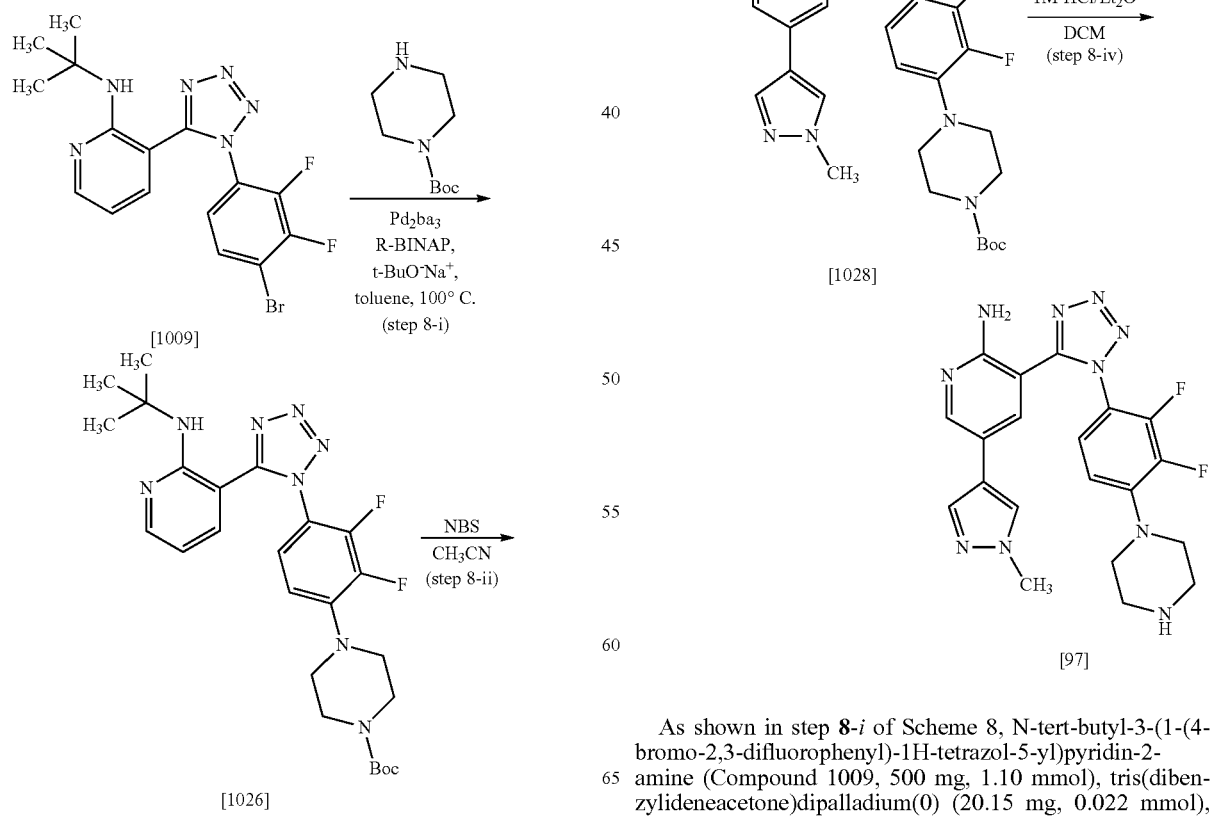

As shown in step 8-i of Scheme 8, N-tert-butyl-3-(1-(4-bromo-2,3-difluorophenyl)-1H-tetrazol-5-yl)pyridin-2-amine (Compound 1009, 500 mg, 1.10 mmol), tris(dibenzylideneacetone)dipalladium(0) (20.15 mg, 0.022 mmol), Boc-piperazine (266 mg, 1.43 mmol), (R)-(+)-(1,1'-binaphthalene-2,2'-diyl)bis(diphenylphosphine) (68.5 mg, 0.11 mmol), sodium-t-butoxide (148 mg, 1.54 mmol) in toluene was heated at 100° C. for 24 hours. After cooling, the reaction mixture was diluted with EtOAc, washed with water, washed with brine, dried over sodium sulfate, filtered, and concentrated under reduced pressure. The residue was purified by silica gel chromatography (30% EtOAc/hexane) to provide tert-butyl 4-(4-(5-(2-(tert-butylamino)pyridin-3-yl)-1H-tetrazol-1-yl)-2,3-difluorophenyl)piperazine-1-carboxylate (Compound 1026, 350 mg, 62% yield): ESMS (M+1)=515.2.

As shown in step 8-*ii* of Scheme 8, tert-butyl 4-(4-(5-(2-(tert-butylamino)pyridin-3-yl)-1H-tetrazol-1-yl)-2,3-difluorophenyl)piperazine-1-carboxylate (Compound 1026, 350 mg, 0.68 mmol) was dissolved in 5 mL of acetonitrile and N-bromosuccinimide (121 mg, 0.68 mmol) was added. The reaction mixture was stirred for 1 hour and 1M $Na_2S_2O_3$ (aq) was added. The mixture was extracted with EtOAc and the combined organics were washed with brine, dried over sodium sulfate, filtered, and concentrated under reduced pressure. The residue was purified by silica gel chromatography (30% EtOAc/hexane) to provide tert-butyl 4-(4-(5-(2-(tert-butylamino)-5-bromopyridin-3-yl)-1H-tetrazol-1-yl)-2,3-difluorophenyl)piperazine-1-carboxylate (Compound 1027, 290 mg, 72% yield): ESMS (M+1)=595.2.

As shown in step 8-*iii* of Scheme 8, tert-butyl 4-(4-(5-(2-(tert-butylamino)-5-bromopyridin-3-yl)-1H-tetrazol-1-yl)-2,3-difluorophenyl)piperazine-1-carboxylate (Compound 1027, 100 mg, 0.169 mmol), 1-methyl-4-(4,4,5,5-tetramethyl-1,3,2-dioxaborolan-2-yl)-1H-pyrazole (42.1 mg, 0.20 mmol), 1.2M $NaHCO_3$ (aq) (0.14 mL) and 1 mL of DMF were flushed with nitrogen gas for 20 minutes. $PdCl_2(dppf)$ (123 mg, 0.17 mmol) was added and the reaction mixture flushed with nitrogen gas for an additional 20 minutes, followed by heating at 120° C. for 10 minutes. After cooling, the mixture was diluted with EtOAc, washed with water, washed with brine, dried over sodium sulfate, filtered, and concentrated under reduced pressure. The residue was purified by silica gel chromatography (0-50% EtOAc/hexanes to produce tert-butyl 4-(4-(5-(2-(tert-butylamino)-5-(1-methyl-1H-pyrazol-4-yl)pyridin-3-yl)-1H-tetrazol-1-yl)-2,3-difluorophenyl)piperazine-1-carboxylate (Compound 1028, 95 mg, 95% yield): ESMS (M+1)=595.3.

As shown in step 8-*iv* of Scheme 8, tert-butyl 4-(4-(5-(2-(tert-butylamino)-5-(1-methyl-1H-pyrazol-4-yl)pyridin-3-yl)-1H-tetrazol-1-yl)-2,3-difluorophenyl)piperazine-1-carboxylate (Compound 1028, 95 mg, 0.16 mmol) was treated with 5 mL of 5.5 M HCl/isopropanol and the reaction mixture stirred for 10 hours at 70° C. After cooling, the resulting solid was collected by filtration to provide 3-(1-(2,3-difluoro-4-(piperazin-1-yl)phenyl)-1H-tetrazol-5-yl)-5-(1-methyl-1H-pyrazol-4-yl)pyridin-2-amine (Compound 97, 26 mg, 32% yield).

Using the appropriate boronate, the following compounds were prepared by a procedure similar to that as described above in Example 8: Compounds 98-99.

TABLE 2

Analytical Chararacterization Data for Compounds of Formula I (blank cells indicate that the test was not performed)

| Cmpnd. No. | MS (M + H) | $^1$H-NMR (300 MHz, unless indicated otherwise) NMR peaks given as δ values in ppm |
|---|---|---|
| 1 | 511.50 | |
| 2 | 442.30 | (DMSO-$d_6$): 10.15 (s, 1H) 8.40 (d, J = 2.3 Hz) 1H) 7.96 (s, 1H) 7.73-7.64 (m, 2H) 7.59 (s, 1H) 7.41-7.35 (m, 1H) 6.87 (s, 1H) 4.58-4.55 (m, 2H) 3.88 (s, 3H) 3.58 (t, J = 4.5 Hz, 2H) 2.86 (d, J = 4.8 Hz, 6H) |
| 3 | 454.19 | |
| 4 | 484.49 | (methanol-$d_4$): 8.33 (d, J = 2.2 Hz, 1H), 8.11 (d, J = 2.1 Hz, 1H), 7.91 (s, 1H), 7.68-7.62 (m, 1H), 7.53 (d, J = 0.7 Hz, 1H), 7.40-7.37 (m, 1H), 4.67 (t, J = 4.7 Hz, 2H), 4.08 (d, J = 11.3 Hz, 2H), 3.90 (s, 3H), 3.86 (s, 2H), 3.75 (t, J = 4.7 Hz, 2H), 3.65-3.59 (m, 2H) and 3.38 (m, 2H) |
| 5 | 482.35 | (methanol-$d_4$): 8.33 (d, J = 2.2 Hz, 1H), 8.08 (d, J = 2.2 Hz, 1H), 7.91 (s, 1H), 7.68-7.62 (m, 1H), 7.52 (d, J = 0.7 Hz, 1H), 7.39-7.33 (m, 1H), 4.63 (t, J = 4.8 Hz, 2H), 3.90 (s, 3H), 3.66-3.55 (m, 4H), 3.15-3.08 (m, 2H), 2.01-1.78 (m, 5H), 1.96 (s, H), 1.90-1.83 (m, H), 1.78 (d, J = 3.8 Hz, H) and 1.58 (m, 1H) |
| 6 | 468.35 | (methanol-$d_4$): 8.33 (d, J = 2.2 Hz, 1H), 8.07 (d, J = 2.2 Hz, 1H), 7.90 (s, 1H), 7.68-7.62 (m, 1H), 7.51 (s, 1H), 7.36 (m, 1H), 4.59 (t, J = 4.8 Hz, 2H), 3.90 (s, 3H), 3.77 (m, 4H), 3.25-3.21 (m, 2H) and 2.24-2.05 (m, 4H) |
| 7 | 456.29 | (methanol-$d_4$): 8.35 (d, J = 2.2 Hz, 1H), 8.06 (d, J = 2.1 Hz, 1H), 7.98 (s, 1H), 7.64 (m, 1H), 7.53 (s, 1H), 7.36 (m, 1H), 4.61 (t, J = 4.8 Hz, 2H), 4.19 (q, J = 7.3 Hz, 2H), 3.70 (t, J = 4.8 Hz, 2H), 3.02 (s, 6H) and 1.45 (t, J = 7.3 Hz, 3H) ppm |
| 8 | 498.33 | (methanol-$d_4$): 8.36 (d, J = 2.1 Hz, 1H), 8.05 (d, J = 2.1 Hz, 1H), 8.00 (s, 1H), 7.65 (m, 1H), 7.52 (s, 1H), 7.38 (m, 1H), 4.62 (t, J = 4.8 Hz, 2H), 4.19 (t, J = 7.3 Hz, 2H), 3.72 (t, J = 4.7 Hz, 2H), 3.05 (d, J = 5.0 Hz, 6H), 1.77-1.72 (m, 2H), 1.60-1.49 (m, 1H) and 0.96 (d, J = 6.6 Hz, 6H) |
| 9 | 470.30 | (methanol-$d_4$): 8.36 (d, J = 2.1 Hz, 1H), 8.14 (d, J = 2.1 Hz, 1H), 7.99 (s, 1H), 7.65 (m, 1H), 7.56 (s, 1H), 7.37 (m, 1H), 4.61 (t, J = 4.8 Hz, 2H), 4.12 (t, J = 7.0 Hz, 2H), 3.70 (t, J = 4.7 Hz, 2H), 3.02 (s, 6H), 1.87 (q, J = 7.2 Hz, 2H) and 0.89 (t, J = 7.4 Hz, 3H) |
| 10 | 484.30 | (methanol-$d_4$): 8.36 (d, J = 2.2 Hz, 1H), 8.08 (d, J = 2.1 Hz, 1H), 7.97 (s, 1H), 7.67-7.61 (m, 1H), 7.54 (s, 1H), 7.36 (dd, J = 2.0, 17.1 Hz, H), 7.36 (m, 1H), 4.61 (t, J = 4.8 Hz, 2H), 3.95 (d, J = 7.3 Hz, 2H), 3.70 (t, J = 4.8 Hz, 2H), 3.03 (d, J = 5.4 Hz, 6H), 2.16 (t, J = 6.8 Hz, 1H) and 0.90 (d, J = 6.7 Hz, 6H) |

TABLE 2-continued

Analytical Chararacterization Data for Compounds of Formula I (blank cells indicate that the test was not performed)

| Cmpnd. No. | MS (M + H) | $^1$H-NMR (300 MHz, unless indicated otherwise) NMR peaks given as δ values in ppm |
|---|---|---|
| 11 | 492.40 | |
| 12 | 538.40 | |
| 13 | 530.20 | |
| 14 | 480.30 | |
| 15 | 508.40 | |
| 16 | 479.40 | |
| 17 | 506.40 | |
| 18 | 534.30 | |
| 19 | 506.40 | |
| 20 | 524.40 | |
| 21 | 524.40 | |
| 22 | 516.30 | |
| 23 | 466.30 | |
| 24 | 465.30 | |
| 25 | 520.30 | |
| 26 | 520.30 | |
| 27 | 494.40 | |
| 28 | 510.50 | |
| 29 | 561.40 | |
| 30 | 492.40 | |
| 31 | 512.30 | (methanol-d$_4$): 8.34 (d, J = 2.3 Hz, 1H), 7.81 (s, 1H), 7.54-7.48 (m, 2H), 7.43 (s, 1H), 7.26 (dd, J = 2.0, 17.0 Hz, 1H), 4.43-4.31 (m, 3H), 4.06 (dt, J = 11.5, 3.6 Hz, 2H), 3.61-3.52 (m, 2H), 2.86 (t, J = 5.4 Hz, 2H), 2.38 (d, J = 8.7 Hz, 6H), 2.07-2.00 (m, 4H) and 0.01 (d, J = 3.2 Hz, H) |
| 32 | 442.0 | |
| 33 | 484.40 | (methanol-d$_4$): 8.33 (d, J = 2.3 Hz, 1H), 7.71 (s, 1H), 7.47 (dd, J = 2.3, 4.2 Hz, 2H), 7.40 (s, 1H), 7.22 (m, 1H), 4.26 (t, J = 6.2 Hz, 2H), 3.91 (d, J = 7.3 Hz, 2H), 2.76 (t, J = 7.2 Hz, 2H), 2.40 (s, 3H), 2.15-2.03 (m, 3H), 0.89 (d, J = 6.7 Hz, 6H) |
| 34 | 470.0 | |
| 35 | 473.0 | |
| 36 | 495.0 | |
| 37 | 468.0 | |
| 38 | 498.0 | |
| 39 | 444.0 | |
| 40 | 439.0 | |
| 41 | 468.0 | |
| 42 | 438.0 | |
| 43 | 481.0 | |
| 44 | 494.0 | |
| 45 | 472.0 | |
| 46 | 458.0 | |
| 47 | 456.0 | |
| 48 | 498.0 | |
| 49 | 484.00 | |
| 50 | 847.0 | |
| 51 | 509.0 | |
| 52 | 482.0 | |
| 53 | 512.0 | |
| 54 | 458.0 | |
| 55 | 453.0 | |
| 56 | 482.0 | |
| 57 | 452.0 | |
| 58 | 495.0 | |
| 59 | 508.0 | |
| 60 | 486.0 | |
| 61 | 472.0 | |
| 62 | 458.50 | |
| 63 | 500.30 | |
| 64 | 532.30 | |
| 65 | 482.30 | |
| 66 | 563.40 | |
| 67 | 523.40 | |
| 68 | 510.40 | |
| 69 | 536.30 | |
| 70 | 536.30 | |
| 71 | 508.30 | |
| 72 | 486.30 | |
| 73 | 512.30 | |
| 74 | 526.50 | |
| 75 | 498.40 | |
| 76 | 512.40 | |
| 77 | 526.50 | |

TABLE 2-continued

Analytical Chararacterization Data for Compounds of Formula I (blank cells indicate that the test was not performed)

| Cmpnd. No. | MS (M + H) | $^1$H-NMR (300 MHz, unless indicated otherwise) NMR peaks given as δ values in ppm |
|---|---|---|
| 78 | 486.30 | |
| 79 | 518.30 | |
| 80 | 468.40 | |
| 81 | 549.40 | |
| 82 | 509.40 | |
| 83 | 508.30 | |
| 84 | 492.70 | |
| 85 | 482.60 | |
| 86 | 466.70 | |
| 87 | 468.60 | |
| 88 | 455.60 | |
| 89 | 494.40 | |
| 90 | 468.30 | |
| 91 | 444.20 | |
| 92 | 508.40 | |
| 93 | 481.30 | |
| 94 | 498.00 | |
| 95 | 510.40 | |
| 96 | 496.40 | |
| 97 | 439.19 | (methanol-d$_4$): 8.37 (d, J = 2.0 Hz, 1H), 8.15 (d, J = 2.0 Hz, 1H), 7.97 (s, 1H), 7.60-7.55 (m, 2H), 7.22 (d, J = 8.1 Hz, 1H), 3.93 (s, 3H), 3.54-3.51 (m, 4H) and 3.44-3.41 (m, 4H) |
| 98 | 441.40 | (methanol-d$_4$): 8.59 (d, J = 2.2 Hz, 1H), 8.35 (d, J = 1.9 Hz, 1H), 7.72-7.68 (m, 3H), 7.35 (d, J = 1.3 Hz, 2H), 5.44 (s, 1H), 3.81 (d, J = 8.3 Hz, 3H) and 3.66-3.56 (m, 6H) |
| 99 | 455.20 | (methanol-d$_4$): 8.34 (d, J = 2.2 Hz, 1H), 8.01 (d, J = 2.2 Hz, 1H), 7.58 (d, J = 1.8 Hz, 1H), 7.24 (s, 1H), 7.01 (d, J = 3.6 Hz, 1H), 6.78 (dd, J = 0.9, 3.5 Hz, 1H), 3.56-3.52 (m, 4H), 3.46-3.43 (m, 4H) and 2.48 (s, 3H) |
| 100 | 442.3 | (400 MHz, CDCl$_3$): 8.30 (d, J = 1.5 Hz, 1H), 7.34-7.32 (m, 2H), 7.24 (s, 1H), 6.75 (dd, J = 2.4 Hz, 9.3 Hz, 2H), 6.34 (br.s, exchangable proton, 2H), 4.11 (t, J = 4.5 Hz, 2H), 3.90 (s, 3H), 2.77 (t, J = 4.2 Hz, 2H), 2.34 (s, 6H) |
| 101 | 456.3 | (400 MHz, CDCl$_3$): 8.31 (d, J = 1.6 Hz, 1H), 7.38 (br. s, 1H), 7.34 (d, J = 2.8 Hz, 1H), 7.24 (s, 1H), 6.76 (dd, J = 9.6, 2.4 Hz, 2H), 6.40 (br.s, exchanged with D$_2$O, 2H), 4.15 (q, J = 7.2 Hz, 2H), 4.12 (t, J = 5.6 Hz, 2H), 2.77 (t, J = 5.6 Hz, 2H), 2.34 (s, 6H), 1.49 (t, J = 4.2 Hz, 3H) |
| 102 | 444.3 | (400 MHz, CDCl$_3$): 8.45 (d, J = 1.6 Hz, 1H), 7.45 (d, J = 1.5 Hz, 1H), 7.34 (dd, J = 4.8, 2.8 Hz, 1H), 7.03 (dd, J = 2.8, 1.6 Hz, 1H), 6.95 (dd, J = 3.6, 0.9 Hz, 1H), 6.76 (dd, J = 9.6, 2.4 Hz, 2H), 6.43 (br.s, exchanged with D$_2$O, 2H), 4.12 (t, J = 3.9 Hz, 2H), 2.77 (t, J = 4.2 Hz, 2H), 2.35 (s, 6H) |
| 103 | 512.2 | (400 MHz, CDCl$_3$): 8.31 (d, J = 2.0 Hz, 1H), 7.41 (s, 1H), 7.35 (d, J = 2.4 Hz, 1H), 7.27 (d, J = 0.8 Hz, 1H), 6.75 (dd, J = 12.4, 3.2 Hz, 2H), 6.35 (br.s, exchanged with D$_2$O, 2H), 4.36-4.28 (m, 1H), 4.12 (t, J = 5.6 Hz, 4H), 3.54 (dt, J = 11.6, 2.8 Hz, 2H), 2.78 (t, J = 5.6 Hz, 2H), 2.35 (s, 6H), 2.11-1.99 (m, 4H) |
| 104 | 444.1 | (400 MHz, CDCl$_3$): 8.46 (d, J = 2.4 Hz, 1H), 7.45 (d, J = 2.0 Hz, 1H), 7.17 (dd, J = 5.2, 0.8 Hz, 1H), 7.0 (dd, J = 5.2, 3.6 Hz. 1H), 6.93 (dd, J = 5.2, 3.6 Hz, 1H), 6.77 (dd, J = 3.6, 1.2 Hz, 2H), 6.53 (br.s, exchanged with D$_2$O, 2H), 4.13 (t, J = 5.6 Hz, 2H), 2.78 (t, J = 5.6 Hz, 2H), 2.35 (s, 6H) |
| 105 | 458.1 | (400 MHz, CDCl$_3$): 8.43 (d, J = 2.4 Hz, 1H), 7.41 (d, J = 2.4 Hz, 1H), 6.79-6.74 (m, 4H), 6.52 (br.s, exchanged with D$_2$O, 2H), 4.13 (t, J = 5.6 Hz, 2H), 2.78 (t, J = 5.6 Hz, 2H), 2.35 (s, 6H), 2.29 (s, 3H) |
| 106 | 482.20 | (methanol-d$_4$): 8.31 (d, J = 2.3 Hz, 1H), 7.73 (s, 1H), 7.53-7.45 (m, 2H), 7.39 (d, J = 0.5 Hz, 1H), 7.23 (dd, J = 2.0, 17.1 Hz, 1H), 4.20-4.05 (m, 4H), 3.57 (td, J = 7.2, 4.0 Hz, 1H), 3.00-2.92 (m, 2H), 2.08-1.97 (m, 1H), 1.92-1.76 (m, 4H), 1.67-1.56 (m, 1H), 0.89 (t, J = 7.4 Hz, 3H) and 0.00 (s, H) |
| 107 | 482.20 | (methanol-d$_4$): 8.33-8.31 (m, 1H), 7.74-7.70 (m, 1H), 7.52-7.43 (m, 2H), 7.38-7.36 (m, 1H), 7.26-7.20 (m, 1H), 4.21-4.05 (m, 4H), 3.14-2.87 (m, 3H), 2.82-2.62 (m, 2H), 2.10-1.99 (m, 1H), 1.85 (td, J = 14.4, 7.2 Hz, 2H), 1.69-1.60 (m, 1H), 0.89 (td, J = 7.4, 3.5 Hz, 3H) and 0.01 (d, J = 3.3 Hz, H) |
| 108 | 482.20 | (methanol-d$_4$): 8.33-8.31 (m, 1H), 7.74-7.70 (m, 1H), 7.52-7.43 (m, 2H), 7.38-7.36 (m, 1H), 7.26-7.20 (m, 1H), 4.21-4.05 (m, 4H), 3.14-2.87 (m, 3H), 2.82-2.62 (m, 2H), 2.10-1.99 (m, 1H), 1.85 (td, J = 14.4, 7.2 Hz, 2H), 1.69-1.60 (m, 1H), 0.89 (td, J = 7.4, 3.5 Hz, 3H) and 0.01 (d, J = 3.3 Hz, H) |
| 109 | 482.20 | (methanol-d$_4$): 8.31 (d, J = 2.3 Hz, 1H), 7.73 (s, 1H), 7.53-7.45 (m, 2H), 7.39 (d, J = 0.5 Hz, 1H), 7.23 (dd, J = 2.0, 17.1 Hz, 1H), 4.20-4.05 (m, 4H), 3.57 (td, J = 7.2, 4.0 Hz, 1H), 3.00-2.92 (m, |

TABLE 2-continued

Analytical Chararacterization Data for Compounds of Formula I (blank cells indicate that the test was not performed)

| Cmpnd. No. | MS (M + H) | ¹H-NMR (300 MHz, unless indicated otherwise) NMR peaks given as δ values in ppm |
|---|---|---|
|  |  | 2H), 2.08-1.97 (m, 1H), 1.92-1.76 (m, 4H), 1.67-1.56 (m, 1H), 0.89 (t, J = 7.4 Hz, 3H) and 0.00 (s, H) |
| 110 | 470.3 | (400 MHz, CDCl₃): 8.32 (d, J = 2.0 Hz, 1H), 7.39 (s, 1H), 7.35 (d, J = 1.6 Hz, 1H), 7.26 (s, 1H), 6.75 (dd, J = 12.0 Hz, 2.4 Hz, 2H), 6.35 (s, exchanged with D₂O, 2H), 4.51-4.44 (m, 1H), 4.11 (t, J = 5.6 Hz, 2H), 2.77 (t, J = 5.2 Hz, 2H), 2.34 (s, 6H), 1.51 (d, J = 6.8 Hz, 6H) |
| 111 | 496.3 | (400 MHz, CDCl₃): 8.31 (d, J = 2.4 Hz, 1H), 7.39 (s, 1H), 7.35 (d, J = 2.4 Hz, 1H), 7.26 (s, 1H), 6.75 (dd, J = 12.0, 3.2 Hz, 2H), 6.35 (s, exchanged wiht D₂O, 2H), 4.65-4.58 (m, 1H), 4.11 (t, J = 6.0 Hz, 2H), 2.77 (t, J = 5.2 Hz, 2H), 2.35 (s, 6H), 2.21-2.13 (m, 2H), 2.03-1.95 (m, 2H), 1.91-1.82 (m, 2H), 1.77-1.68 (m, 2H). |
| 112 | 468.30 | (CDCl₃): 9.03 (br. hump, exchanged with D₂O, 1H), 8.72 (br. hump, exchanged with D₂O, 1H), 8.48 (d, J = 2.1 Hz, 1H), 8.12 (d, J = 2.4 Hz, 1H), 8.05 (s, 1H), 7.69 (s, 1H), 7.63 (br. td, J = 9.6, 1.8 Hz, 1H), 7.33 (br. t, J = 8.1 Hz, 1H), 4.09 (d, J = 6.0 Hz, 2H), 3.83 (s, 3H), 3.30 (br. d, J = 12.0 Hz, 2H), 2.95-2.80 (m, 2H), 2.15-2.05 (m, 4H), 1.90-1.70 (m, 2H) |
| 113 | 524.40 | (CDCl₃): 9.14 (br. hump, exchanged with D₂O, 1H), 8.83 (br. hump, exchanged with D₂O, 1H), 8.52 (d, J = 2.1 Hz, 1H), 8.27 (d, J = 2.4 Hz, 1H), 8.18 (s, 1H), 7.75 (s, 1H), 7.60 (br. td, J = 9.6, 1.8 Hz, 1H), 7.33 (t, J = 8.1 Hz, 1H), 4.13-4.10 (m, 4H), 3.30 (br. d, J = 12.0 Hz, 2H), 2.95 (br q, J = 12.0, 2H), 2.15-2.05 (m, 1H), 1.65 (q, J = 6.9 Hz, 2H) 1.90-1.70 (m, 5H), 0.88 (d, J = 6.8 Hz, 6H) |
| 114 | 470.20 | (CDCl₃): 9.14 (br. hump, exchanged with D₂O, 1H), 8.83 (br. hump, exchanged with D₂O, 1H), 8.51 (d, J = 2.1 Hz, 1H), 7.84 (s, 1H), 7.65 (br. td, J = 9.6, 1.8 Hz, 1H), 7.53 (d, J = 5.1 Hz, 1H), 7.40 (d, J = 8.4 Hz, 1H), 7.32 (d, J = 3.0 Hz, 1H), 7.01 (dd, J = 5.1, .4.8 Hz, 1H), 4.09 (d, J = 6.3 Hz, 2H), 3.30 (br. d, J = 12.0 Hz, 2H), 2.95 (br q, J = 12.0, 2H), 2.15-2.05 (m, 1H), 1.90-1.70 (m, 2H), 1.59-1.48 (m, 2H) |
| 115 | 538.40 | (CDCl₃): 9.03 (br. hump, exchanged with D₂O, 1H), 8.70 (br. hump, exchanged with D₂O, 1H), 8.51 (d, J = 2.1 Hz, 1H), 8.23 (s, 1H), 8.16 (s, 1H), 7.74 (s, 1H), 7.65 (br. td, J = 9.6, 1.8 Hz, 1H), 7.34 (br. t, J = 8.7 Hz, 1H), 4.42-4.35 (m, 1H), 4.09 (d, J = 9.3 Hz, 2H), 3.97 (br. d, J = 12.0 Hz, 2H), 3.47 (td, J = 12.0, 2.1 Hz, 2H), 2.84-2.70 (br. m, 2H), 2.0-1.70 (m, 8H), 1.57-1.46 (m, 2H) |
| 116 | 490.22 |  |
| 117 | 450.19 |  |
| 118 | 519.79 |  |
| 119 | 441.33 |  |
| 120 | 496.16 |  |
| 121 | 482.14 |  |
| 122 | 456.14 |  |
| 123 | 468.10 |  |
| 124 | 494.22 |  |
| 125 | 454.19 |  |
| 126 | 451.18 |  |
| 127 | 451.21 |  |
| 128 | 552.40 | (DMSO-d₆): 8.99 (br s, exchanged with D₂O, 2H), 8.53 (d, J = 1.5 Hz, 1H), 8.24 (s, 1H), 8.19 (br s, 1H), 7.72 (s, 1H), 7.65 (br. t, J = 9.3 Hz, 1H), 7.38 (br. t, J = 9.3 Hz, 1H), 4.81 (br s, 1H), 4.42-4.35 (m, 1H), 3.95 (br d, J = 11.4 Hz, 2H), 3.47 (dt, J = 11.4, 1.5 Hz, 2H), 3.04 (br s, 1H), 2.56 (s, 3H), 2.00-1.85 (m, 8H), 1.73-.160 (m, 4H) |
| 129 | 484.30 | (DMSO-d₆): 8.88 (br s, exchanghed with D₂O, 2H), 8.53 (d, J = 2.1 Hz, 1H), 7.68 (td J = 9.6, ~2.0 Hz, 1H), 7.60 (br s, 1H), 7.48 (d, J = 5.1 Hz, 1H), 7.43 (t, J = 8.1 Hz, 1H), .725 (d, J = 3.9 Hz, 1H), 7.08 (dd, J = 4.8, 3.9 Hz, 1H), 4.86 (br s, 1H), 3.05 (br hump, 1H), 2.53 (s, 3H,) 2.03-1.90 (m, 4H), 1.74-1.60 (m, 4H) |
| 130 | 538.40 | (DMSO-d₆): 8.92 (br s, exchanhed with D₂O, 2H), 8.48 (d, J = 2.1 Hz, 1H), 8.14 (s, 1H), 8.11 (s, 1H), 7.66 (s, 1H), 7.62 (t, J = 8.1 Hz, 1H), 7.38 (t, J = 8.1 Hz, 1H), 4.82 (s, 1H), 4.10 (t, J = 6.6 Hz, 2H), 3.05 (br s, 1H), 2.50 (s, 3H), 2.00-1.90 (m, 4H), 1.73-1.60 (m, 6H), 1.49-1.40 (m, 1H), 0.89 (d, J = 6.9 Hz, 6H) |
| 131 | 482.30 | (DMSO-d₆): 8.43 (d, J = 2.1 Hz, 1H), 8.06 (d, J = 1.8 Hz, 1H), 8.02 (br s, 1H), 7.68-7.60 (m, 2H), 7.38 (t, J = 8.1 Hz, 1H), 4.82 (s, 1H), 3.83 (s, 3H), 3.05-3.00 (br hump, 1H), 2.56 (s, 3H), 2.00-1.90 (m, 4H), 1.73-1.64 (m, 4H) |
| 132 | 472.30 | (CDCl₃): 8.62 (d, J = 2.4 Hz, 1H), 7.36 (d, J = 2.4 Hz, 1H), 7.24-7.17 (series of m, 2H), 7.019-7.17 (series of m 3H), 6.54 (br s, exchanged with D₂O, 2H), 4.20 (t, J = 6.3 Hz, 2H), 2.36 (ddas t, J = 6.6 Hz, 2H), 2.25 (s, 6H), 1.98-1.88 (m, 2H), 1.74-1.64 (m, 2H) |
| 133 | 526.50 | (CDCl₃): 8.31 (d, J = 2.1 Hz, 1H), 7.34 (s, 1H), 7.28-7.26 (m, 3H), 7.19 (s, 1H), 6.97 (t, J = 9.3 Hz, 1H), 6.35 (s, 2H), 4.18 (t, J = 6.3 Hz, |

TABLE 2-continued

Analytical Chararacterization Data for Compounds of Formula I (blank cells indicate that the test was not performed)

| Cmpnd. No. | MS (M + H) | $^1$H-NMR (300 MHz, unless indicated otherwise) NMR peaks given as δ values in ppm |
|---|---|---|
| | | 2H), 4.10 (t, J = 7.5 Hz, 2H), 2.42 (t, J = 7.2 Hz, 2H), 2.31 (d, J = 3.9 Hz, 5H), 1.98-1.89 (m, 3H), 1.79-1.70 (m, 4H), 1.61-1.55 (m, 1H), 0.96 (d, J = 6.6 Hz, 5H) |
| 134 | 512.40 | (DMSO-d$_6$): 8.96 (br s, exchanged with D$_2$O, 2H), 8.52 (d, J = 1.5 Hz, 1H), 8.28 (s, 1H), 8.17 (s, 1H), 8.06 (br. s, 2H), 7.76 (s, 1H), 7.63 (t, J = 7.6 Hz, 1H), 7.32 (t, J = 8.1 Hz, 1H), 4.20 (t, J = 5.5 Hz, 2H), 4.10 (t, J = 7.2 Hz, 2H), 2.93 (br d, 2H), 2.59 (d, J = 11.1 Hz, 3H), 1.82-1.80 (m, 4H), 1.69 (q, J = 6.9 Hz, 2H), 1.49-1.45 (m, 1H), 0.90 (d, J = 6.6 Hz, 6H) |
| 135 | 458.30 | (DMSO-d$_6$): 8.96 (br s, 2H), 8.52 (d, J = 2.1 Hz, 1H), 7.74 (br s, 1H), 7.67 (t, J = 7.3 Hz, 1H), 7.51 (d, J = 4.8 Hz, 1H), 7.38-7.29 (m, 2H), 7.10 (br s, 1H), 7.09 (t, J = 5.2 Hz, 1H), 4.22 (t, J = 5.5 Hz, 2H), 2.92 (br.t, J = 5.5 Hz, 2H), 2.53 (s, 3H), 1.83-1.76 (m, 4H) |
| 136 | 470.30 | (CDCl$_3$): 8.30 (d, J = 1.8 Hz, 1H), 7.32 (s, 1H), 7.28-7.22 (m, 2H), 7.19 (s, 1H), 6.96 (dt, J = 6.9, 1.8 Hz, 1H), 6.35 (s, exchanged with D$_2$O, 2H), 4.18 (t, J = 6.6 Hz, 2H), 3.89 (s, 3H), 2.38 (t, J = 7.2 Hz, 2H), 2.26 (s, 6H), 1.97-1.88 (m, 2H), 1.75-1.67 (m, 2H) |
| 137 | 456.30 | (DMSO-d$_6$): 8.86 (br.s, exchanged with D$_2$O, 2H), 8.48 (d, J = 2.4 Hz, 1H), 8.14 (s, 1H), 8.06 (s, 1H), 7.70 (s, 1H), 7.65-7.60 (m, 1H), 7.35-7.29 (m, 1H), 4.20 (t, J = 5.1 Hz, 2H), 3.83 (s, 3H), 2.96-2.90 (m, 2H), 2.50 (d, J = 1.8 Hz, 3H), 1.82-1.80 (m, 4H) |
| 138 | 526.40 | (DMSO-d$_6$): 8.87 (br.s, exchanged with D$_2$O, 2H), 8.52 (d, J = 2.1 Hz, 1H), 8.24-8.21 (m, 2H), 7.77 (s, 1H), 7.63 (dt, J = 9.6, 1.8 Hz, 1H), 7.35-7.29 (m, 1H), 4.40-4.34 (m, 1H), 4.20 (t, J = 5.4 Hz, 2H), 3.98-3.93 (m, 2H), 3.47 (dt, J = 11.4, 1.8 Hz, 2H), 2.94-2.90 (m, 2H), 2.50 (d, J = 1.8 Hz, 3H), 2.01-1.80 (m, 8H) |
| 139 | 496.40 | (DMSO-d$_6$, about 70:30 mixture of cis and trans isomers, data reported for major diasteromer): 8.92 (br.s, exchanged with D$_2$O, 2H), 8.47 (d, J = 2.1 Hz, 1H), 8.14 (br.s, 1H), 8.05 (s, 1H), 7.70 (s, 1H), 7.65-7.56 (m, 1H), 7.38-7.31 (m, 1H), 4.09 (d, J = 7.2 Hz, 1H), 3.83 (s, 3H), 3.10 (br.s, 1H), 2.12-2.00 (m, 3H), 1.90 (s, 3H), 1.75-1.61 (series of m, 7H) |
| 140 | 552.50 | (DMSO-d$_6$, about 70:30 mixture of cis and trans isomers, data reported for major diasteromer): 8.50 (d, J = 1.8 Hz, 1H), 8.24-8.22 (m, 1H), 8.16-8.15 (m, 1H), 7.74 (s, 1H), 7.65-7.59 (m, 1H), 7.38-7.28 (m, 1H), 4.13-4.08 (m, 3H), 3.09 (br.s, 1H), 2.50 (d, J = 1.8 Hz, 3H), 2.12-2.00 (m, 2H), 1.91 (s, 2H), 1.77-1.54 (m, 8H), 1.51-1.40 (m, 1H), 0.89 (d, J = 6.6 Hz, 6H) |
| 141 | 498.30 | (DMSO-d$_6$, about 70:30 mixture of cis and trans isomers, data reported for major diasteromer): 8.97 (br.s, exchanged with D$_2$O, 2H), 8.53 (d, J = 2.4 Hz, 1H), 7.76 (d, J = 1.8 Hz, 1H), 7.71-7.63 (m, 1H), 7.52-7.48 (m, 1H), 7.43-7.35 (m, 1H), 7.30 (d, J = 3.6 Hz, 1H), 7.10-7.07 (m, 1H), 4.13 (d, J = 7.2 Hz, 1H), 4.03 (d, J = 6.3 Hz, 1H), 3.10 (br.s, 1H), 2.50 (br.s, 3H), 2.12-1.55 (m, 8H) |
| 142 | 566.50 | (DMSO-d$_6$, about 70:30 mixture of cis and trans isomers, data reported for major diasteromer): 9.01 (br.s, exchanged with D$_2$O, 2H), 8.53 (d, J = 1.8 Hz, 1H), 8.29-8.25 (m, 2H), 7.80 (s, 1H), 7.65-7.60 (m, 1H), 7.39-7.31 (m, 1H), 4.44-4.33 (m, 1H), 4.09 (d, J = 6.9 Hz, 1H), 4.00-3.93 (m, 1H), 3.55-3.44 (m, 2H), 3.09 (br.s, 1H), 2.50 (d, J = 1.8 Hz, 3H), 2.12-1.86 (m, 8H), 1.55 (m, 8H) |
| 143 | 468.30 | (DMSO-d$_6$): 9.19 (br.s, exchanged with protons, 2H), 8.47 (d, J = 1.2 Hz, 1H), 8.11 (s, 1H), 8.05 (s, 1H), 7.69 (s, 1H), 7.65-7.60 (m, 1H), 7.32 (t, J = 8.4 Hz, 1H), 4.22 (t, J = 5.7 Hz, 2H), 3.83 (s, 3H), 3.31-3.07 (m, 3H), 2.80-2.73 (m, 1H), 2.38-2.28 (m, 1H), 2.12-2.07 (m, 1H), 1.90 (s, 2H), 1.61-1.53 (m, 1H) |
| 144 | 524.40 | (DMSO-d$_6$): 9.21 (br.s, exchanged with D$_2$O, 2H), 8.48 (d, J = 1.8 Hz, 1H), 8.17-8.15 (m, 2H), 7.72 (s, 1H), 7.62 (t, J = 7.8 Hz, 1H), 7.32 (t, J = 8.1 Hz, 1H), 4.22 (t, J = 5.4 Hz, 2H), 4.10 (t, J = 7.2 Hz, 2H), 3.34-3.07 (m, 3H), 2.81-2.74 (m, 1H), 2.39-2.28 (m, 1H), 2.12-2.07 (m, 1H), 1.92-1.88 (m, 2H), 1.69-1.42 (m, 4H), 0.89 (d, J = 6.3 Hz, 6H) |
| 145 | 538.40 | (DMSO-d$_6$): 9.15 (br.s, exchanged with D$_2$O, 2H), 8.49 (br.s, 1H), 8.21 (s, 1H), 8.10 (s, 1H), 7.73 (s, 1H), 7.63 (t, J = 8.1 Hz, 1H), 7.33 (t, J = 8.4 Hz, 1H), 4.41-4.33 (m, 1H), 4.22 (t, J = 6.0 Hz, 2H), 3.97-3.93 (m, 2H), 3.47 (t, J = 11.4 Hz, 2H), 3.32-3.17 (m, 2H), 3.09-3.07 (m, 1H), 2.81-2.72 (m, 1H), 2.39-2.28 (m, 1H), 2.13-1.82 (m, 7H), 1.64-1.51 (m, 1H) |
| 146 | 468.30 | (DMSO-d$_6$): 9.54 (br.s, exchanged with D$_2$O, 1H), 9.21 (br.s, exchanged with D$_2$O, 1H), 8.51 (d, J = 2.1 Hz, 1H), 8.27 (d, J = 1.5 Hz, 1H), 8.09 (s, 1H), 7.76 (s, 1H), 7.65 (dt, J = 9.6 Hz, J = 2.1 Hz, 1H), 7.33 (t, J = 7.8 Hz, 1H), 4.30 (t, J = 6.0 Hz, 1H), 3.84 (s, 3H), 3.56-3.51 (m, 1H), 3.22-3.09 (m, 2H), 2.31-2.07 (m, 3H), 2.00-1.83 (m, 3H), 1.65-1.57 (m, 1H) |

TABLE 2-continued

Analytical Chararacterization Data for Compounds of Formula I (blank cells indicate that the test was not performed)

| Cmpnd. No. | MS (M + H) | $^1$H-NMR (300 MHz, unless indicated otherwise) NMR peaks given as δ values in ppm |
|---|---|---|
| 147 | 538.40 | (DMSO-d$_6$): 9.56 (br.s, exchanged with D$_2$O, 1H), 9.23 (br.s, exchanged with D$_2$O, 1H), 8.55 (d, J = 1.8 Hz, 1H), 8.34 (s, 1H), 8.29 (s, 1H), 7.82 (s, 1H), 7.67-7.62 (m, 1H), 7.33 (t, J = 7.8 Hz, 1H), 4.44-4.37 (m, 1H), 4.30 (t, J = 6.0 Hz, 2H), 3.98-3.93 (m, 2H), 3.56-3.44 (m, 2H), 3.56-3.44 (m, 3H), 3.22-3.06 (m, 2H), 2.32-2.08 (m, 2H), 2.01-1.82 (m, 5H), 1.68-1.55 (m, 1H) |
| 148 | 540.40 | (CDCl$_3$): 8.31 (d, J = 2.4 Hz, 1H), 7.37 (s, 1H), 7.29-7.23 (m, 3H), 7.01-6.94 (m, 1H), 6.36 (s, exchanged with D$_2$O, 2H), 4.37-4.26 (m, 1H), 4.19 (t, J = 6.6 Hz, 2H), 4.13-4.09 (m, 2H), 3.54 (td, J = 11.7, 2.7 Hz, 2H), 2.35 (t, J = 7.2 Hz, 2H), 2.24 (s, 6H), 2.09-1.88 (m, 6H), 1.73-1.65 (m, 2H) |
| 149 | 552.2 | (CDCl$_3$): 8.31 (d, J = 2.1 Hz, 1H), 7.38 (s, 1H), 7.26 (s, 2H), 7.15 (s, 1H), 6.97 (t, J = 7.5 Hz, 1H), 6.34 (br.s, exchanged with D$_2$O, 2H), 4.24-4.20 (m, 2H), 4.11 (t, J = 7.2 Hz, 2H), 2.90 (br.s, 6H), 2.00 (br. s, 8H), 1.75 (q, J = 6.9 Hz, 2H), 1.61-1.53 (m, 1H), 0.95 (d, J = 6.6 Hz, 6H) |
| 150 | 552.2 | (CDCl$_3$): 8.32 (d, J = 2.4 Hz, 1H), 7.34 (s, 1H), 7.27-7.24 (m, 2H), 7.20 (s, 1H), 7.04-6.98 (m, 1H), 6.34 (br.s, exchanged with D$_2$O, 2H), 4.23 (t, J = 6.0 Hz, 2H), 4.10 (t, J = 7.2 Hz, 2H), 2.56-2.47 (m, 6H), 2.10 (quintet, J = 7.2 Hz, 2H), 1.74 (q, J = 6.6 Hz, 2H), 1.64-1.53 (m, 6H), 1.50-1.41 (m, 1H), 0.95 (d, J = 6.6 Hz, 6H) |
| 151 | 554.2 | (CDCl$_3$): 8.30 (d, J = 2.1 Hz, 1H), 7.36 (s, 1H), 7.28-7.26 (m, 2H), 7.17 (s, 1H), 7.02-6.96 (m, 1H), 6.35 (br.s, exchanged with D$_2$O, 2H), 4.23 (t, J = 6.3 Hz, 2H), 4.10 (t, J = 7.5 Hz, 2H), 3.72 (t, J = 4.5 Hz, 4H), 2.56 (t, J = 7.2 Hz, 2H), 2.48 (t, J = 4.5 Hz, 4H), 2.07 (t, J = 6.6 Hz, 2H), 1.79-1.72 (m, 2H), 1.62-1.55 (m, 1H), 0.95 (d, J = 6.6 Hz, 6H) |
| 152 | 538.3 | (CDCl$_3$): 8.30 (d, J = 2.1 Hz, 1H), 7.38 (s, 1H), 7.29-7.23 (m, 2H), 7.16 (s, 1H), 7.03-6.97 (m, 1H), 6.34 (br.s, exchanged with D$_2$O, 2H), 4.27 (t, J = 6.3 Hz, 2H), 4.11 (t, J = 7.5 Hz, 2H), 2.93-2.87 (m, 5H), 2.24 (t, J = 6.6 Hz, 2H), 1.95 (s, 4H), 1.79-1.71 (m, 3H), 1.61-1.53 (m, 1H), 0.95 (d, J = 6.6 Hz, 6H) |
| 153 | 566.2 | (CDCl$_3$): 8.30 (d, J = 2.1 Hz, 1H), 7.34 (s, 1H), 7.27-7.26 (m, 2H), 7.19 (s, 1H), 7.00-6.94 (m, 1H), 6.34 (br.s, exchanged with D$_2$O, 2H), 4.18 (t, J = 6.3 Hz, 2H), 4.10 (t, J = 7.2 Hz, 2H), 2.49 (br.s, 6H), 1.94-1.87 (m, 2H), 1.78-1.59 (m, 8H), 1.48-1.47 (m, 2H), 0.95 (d, J = 6.6 Hz, 6H) |
| 154 | 568.2 | (CDCl$_3$): 8.30 (d, J = 2.4 Hz, 1H), 7.36 (s, 1H), 7.27-7.25 (m, 2H), 7.18 (s, 1H), 6.99-6.93 (m, 1H), 6.34 (br.s, exchanged with D$_2$O, 2H), 4.18 (t, J = 6.6 Hz, 2H), 4.10 (t, J = 7.2 Hz, 2H), 3.72 (t, J = 4.2 Hz, 4H), 2.46-2.41 (m, 6H), 1.98-1.89 (qunitet, J = 8.4 Hz, 2H), 1.79-1.69 (m, 4H), 0.95 (d, J = 6.3 Hz, 6H) |
| 155 | 524.40 | (DMSO-d$_6$): 9.46 (br.s, exchanged with D$_2$O 1H), 9.13 (br.s, exchanged with D$_2$O, 1H), 8.50 (d, J = 1.8 Hz, 1H), 8.25 (s, 1H), 8.17 (s, 1H), 7.75 (s, 1H), 8.1-7.9 (br hump, exchanged with D$_2$O, 1H), 7.64 (dt, J = 9.6 Hz, J = 2.1 Hz, 1H), 7.36-7.30 (m, 1H), 4.30 (t, J = 5.7 Hz, 2H), 4.11 (t, J = 7.2 Hz, 2H), 3.57-3.52 (m, 1H), 3.21-3.11 (m, 2H), 2.28-1.97 (m, 3H), 1.95-1.83 (m, 2H), 1.69-1.43 (m, 4H), 0.89 (d, J = 6.6 Hz, 6H). |
| 156 | 552.20 | (CDCl$_3$): 8.31 (d, J = 2.1 Hz, 1H), 7.34 (s, 1H), 7.27-7.21 (m, 2H), 7.19 (s, 1H), 7.02-6.96 (m, 1H), 6.36 (br.s, exchanged with D$_2$O, 2H), 4.67 (br.s, 1H), 4.10 (dd as t, J = 7.2 Hz, 2H), 2.33 (s, 6H), 2.18-2.14 (m, 1H), 1.77-1.52 (m, 11H), 0.95 (d, J = 6.6 Hz, 6H) |
| 157 | 496.0 | (CDCl$_3$): 8.30 (d, J = 2.4 Hz, 1H), 7.34 (s, 1H), 7.29-7.23 (m, 2H), 7.19 (s, 1H), 7.04-6.98 (m, 1H), 6.36 (br.s, exchanged with D$_2$O, 2H), 4.25 (t, J = 6.0 Hz, 2H), 3.89 (s, 3H), 2.71-2.62 (m, 6H), 2.23-2.14 (m, 2H), 1.73-1.69 (m, 4H), 1.53-1.51 (m, 2H) |
| 158 | 481.7 | (CDCl$_3$): 8.30 (d, J = 1.8 Hz, 1H), 7.34 (s, 1H), 7.29-7.23 (m, 2H), 7.19 (s, 1H), 7.04-6.98 (m, 1H), 6.35 (br.s, exchanged with D$_2$O, 2H), 4.27 (t, J = 6.3 Hz, 2H), 3.89 (s, 3H), 2.85-2.73 (m, 6H), 2.23-2.14 (m, 2H), 1.89 (m, 4H) |
| 159 | 510.0 | (CDCl$_3$): 8.29 (d, J = 2.4 Hz, 1H), 7.34 (s, 1H), 7.29-7.24 (m, 2H), 7.16 (s, 1H), 7.00-6.95 (m, 1H), 6.35 (br.s, 2H, exchanged wtith D$_2$O), 4.19 (t, J = 5.7 Hz, 2H), 3.89 (s, 3H), 2.66 (br.s, 6H), 1.94-1.75 (m, 8H), 1.53 (br s, 2H) |
| 160 | 511.7 | (CDCl$_3$): 8.29 (d, J = 2.1 Hz, 1H), 7.34 (s, 1H), 7.28-7.22 (m, 2H), 7.18 (s, 1H), 6.98-6.93 (m, 1H), 6.34 (br.s, exchanged with D$_2$O, 2H), 4.18 (t, J = 6.3 Hz, 2H), 3.89 (s, 3H), 3.72 (dd as t, J = 4.8 Hz, 4H), 2.46-2.41 (m, 6H), 1.96-1.91 (m, 2H), 1.75-1.68 (m, 2H) |
| 161 | 495.8 | (CDCl$_3$): 8.30 (d, J = 2.1 Hz, 1H), 7.33 (s, 1H), 7.28-7.22 (m, 2H), 7.19 (s, 1H), 7.00-6.93 (m, 1H), 6.34 (br.s, exchanged with D$_2$O, 2H), 4.18 (t, J = 9.0 Hz, 2H), 3.89 (s, 3H), 2.62-2.57 (m, 6H), 1.98-1.91 (m, 2H), 1.83-1.73 (m, 6H) |

TABLE 2-continued

Analytical Chararacterization Data for Compounds of Formula I (blank cells indicate that the test was not performed)

| Cmpnd. No. | MS (M + H) | $^1$H-NMR (300 MHz, unless indicated otherwise) NMR peaks given as δ values in ppm |
|---|---|---|
| 162 | 498.2 | (CDCl$_3$): 8.30 (d, J = 1.5 Hz, 1H), 7.35 (s, 1H), 7.29-7.23 (m, 2H), 7.17 (s, 1H), 7.03-6.97 (m, 1H), 6.35 (br.s, exchanged with D$_2$O, 2H), 4.24 (t, J = 6.3 Hz, 2H), 3.89 (s, 3H), 3.72 (dd as t, J = 4.5 Hz, 4H), 2.56 (t, J = 6.9 Hz, 2H), 2.5-2.46 (m, 4H), 2.11-2.03 (m, 2H) |
| 163 | 526.5 | (CDCl$_3$): 8.30 (d, J = 2.1 Hz, 1H), 7.36 (s, 1H), 7.28-7.22 (m, 2H), 7.19 (s, 1H), 7.02-6.97 (m, 1H), 6.36 (br.s, exchanged with D$_2$O, 2H), 4.24 (t, J = 6.3 Hz, 2H), 4.06 (t, J = 6.9 Hz, 2H), 3.72 (dd ast, J = 4.5 Hz, 4H), 2.56 (t, J = 7.2 Hz, 2H), 2.50-2.46 (m, 4H), 2.09-2.05 (m, 2H), 1.92-1.84 (m, 2H), 0.92 (t, J = 7.2 Hz, 3H) |
| 164 | 510.2 | (CDCl$_3$): 8.31 (d, J = 2.1 Hz, 1H), 7.34 (s, 1H), 7.28-7.23 (m, 2H), 7.21 (s, 1H), 7.03-6.98 (m, 1H), 6.35 (br.s, exchanged with D$_2$O, 2H), 4.25 (t, J = 6.3 Hz, 2H), 4.05 (t, J = 7.2 Hz, 2H), 2.77-2.65 (m, 6H), 2.19-2.10 (m, 2H), 1.94-1.85 (m, 6H), 0.92 (t, J = 7.2 Hz, 3H) |
| 165 | 538.5 | (CDCl$_3$): 8.30 (d, J = 1.8 Hz, 1H), 7.37 (s, 1H), 7.30-7.26 (m, 2H), 7.17 (s, 1H), 7.00-6.95 (m, 1H), 6.35 (br.s, exchanged with D$_2$O, 2H), 4.19 (t, J = 5.4 Hz, 2H), 4.06 (t, J = 6.9 Hz, 2H), 2.77 (m, 6H), 1.95-1.80 (m, 10H), 1.50 (s, 2H), 0.92 (t, J = 7.5 Hz, 3H) |
| 166 | 540.3 | (CDCl$_3$): 8.30 (d, J = 2.1 HZ, 1H), 7.35 (s, 1H), 7.27-7.22 (m, 2H), 7.19 (s, 1H), 6.99-6.94 (m, 1H), 6.35 (br.s, exchannged with D$_2$O, 2H), 4.18 (t, J = 6.3 Hz, 2H), 4.05 (t, J = 6.9 Hz, 2H), 3.72 (dd as t, J = 4.5 Hz, 4H), 2.48-2.41 (m, 6H), 1.98-1.82 (m, 4H), 1.76-1.67 (m, 2H), 0.92 (t, J = 7.5 Hz, 3H) |
| 167 | 524.5 | (CDCl$_3$): 8.31 (d, J = 2.4 Hz, 1H), 7.38 (s, 1H), 7.30-7.26 (m, 2H), 7.18 (s, 1H), 7.03-6.97 (m, 1H), 6.35 (br.s, exchanged with D$_2$O, 2H), 4.25 (t, J = 6.3 Hz, 2H), 4.05 (t, J = 6.9 Hz, 2H), 2.84-2.77 (m, 4H), 2.26-2.22 (m, 2H), 1.94-1.82 (m, 2H), 1.78 (br s, 6H), 1.56 (s, 2H), 0.92 (t, J = 7.2 Hz, 3H) |
| 168 | 524.5 | (CDCl$_3$): 8.31 (d, J = 2.1 Hz, 1H), 7.37 (s, 1H), 7.29-7.26 (m, 2H), 7.17 (s, 1H), 7.00-6.94 (m, 1H), 6.36 (br.s, exchanged with D$_2$O, 2H), 4.20 (t, J = 5.7 Hz, 2H), 4.06 (t, J = 7.2 Hz, 2H), 2.97-2.91 (m, 6H), 1.98-1.82 (m, 10H), 0.92 (t, J = 7.2 Hz, 3H) |
| 169 | 566.5 | (CDCl$_3$): 8.32 (d, J = 2.1 Hz, 1H), 7.37 (s, 1H), 7.28-7.23 (m, 3H), 7.05-7.00 (m, 1H), 6.36 (br.s, exchanged with D$_2$O, 2H), 4.35-4.28 (m, 1H), 4.23 (t, J = 6.6 Hz, 2H), 4.13-4.10 (m, 2H), 3.55 (td, J = 11.4, 2.1 Hz, 2H), 2.49 (t, J = 6.9 Hz, 2H), 2.40 (br.s, 4H), 2.09-2.01 (m, 6H), 1.57 (s, 4H), 1.46-1.41 (m, 2H) |
| 170 | 568.5 | (CDCl$_3$): 8.32 (br s, 1H), 7.40 (s, 1H), 7.28-7.23 (m, 3H), 7.04-7.0 (m, 1H), 6.37 (br.s, exchanged with D$_2$O, 2H), 4.38-4.30 (m, 1H), 4.25 (t, J = 6.3 Hz, 2H), 4.13-4.09 (m, 2H), 3.72 (dd as t, J = 4.2 Hz, 4H), 3.54 (m, 2H), 2.58-2.48 (m, 6H), 2.09-2.06 (m, 6H) |
| 171 | 552.5 | (CDCl$_3$): 8.31 (d, J = 1.8 Hz, 1H), 7.39 (s, 1H), 7.26-7.23 (m, 3H), 7.02 (m, 1H), 6.36 (br.s. exchanged with D$_2$O, 2H), 4.32-4.25 (m, 3H), 4.13-4.09 (m, 2H), 3.58-3.51 (m, 2H), 2.82-2.72 (m, 6H), 2.21-2.01 (m, 6H), 1.88 (br s, 4H) |
| 172 | 566.20 | (CDCl$_3$): 8.30 (d, J = 2.1 Hz, 1H), 7.33 (s, 2H), 7.26 (s, 1H), 7.20 (s, 1H), 6.96 (t, J = 7.2 Hz, 1H), 6.33 (s, exchanged with D$_2$O, 2H), 4.13-4.03 (m, 4H), 2.29 (s, 6H), 2.15 (br.s, 2H), 2.05-2.00 (m, 1H), 1.79-1.57 (m, 10H), 0.95 (d, J = 6.6 Hz, 6H) |
| 173 | 580.30 | (CDCl$_3$): 8.32 (d, J = 2.1 Hz, 1H), 7.3 (s, 1H), 7.28-7.23 (m, 3H), 7.00-6.95 (m, 1H), 6.37 (s, exchanged with D$_2$O, 2H), 4.35-4.28 (m, 1H), 4.14-4.05 (m, 4H), 3.55 (dt, J = 11.1, 2.4 Hz, 2H), 2.30 (s, 6H), 2.17-1.97 (m, 5H), 1.80-1.65 (m, 9H) |
| 174 | 580.5 | (CDCl$_3$): 8.31 (d, J = 2.1 Hz, 1H), 7.37 (s, 1H), 7.26-7.19 (m, 2H), 6.98 (t, J = 7.2 Hz, 1H), 6.36 (br.s, exchanged with D$_2$O, 2H), 4.35-4.28 (m, 1H), 4.21-4.09 (m, 4H), 3.58-3.50 (m, 2H), 2.40 (s, 6H), 2.09-2.00 (m, 4H), 1.96-1.87 (m, 2H), 1.76-1.66 (m, 2H), 1.61-1.57 (m, 4H), 1.46-1.44 (m, 2H) |
| 175 | 582.5 | (CDCl$_3$): 8.31 (d, J = 1.8 Hz, 1H), 7.39 (s, 1H), 7.26-7.23 (m, 3H), 7.00-6.94 (m, 1H), 6.36 (br.s, exchanged with D$_2$O, 2H), 4.35-4.26 (m, 1H), 4.21-4.09 (m, 4H), 3.73-3.70 (m, 4H), 3.58-3.50 (m, 2H), 2.46-2.41 (m, 6H), 2.08-1.90 (m, 6H), 1.76-1.69 (m, 2H) |
| 176 | 566.2 | (CDCl$_3$): 8.31 (d, J = 2.1 Hz, 1H), 7.37 (s, 1H), 7.26 (m, 3H), 7.00-6.95 (m, 1H), 6.36 (br.s, exchanged with D$_2$O, 2H), 4.35-4.28 (m, 1H), 4.21-4.09 (m, 4H), 3.58-3.50 (m, 2H), 2.54-2.52 (m, 6H), 2.09-1.90 (m, 6H), 1.79-1.71 (m, 6H) |
| 177 | 496.20 | (CDCl$_3$): 8.30 (d, J = 2.1 Hz, 1H), 7.31 (s, 1H), 7.26-7.21 (m, 2H), 7.18 (s, 1H), 7.01-6.96 (m, 1H), 6.37 (br.s, exchanged with D$_2$O, 2H), 4.67 (br.s, 1H), 3.88 (s, 3H), 2.34-2.31 (m, 7H), 2.19-2.14 (m, 2H), 1.75-1.61 (m, 6H) |
| 178 | 566.20 | (CDCl$_3$): 8.31 (d, J = 1.8 Hz, 1H), 7.38 (s, 1H), 7.26-7.22 (m, 3H), 7.00 (t, J = 7.8 Hz, 1H), 6.38 (br.s, exchanged with D$_2$O, 2H), 4.67 (br.s, 1H), 4.34-4.27 (m, 1H), 4.13-4.09 (m, 2H), 3.54 (dt, J = 11.1 Hz, 3.0 Hz, 2H), 2.32 (br.s, 7H), 2.18-1.99 (m, 6H), 1.74-1.66 (m, 6H) |

TABLE 2-continued

Analytical Chararacterization Data for Compounds of Formula I (blank cells indicate that the test was not performed)

| Cmpnd. No. | MS (M + H) | $^1$H-NMR (300 MHz, unless indicated otherwise) NMR peaks given as δ values in ppm |
|---|---|---|
| 179 | 510.20 | (CDCl$_3$): 8.30 (d, J = 2.1 Hz, 1H), 7.32-7.19 (m, 4H), 6.96 (t, J = 7.5 Hz, 1H), 6.34 (br.s, exchanged with D$_2$O, 2H), 4.05 (d, J = 6.9 Hz, 2H), 3.89 (s, 3H), 2.34 (s, 1H), 2.28 (s, 6H), 2.15-2.00 (m, 3H), 1.76-1.61 (br. s, 6H) |

Biological Assay of Compounds of the Invention

EXAMPLE 31 c-MET Kinase Inhibition Assay

Compounds of the invention were screened for their ability to inhibit c-MET kinase using a standard radiometric assay. Briefly, in this kinase assay the transfer of the terminal $^{33}$P-phosphate in $^{33}$P-ATP to substrate polyE4Y is interrogated. The assay was carried out in 96-well plates to a final volume of 100 µL per well containing 1.0 nM c-Met, 100 mM HEPES (pH 7.5), 10 mM MgCl$_2$, 25 mM NaCl, 0.01% BSA, 1 mM DTT, 0.5 mg/mL polyE4Y, and 35 nM ATP. Accordingly, compounds of the invention were dissolved in DMSO to make 10 mM initial stock solutions. Serial dilutions in DMSO were then made to obtain the final solutions for the assay. A 1.5 µL aliquot of DMSO or inhibitor in DMSO was added to each well. The reaction was initiated by the addition of $^{33}$P-ATP and polyE4Y (obtained from Sigma). After 20 min, the reaction was quenched with 50 µL of 30% trichloroacetic acid (TCA) containing 4 mM ATP. The reaction mixture was transferred to the 0.66 mm GF filter plates (Corning) and washed three times with 5% TCA. Following the addition of 50 µL of Ultimate Gold™ high efficiency scintillant (Packard Bioscience), the samples were counted in a Packard TopCount NXT Microplate Scintillation and Luminescence Counter (Packard BioScience). The K$_i$ values were calculated using Microsoft Excel Solver macros to fit the data to the kinetic model for competitive tight-binding inhibition. Each of Compounds 1 to 179 had a K$_i$ of 3.9 micromolar or less as measured by this assay.

EXAMPLE 32

Inhibition of c-Met Activity in Snu5 Gastric Carcinoma Cells

Compounds of the invention were also screened for their ability to inhibit the Luciferase-induced signal in an engineered Snu5 cell line. Snu5 [obtained from American Type Culture Collection (Catalog number CRL-5973)] is a human gastric carcinoma known to overexpress c-Met, which is constitutively active. The cell line was transduced with the retrovirus, pCLPCX, which contains a genetic construct consisting of 6xAP1 promoter response elements and a luciferase gene having a C-terminal PEST sequence (proteolytic signal from mouse ornithine decarboxylase, which reduces the half-life of the luciferase). The constitutively active cMet activates cellular pathways (principally MAP kinase), resulting in AP-1-induced transcription of luciferase-PEST and translation into the final product, the activity of which is quantifiable as a chemiluminescent readout upon the addition of luciferin (Steady-Glo from Promega.). Residual luminescence is strongly correlated to the inhibition of c-Met. A stable cell line was obtained by selecting the new cell line (Snu5-AP1-Luc-Pest) with puromycin. The cells were grown in complete media [Iscove's media (Invitrogen) containing 10% fetal bovine serum (FBS, Hyclone) and penicillin/gentamycin (Invitrogen)]. Compounds of the invention were dissolved in DMSO to make 10 mM initial stock solutions. Serial dilutions in DMSO were then made and transferred to complete medium to make a 10× solution. The Snu5-AP1-Luc-Pest cells were counted and diluted to 200,000-cells/mL solution. The cells (90 µL) were added to each well in a 96-well black with clear bottom plate (Costar). Then 10 µL of the 10× compound solution was added to the cells in triplicate. The plates were incubated in a 37° C./5% CO$_2$ incubator. After 6 hours, 50 µL of the Steady Glo reagent (Promega) was added to each well and placed on a plate shaker for 5 minutes to ensure that the cells were completely lysed. The plate was read on a 1450 Microbeta Liquid Scintillation and Luminescence Counter (Perkin-Elmer). The IC$_{50}$s were calculated using a 4-parameter fit using the graphing software Prism (GraphPad). Compounds 2, 4, 7-10, 21, 28, 31-34, 38-39, 42, 44, 46-49, 53-54, 57, 61, 63, 73, 91, 97, 99, 103, 106-109, 112-115, 120-122, 124-125, 128-134, 136-139, 141-142, 144-149, and 151-179 had IC$_{50}$'s of 0.50 micromolar or less.

All publications and patents cited in this specification are herein incorporated by reference as if each individual publication or patent were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:
1. A compound having the formula:

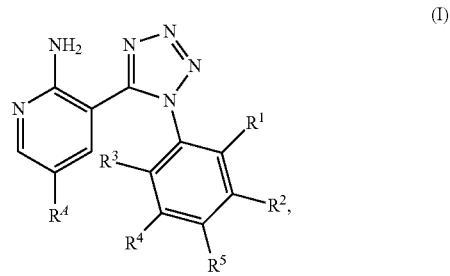

or a pharmaceutically acceptable salt thereof, wherein
R$^4$ is a phenyl ring or 5 to 9 membered heteroaryl ring having up to 2 heteroatoms selected from N, O or S, wherein said phenyl or heteroaryl ring is optionally substituted with up to 2 groups selected from halogen, C$_{1-5}$ aliphatic, —NR'C(O)R', —C(O)N(R')₂-OR', (CH₂)₀₋₂N(R')₂, tetrahydropyranyl, or piperidinyl;

R' is hydrogen or $C_{1-4}$ alkyl;

each of $R^1$, $R^2$, $R^3$, and $R^4$ is, individually, hydrogen, Cl, or F, wherein at least one of $R^1$, $R^2$, $R^3$, and $R^4$ is Cl or F;

$R^5$ is

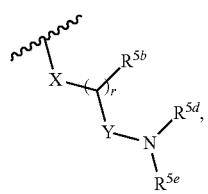

wherein

X is O or $NR^{5a}$

Y is $C_{1-4}$ aliphatic or $C_{3-6}$ cycloaliphatic, optionally substituted with $R^{5c}$, r is 0 or 1, each of $R^{5a}$, $R^{5b}$, $R^{5c}$, $R^{5d}$ and $R^{5e}$ is, independently, hydrogen or $C_{1-4}$ aliphatic, wherein $R^{5a}$ and $R^{5d}$ or $R^{5c}$ and $R^{5d}$ together optionally form a pyrrolidine or piperidine ring, $R^{5b}$ and $R^{5c}$ together optionally form a 5-6-membered carbocyclic ring, and $R^{5d}$ and $R^{5e}$ together optionally form a pyrrolidine, piperidine or morpholine ring.

2. The compound according to claim 1, or a pharmaceutically acceptable salt thereof, wherein $R^4$ is an optionally substituted pyrazol-4-yl, thiophen-3-yl, thiophen-2-yl, benzo[b]thiophen-2-yl, phenyl, benzo[b]thiophen-3-yl, pyridine-4-yl, pyridine-3-yl, or pyrimidin-5-yl ring.

3. The compound according to claim 2, or a pharmaceutically acceptable salt thereof, wherein $R^4$ is an optionally substituted pyrazol-4-yl, thiophen-3-yl, or thiophen-2-yl ring.

4. The compound according to claim 3, or a pharmaceutically acceptable salt thereof, wherein $R^4$ is selected from

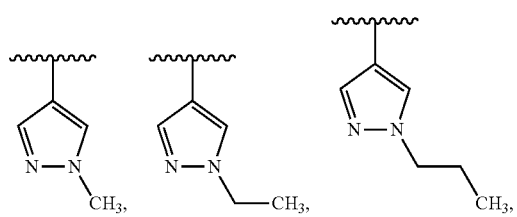

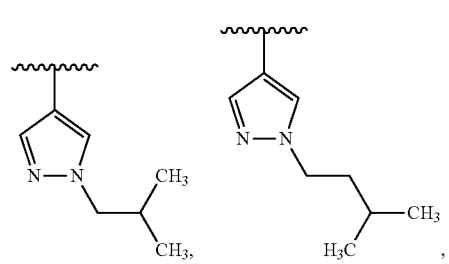

-continued

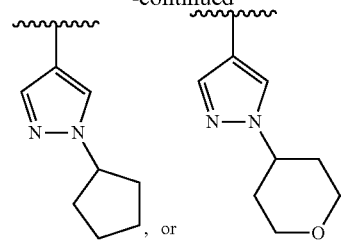

, or .

5. The compound according to claim 1, or a pharmaceutically acceptable salt thereof, wherein X is O and the number of atoms between X and $N(R^{5d})(R^{5e})$ is 3, 4, or 5.

6. The compound according to claim 5, wherein $R^5$ is

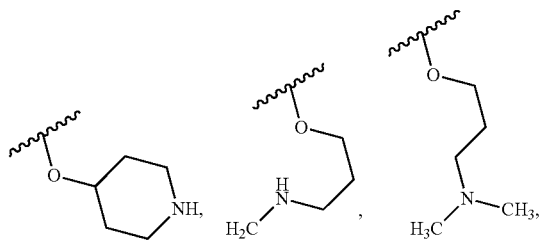

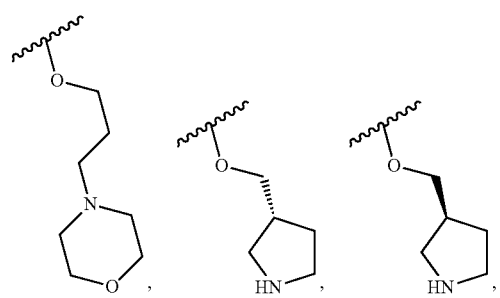

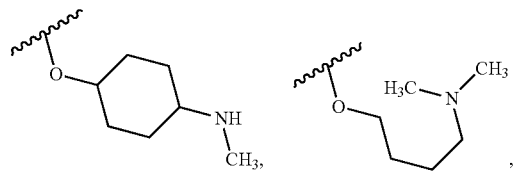

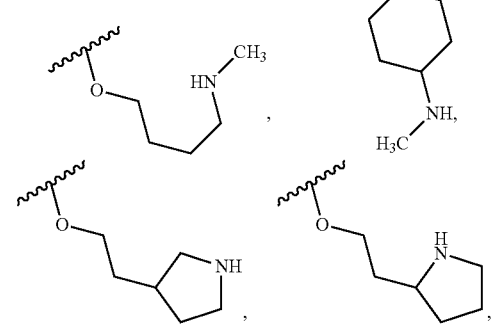

107

-continued

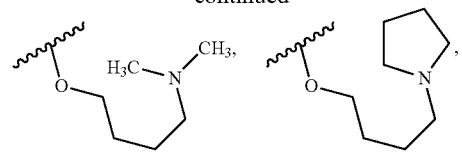

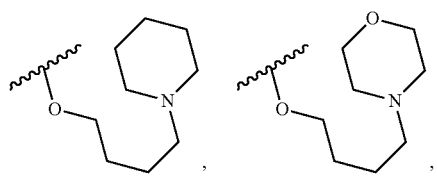

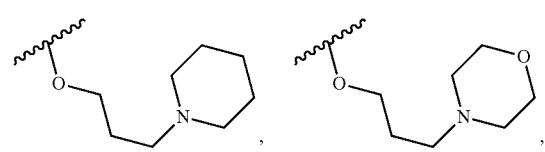

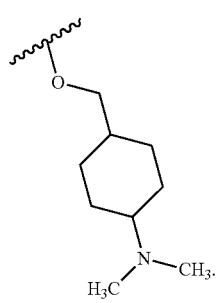

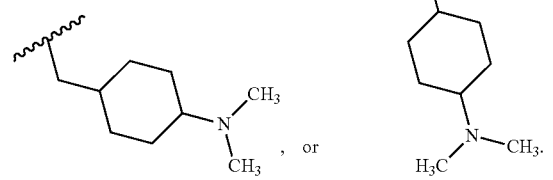, or

7. The compound according to claim 1, or a pharmaceutically acceptable salt thereof, wherein one or two of $R^1$, $R^2$, $R^3$, and $R^4$ is fluorine and the remainder of $R^1$, $R^2$, $R^3$, and $R^4$ are hydrogen.

8. The compound according to claim 7, or a pharmaceutically acceptable salt thereof, wherein each of $R^1$ and $R^2$ is fluorine and each of $R^3$ and $R^4$ is hydrogen.

9. A compound selected from:

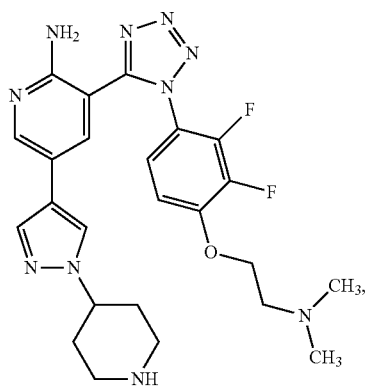

108

-continued

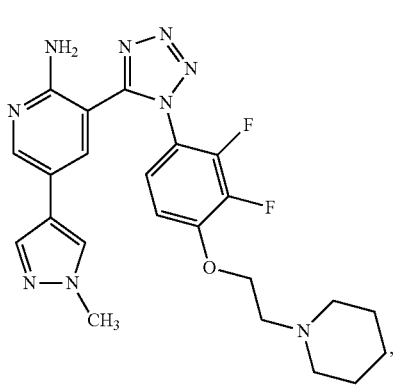

109
-continued
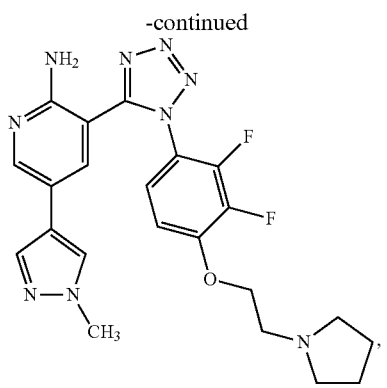
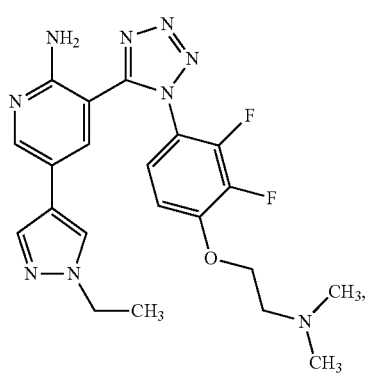
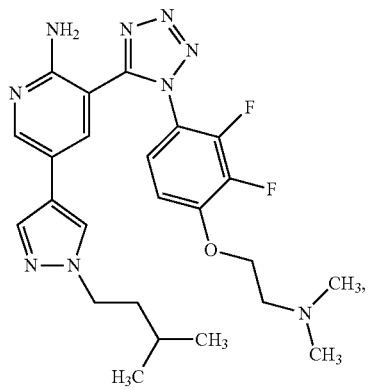
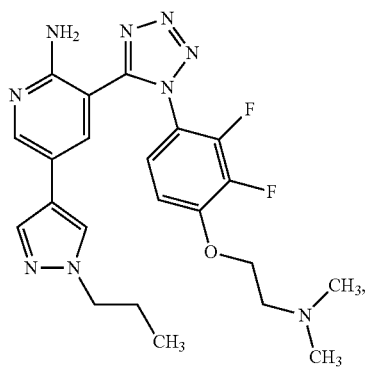
110
-continued
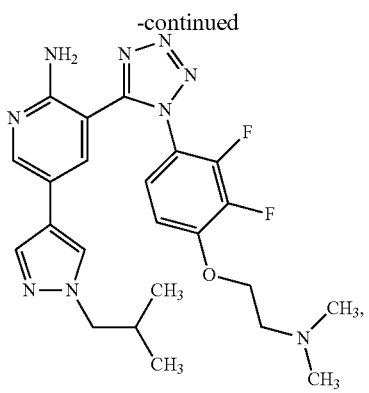
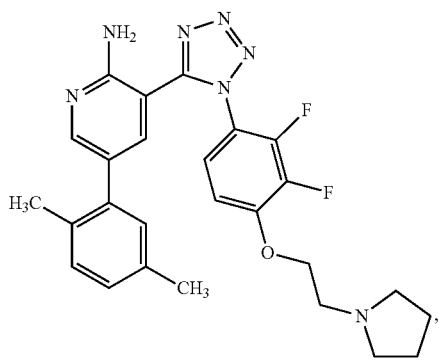
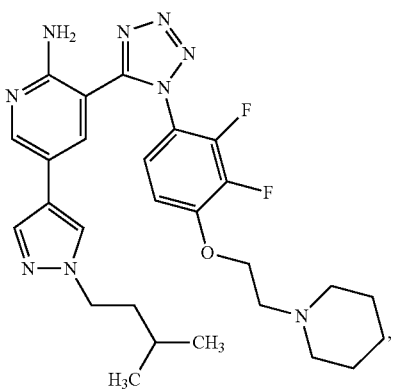
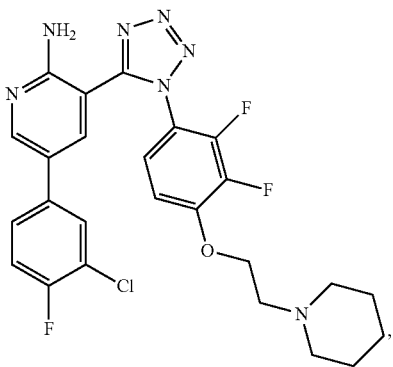

-continued

113 -continued
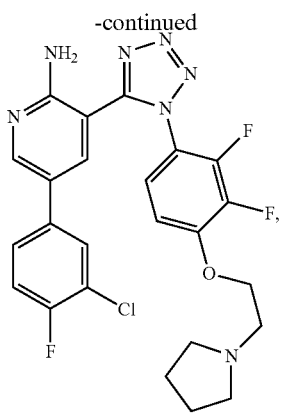
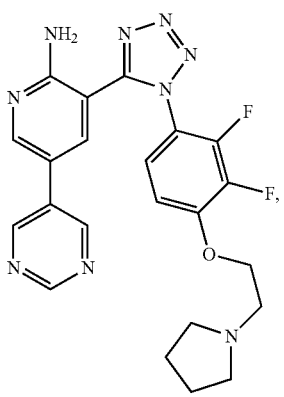
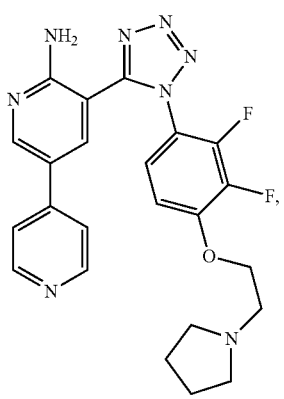
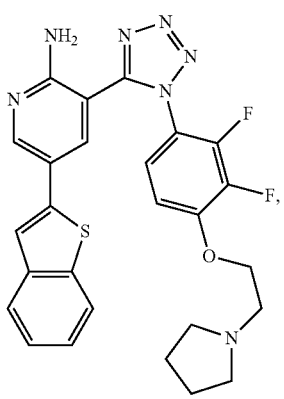
114 -continued
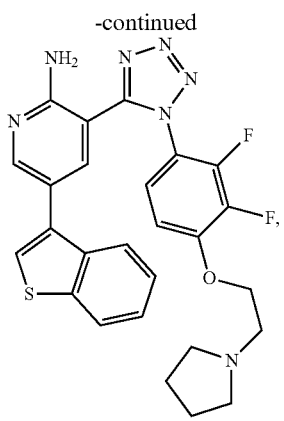
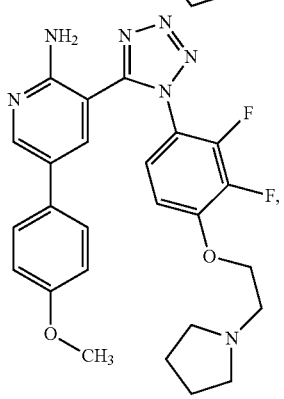
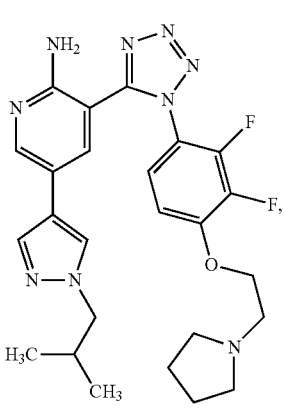
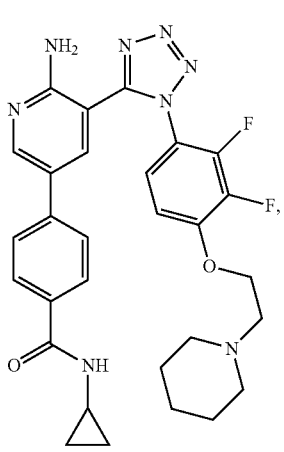

115
-continued
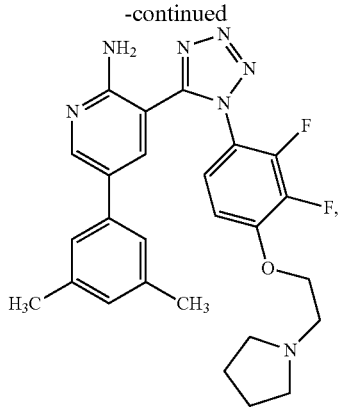
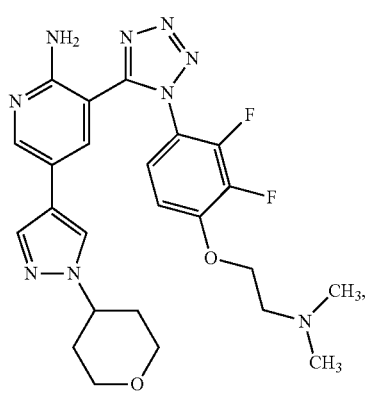
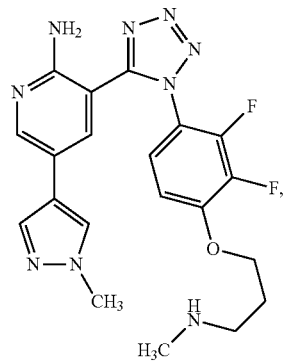
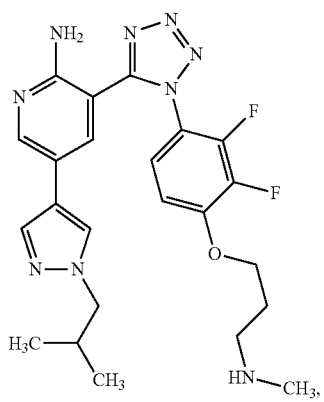
116
-continued
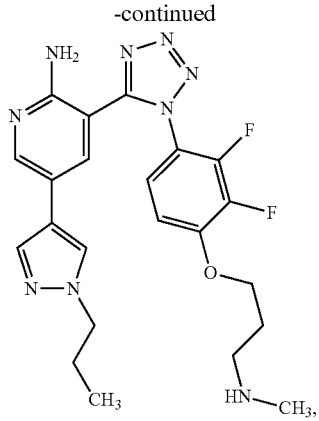
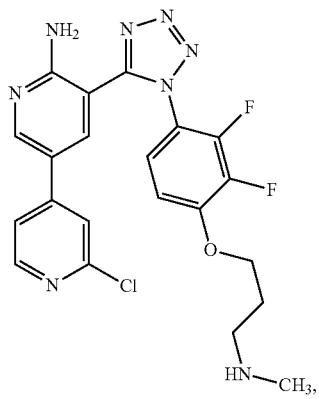
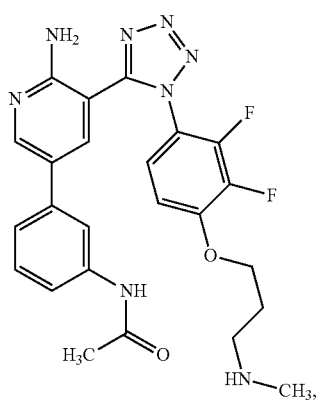
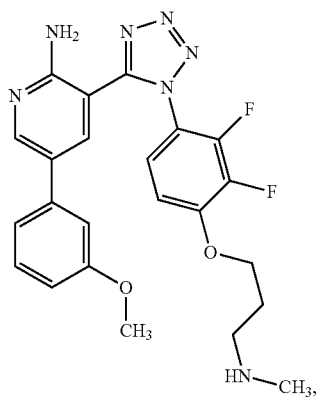

117
-continued
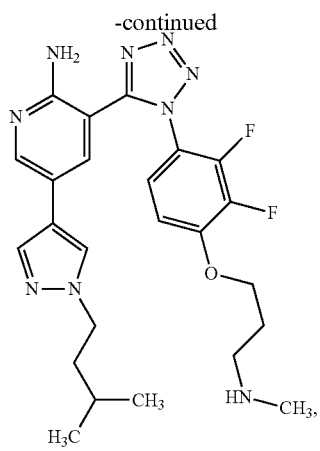
118
-continued
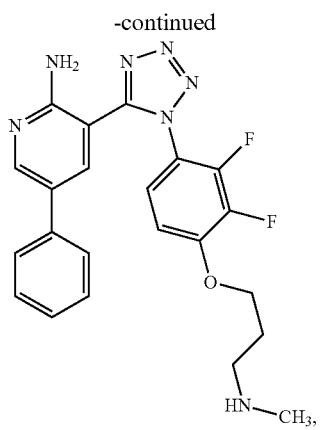
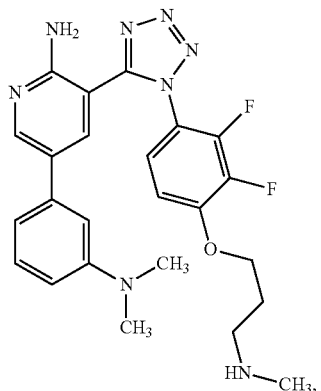
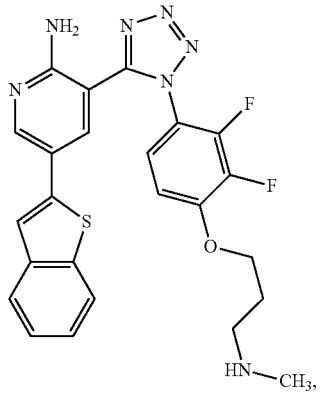
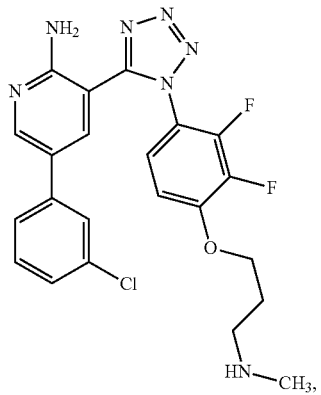

119
-continued
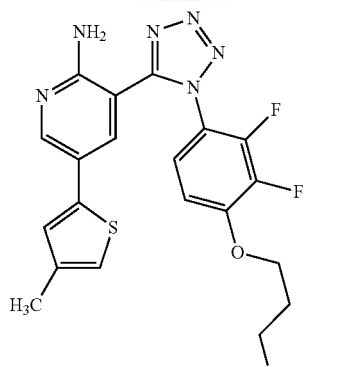
120
-continued
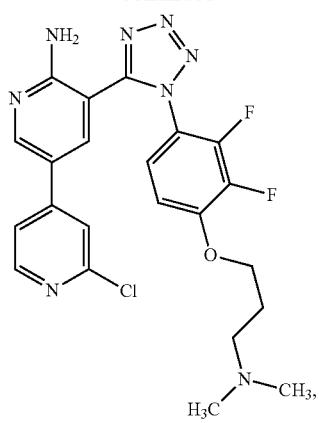
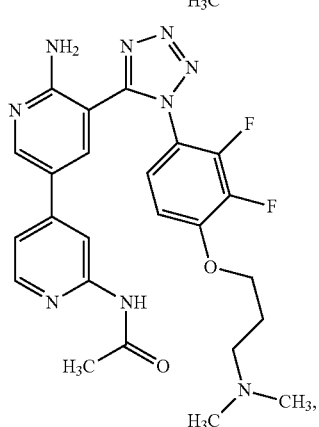
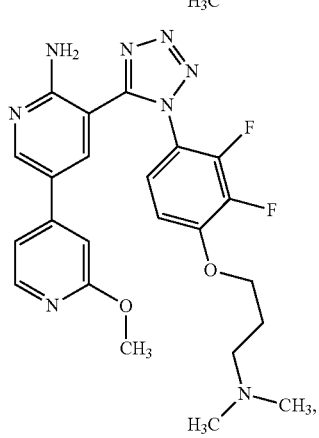
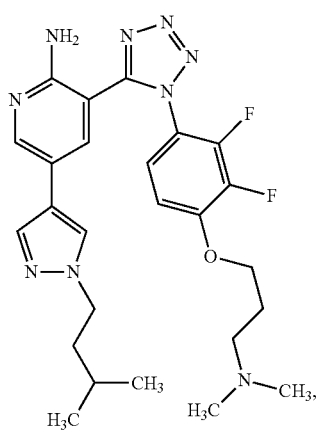

-continued

123
-continued
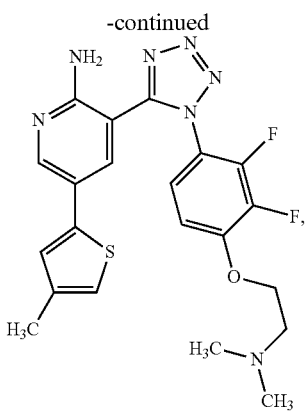
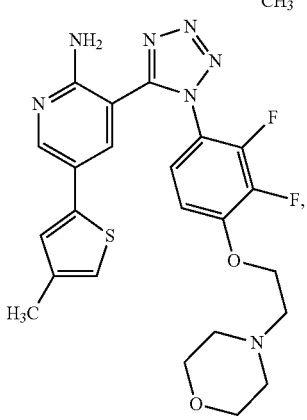
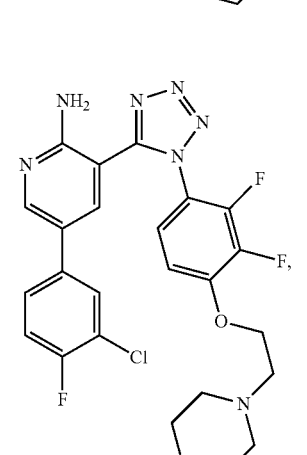
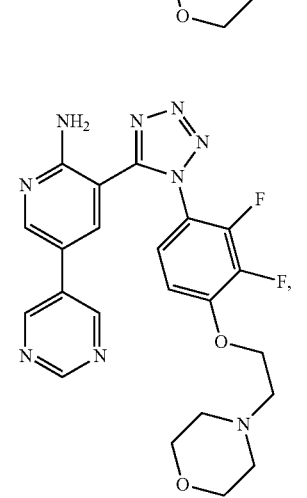
124
-continued
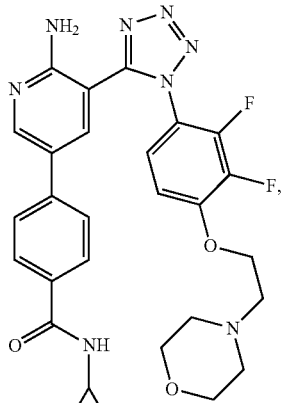
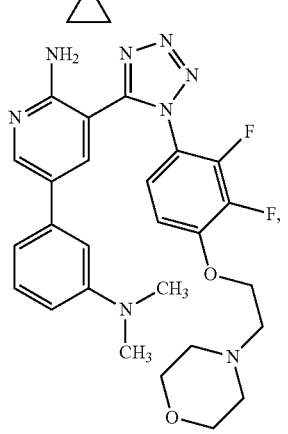
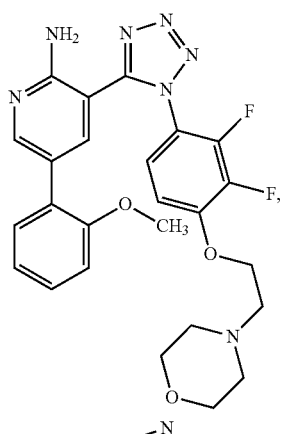
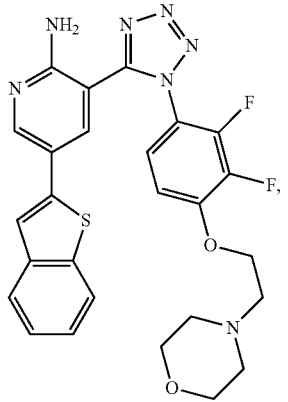

125
-continued
126
-continued
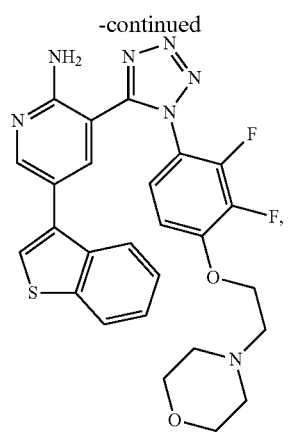
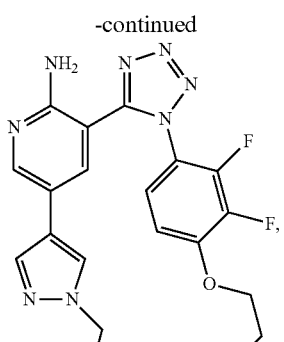
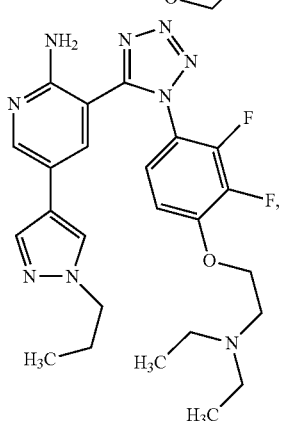
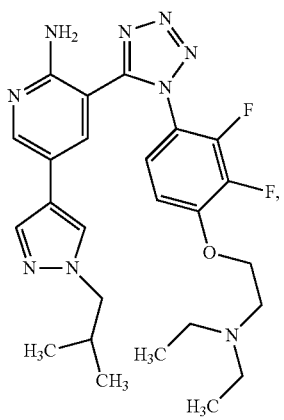
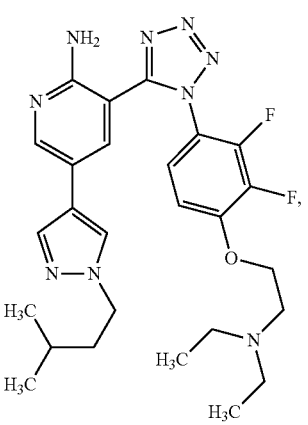

127
-continued
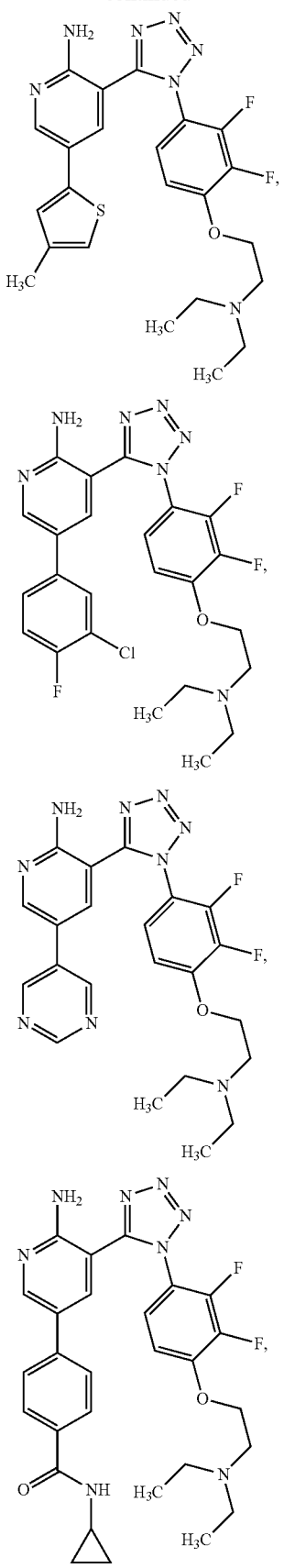
128
-continued
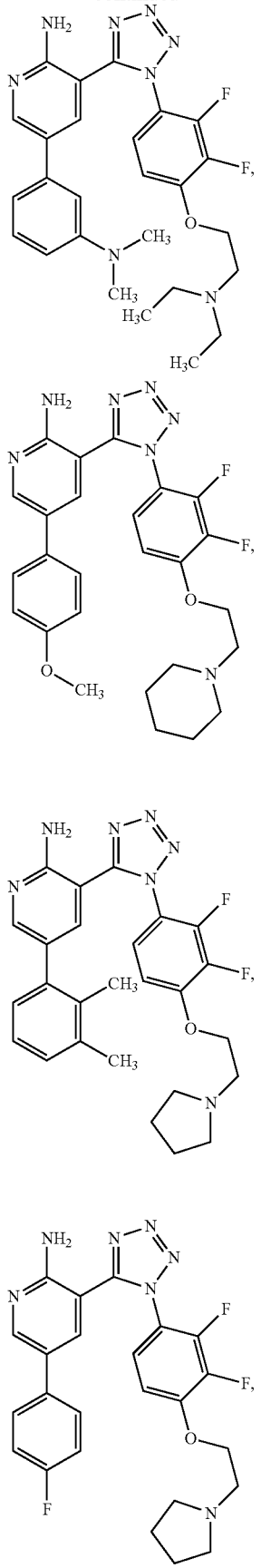

-continued

131
-continued
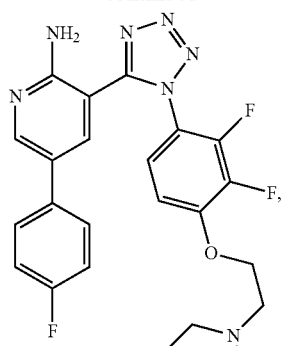
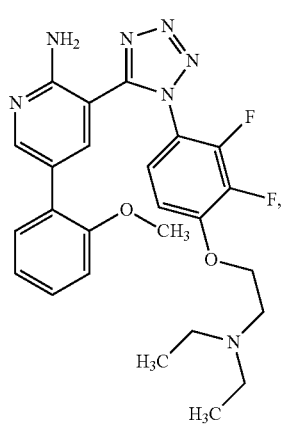
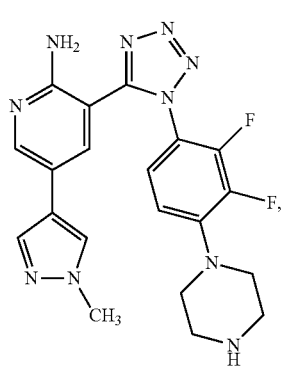
132
-continued
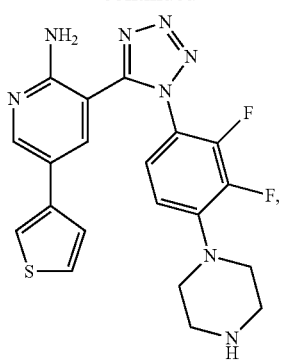
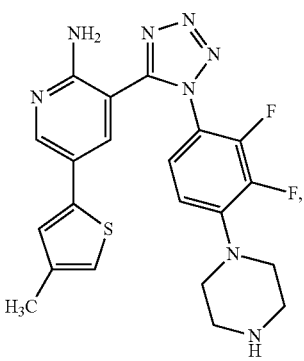
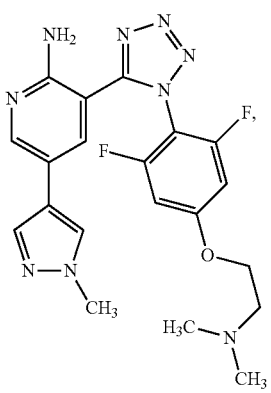
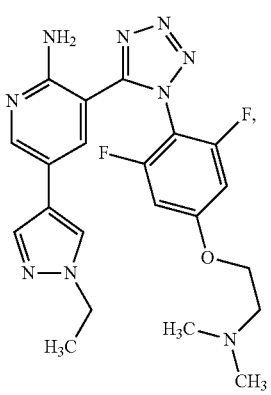

133
-continued
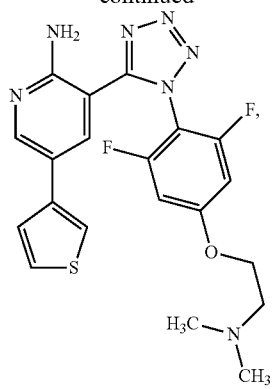
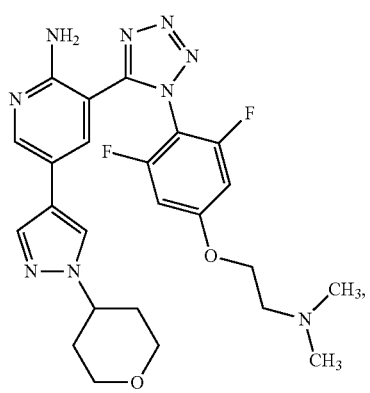
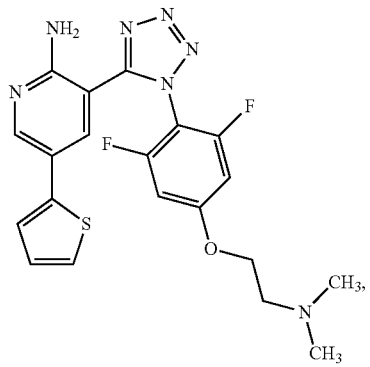
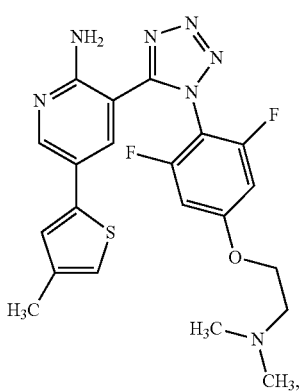
134
-continued
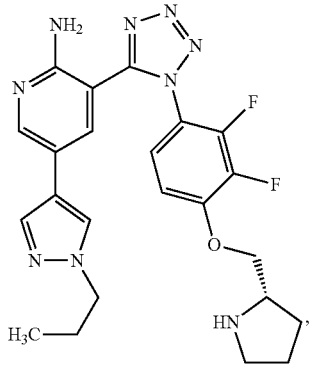
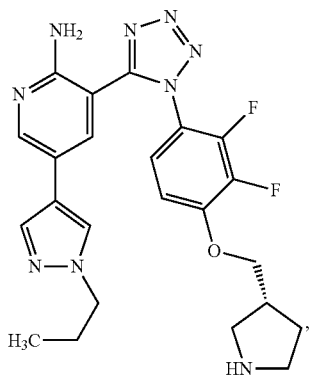
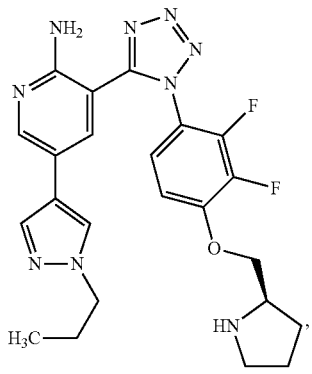
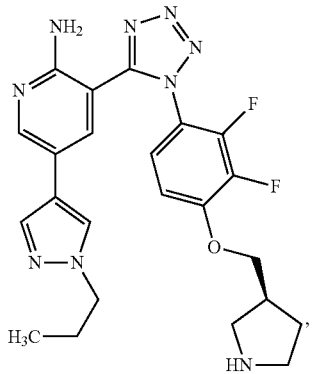

135
-continued
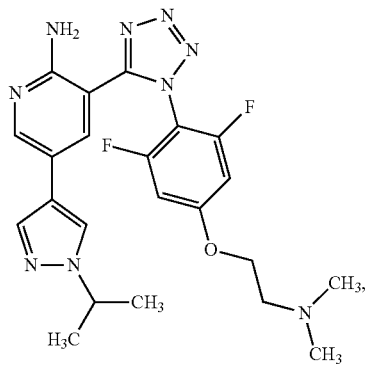
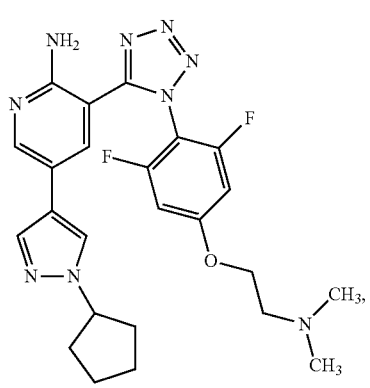
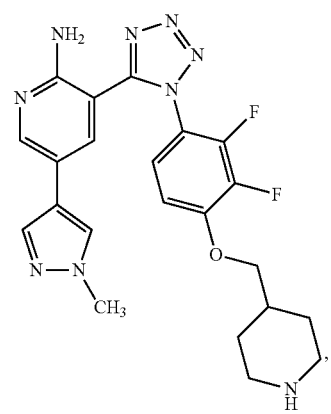
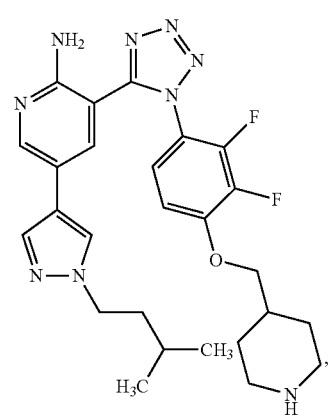
136
-continued
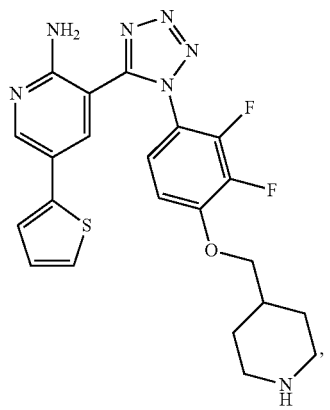
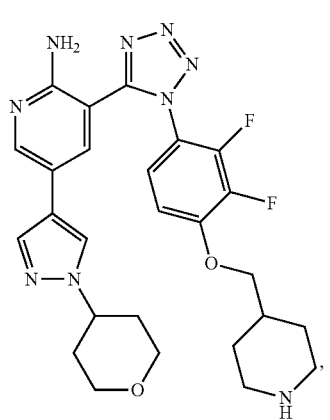
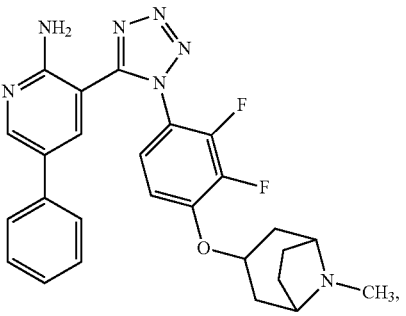
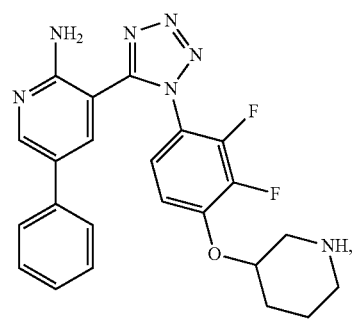

137
-continued
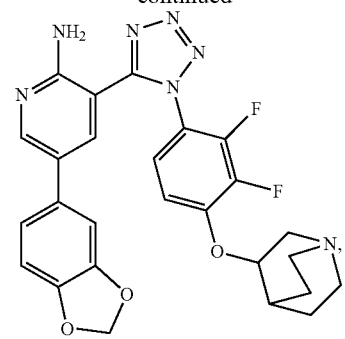
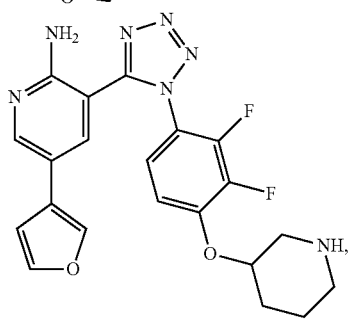
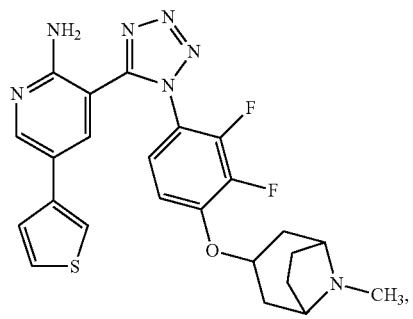
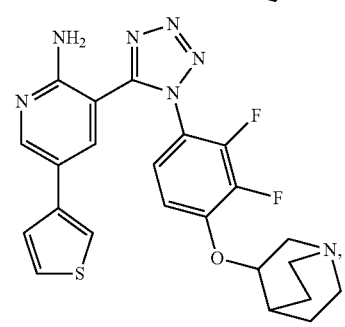
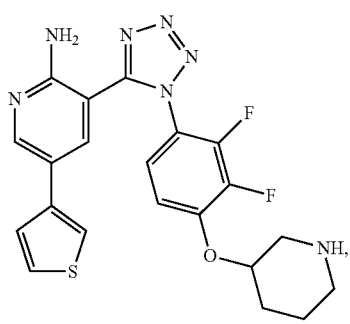
138
-continued
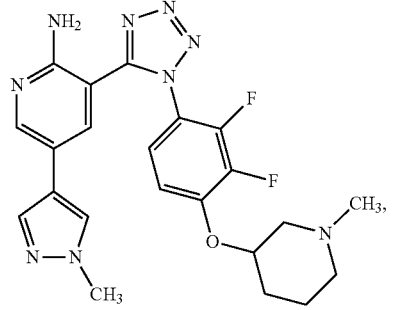
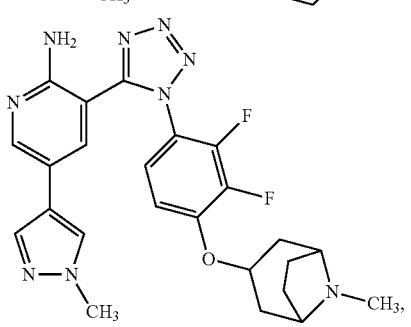
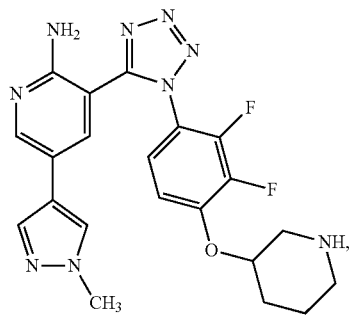
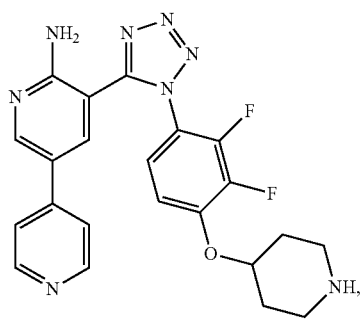
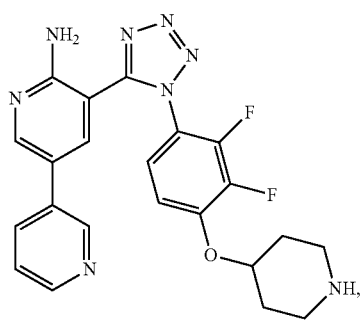

139
-continued
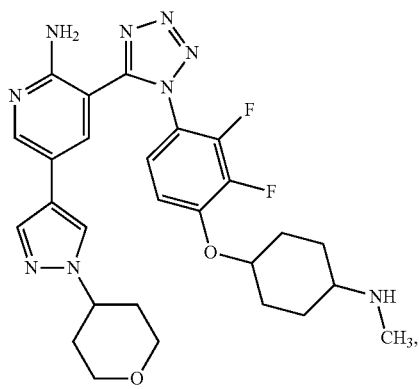
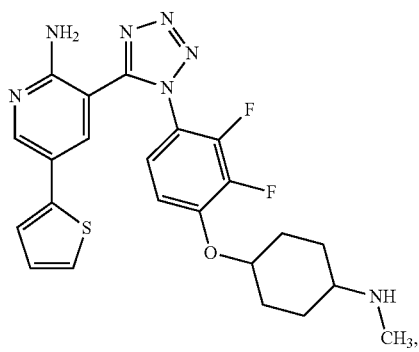
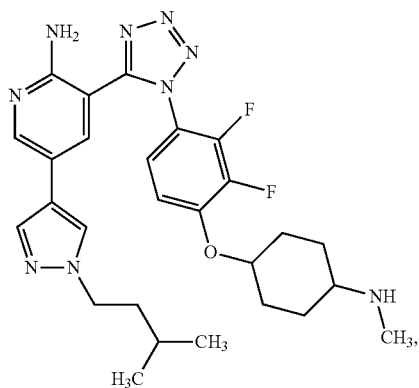
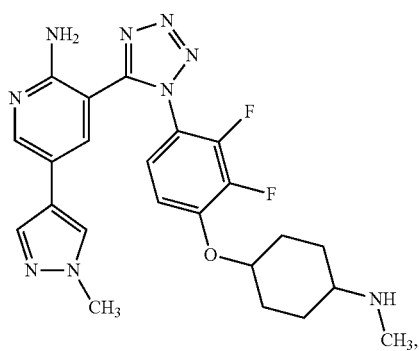
140
-continued
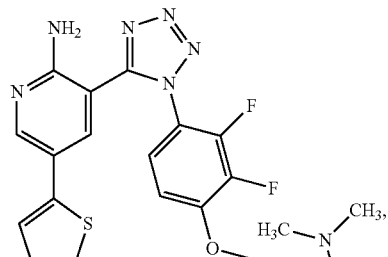
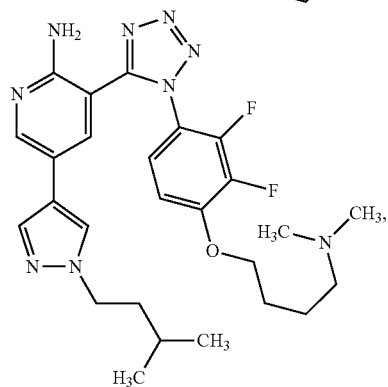
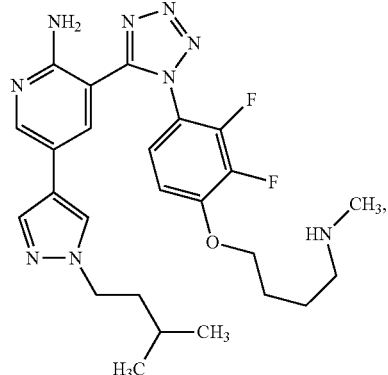
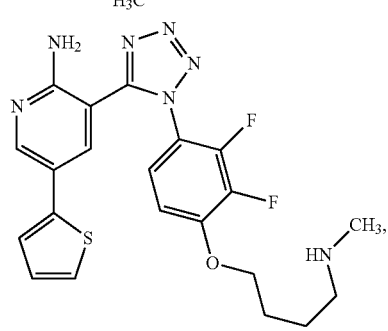
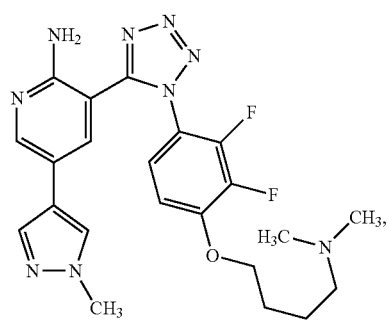

141
-continued
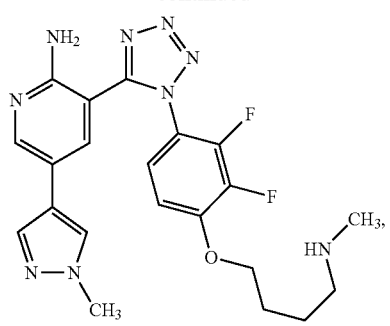
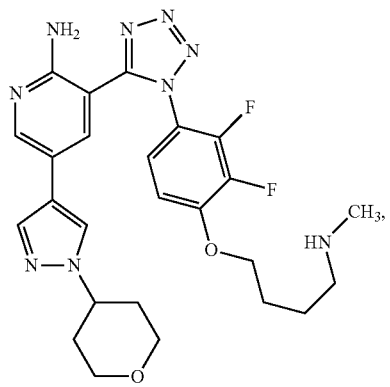
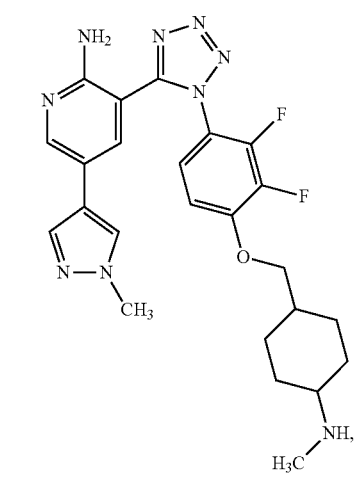
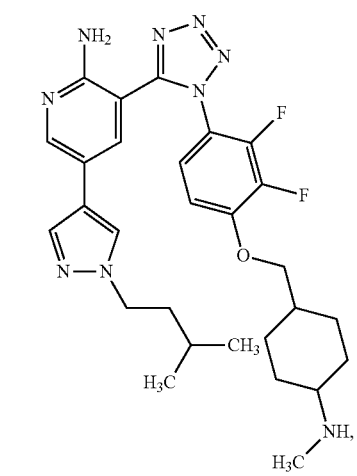
142
-continued
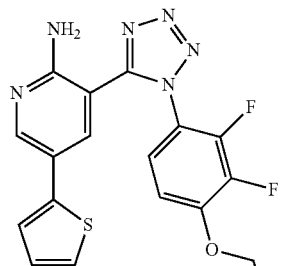
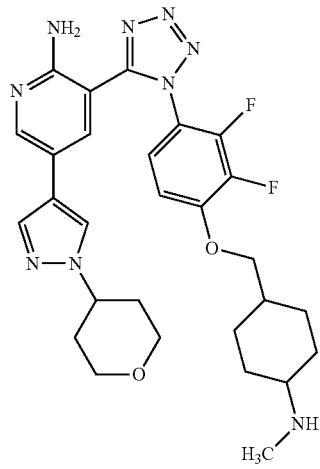
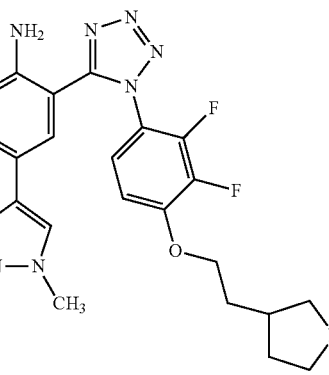
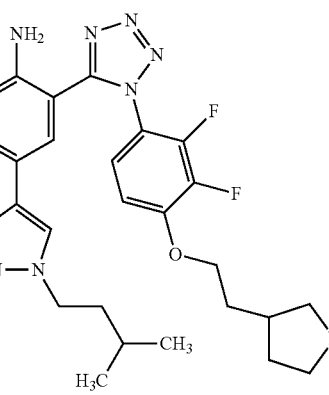

-continued

145
-continued
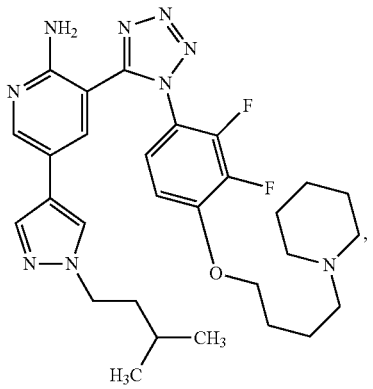
146
-continued
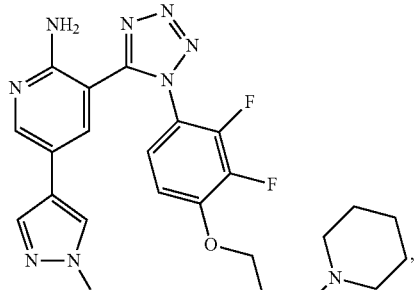
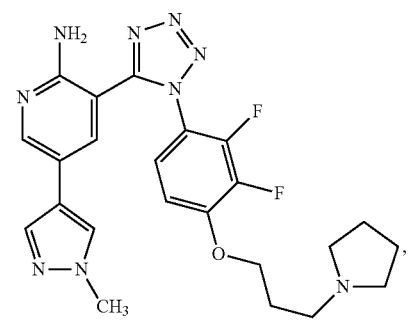
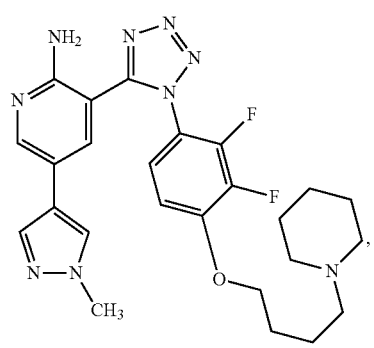
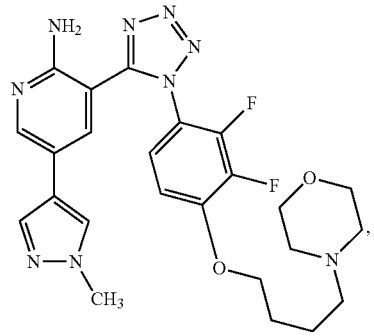
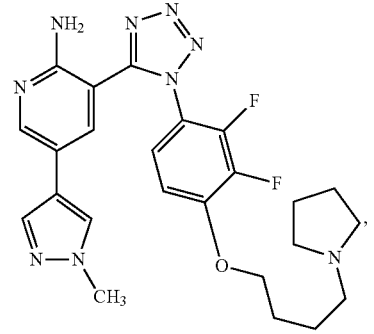

147
-continued
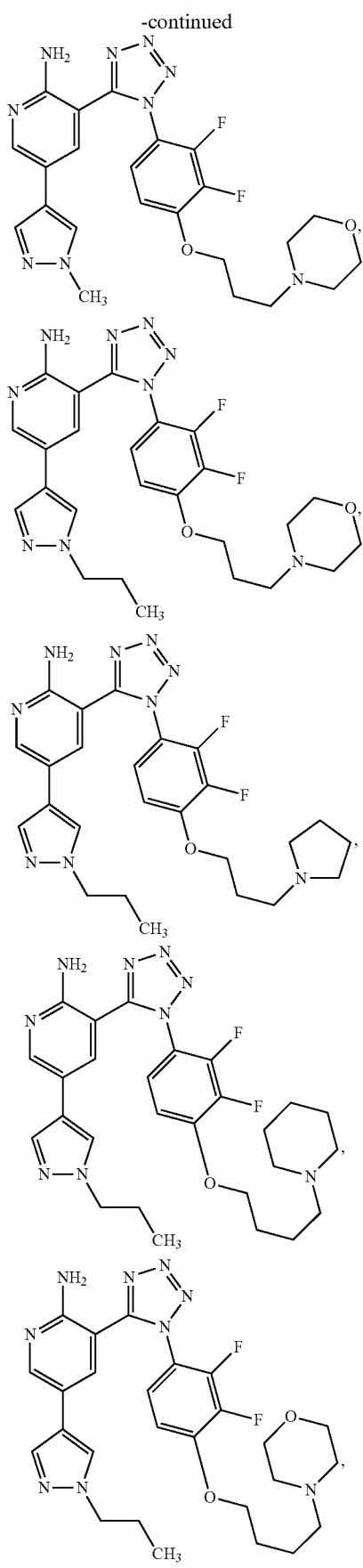
148
-continued
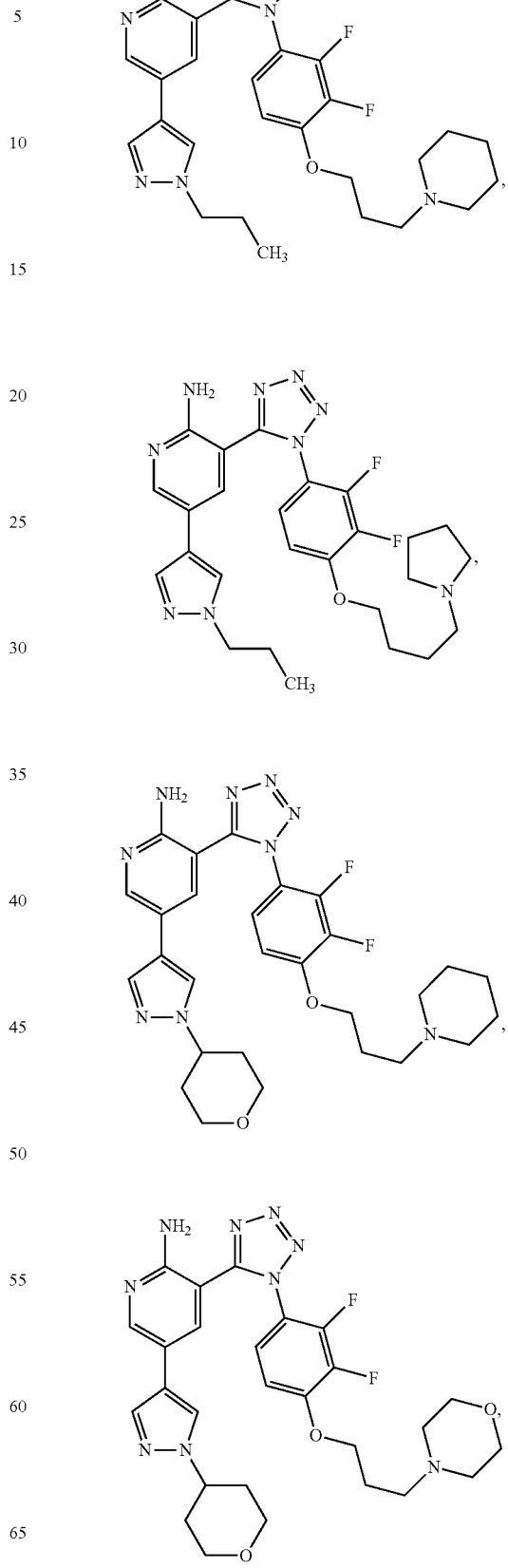

149
-continued
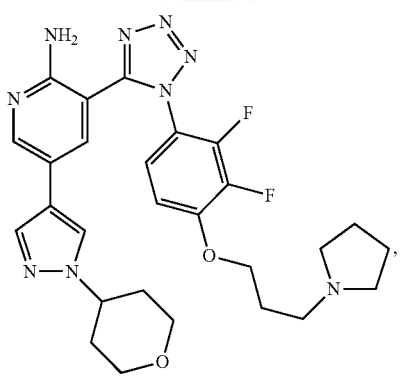
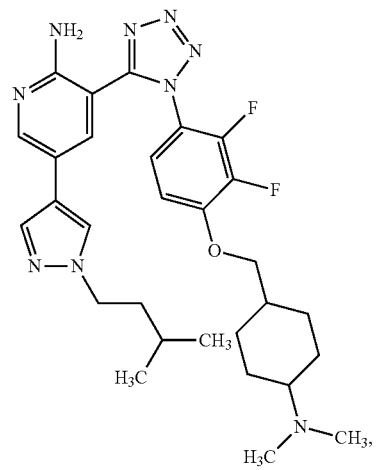
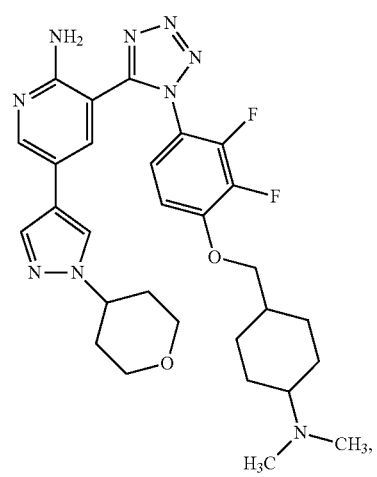
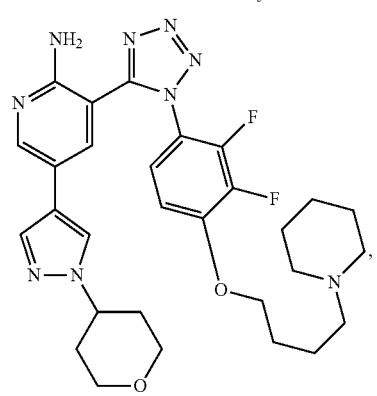
150
-continued
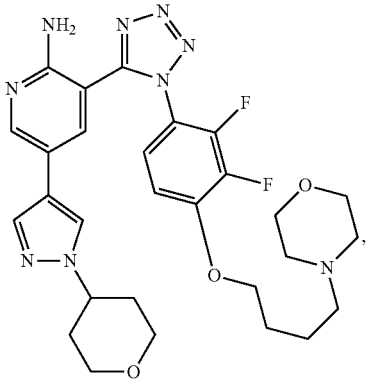
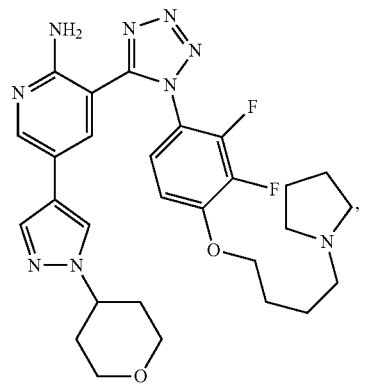 [SMILES: Nc1ncc(-c2cnn(C3CCOCC3)c2)cc1-c1nnnn1-c1ccc(OCCCCN2CCCCC2)c(F)c1F]
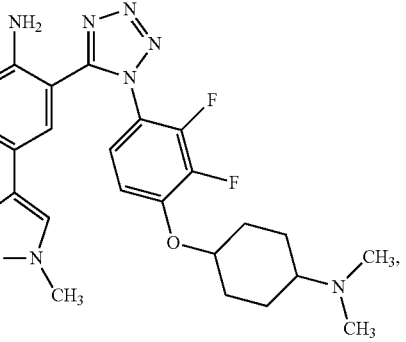
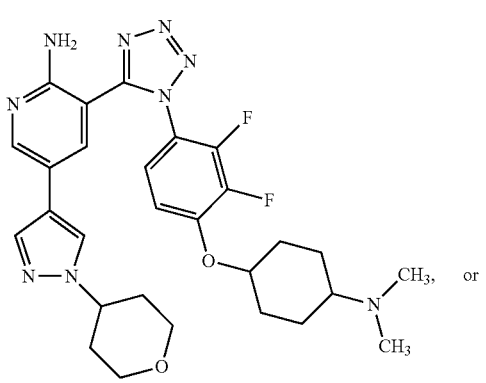

-continued

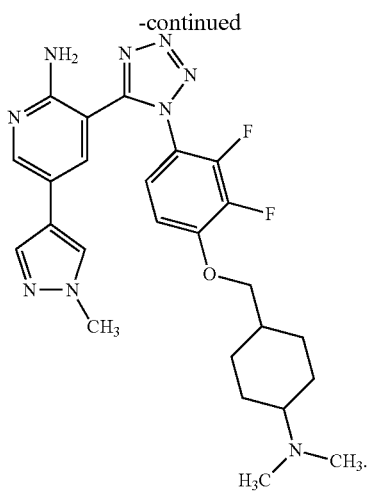

10. A pharmaceutical composition comprising a compound according to claim 1 or claim 9, or a pharmaceutically acceptable salt thereof, and a pharmaceutically acceptable carrier, adjuvant or vehicle.

11. A method of treating or lessening the severity of a glioblastoma; a gastric carcinoma; or a cancer selected from colon, breast, prostate, brain, liver, pancreatic or lung cancer in a patient, comprising administering a compound according to claim 1 or claim 9, or a pharmaceutical composition comprising said compound, to said patient in a therapeutically effective amount.

* * * * *